(12) United States Patent
Yoshioka et al.

(10) Patent No.: US 12,390,534 B2
(45) Date of Patent: Aug. 19, 2025

(54) BRANCHED DEGRADABLE POLYETHYLENE GLYCOL BINDER

(71) Applicants: NOF CORPORATION, Tokyo (JP); TOKYO INSTITUTE OF TECHNOLOGY, Tokyo (JP)

(72) Inventors: Hiroki Yoshioka, Kawasaki (JP); Kazuki Osakama, Kawasaki (JP); Mika Hamura, Kawasaki (JP); Takanori Inaba, Kawasaki (JP); Nobuhiro Nishiyama, Tokyo (JP); Makoto Matsui, Tokyo (JP); Hiroyasu Takemoto, Tokyo (JP); Takahiro Nomoto, Tokyo (JP); Xiaohang Sun, Tokyo (JP)

(73) Assignees: NOF CORPORATION, Tokyo (JP); TOKYO INSTITUTE OF TECHNOLOGY, Tokyo (JP)

( * ) Notice: Subject to any disclaimer, the term of this patent is extended or adjusted under 35 U.S.C. 154(b) by 461 days.

(21) Appl. No.: 17/599,402

(22) PCT Filed: Mar. 26, 2020

(86) PCT No.: PCT/JP2020/013600
§ 371 (c)(1),
(2) Date: Sep. 28, 2021

(87) PCT Pub. No.: WO2020/203626
PCT Pub. Date: Oct. 8, 2020

(65) Prior Publication Data
US 2022/0387609 A1    Dec. 8, 2022

(30) Foreign Application Priority Data

Mar. 29, 2019    (JP) .................. 2019-069450

(51) Int. Cl.
*A61K 47/64* (2017.01)
*A61K 47/60* (2017.01)

(52) U.S. Cl.
CPC .............. *A61K 47/64* (2017.08); *A61K 47/60* (2017.08)

(58) Field of Classification Search
None
See application file for complete search history.

(56) References Cited

U.S. PATENT DOCUMENTS

| | | | |
|---|---|---|---|
| 2007/0105809 A1 | 5/2007 | Rusconi | |
| 2008/0139459 A1 | 6/2008 | Bos et al. | |
| 2009/0023859 A1 | 1/2009 | Sakanoue et al. | |
| 2010/0010158 A1 | 1/2010 | McManus et al. | |
| 2012/0039843 A1 | 2/2012 | Bos et al. | |
| 2016/0095933 A1 | 4/2016 | Coady et al. | |

FOREIGN PATENT DOCUMENTS

| | | | |
|---|---|---|---|
| CN | 106421806 A | 2/2017 | |
| JP | 2007-534324 A | 11/2007 | |
| JP | 2008-538200 A | 10/2008 | |
| JP | 2009-527581 A | 7/2009 | |
| JP | 2017-535633 A | 11/2017 | |
| WO | WO 2005/108463 A2 | 11/2005 | |
| WO | WO 2006/088248 A1 | 8/2006 | |
| WO | WO-2009123768 A2 * | 10/2009 | ........... A61K 31/704 |
| WO | WO 2011/146518 A2 | 11/2011 | |

OTHER PUBLICATIONS

Vugmeyster et al. "Pharmacokinetic, Biodistribution, and Biophysical Profiles of TNF Nanobodies Conjugated to Linear or Branched Poly(ethylene glycol)," Bioconjugate Chem. 2012, 23(7), 1452-1462 (Year: 2012).*
Fishburn "The Pharmacology of PEGylation: Balancing PD with PK to Generate Novel Therapeutics," Journal of Pharmaceutical Sciences, 2008, 97(10), 4167-4183 (Year: 2008).*
Yuan et al. "A Novel Poly(L-glutamic acid) Dendrimer Based Drug Delivery System with Both pH-Sensitive and Targeting Functions," Molecular Pharmaceutics, 2010, 7(4), 953-962 (Year: 2010).*
Google patent English translation of CN106421806 (Year: 2023).*
Zhang et al. "Peptide-Based Multifunctional Nanomaterials for Tumor Imaging and Therapy," Adv. Funct. Mater. 2018, 28, 1804492, 1-22 (Year: 2018).*
Kyte et al. "A simple method for displaying the hydropathic character of a protein," J. Mol. Biol. 1982, 157: 105-132 (Year: 1982).*
She et al., "The Potential of Self-assembled, pH-responsive Nanoparticles of mPEGylated Peptide Dendron-doxorubicin Conjugates for Cancer Therapy," *Biomaterials*, 34(5): 1613-1623 (2013).
European Medicines Agency, "CHMP Safety Working Party's response to the PDCO regarding the use of PEGylated drug products in the paediatric population," EMA/CHMP/SWP/647258 (Nov. 16, 2012).
Li et al., "Tumor-Specific Multiple Stimuli-Activated Dendrimeric Nanoassemblies with Metabolic Blockade Surmount Chemotherapy Resistance," *ACS Nano.*, 11(1): 416-429 (2017).
López Rivas et al., "Synthesis and Biological Evaluation of Paclitaxel Conjugates Involving Linkers Cleavable by Lysosomal Enzymes and $\alpha_\nu\beta_3$-Integrin Ligands for Tumor Targeting," *Eur. J. Org. Chem.*, 23: 2902-2909 (2018).
Rudmann et al., "High Molecular Weight Polyethylene Glycol Cellular Distribution and PEG-associated Cytoplasmic Vacuolation Is Molecular Weight Dependent and Does Not Require Conjugation to Proteins," *Toxicol. Pathol.*, 41(7): 970-983 (2013).

(Continued)

*Primary Examiner* — Christina Bradley
(74) *Attorney, Agent, or Firm* — Leydig, Voit & Mayer, Ltd.

(57) ABSTRACT

A bio-related substance bonded to a branched and degradable polyethylene glycol derivative that is degraded in the cells represented by the following formula (A):

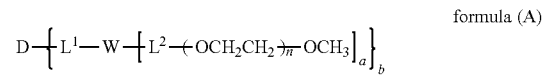

formula (A)

wherein each symbol is as defined in the present specification, is provided by the present invention.

12 Claims, 13 Drawing Sheets
Specification includes a Sequence Listing.

(56) References Cited

OTHER PUBLICATIONS

Veronese et al., "PEG-Doxorubicin Conjugates: Influence of Polymer Structure on Drug Release, in Vitro Cytotoxicity, Biodistribution, and Antitumor Activity," *Bioconjug. Chem.*, 16(4): 775-784 (2005).
Vugmeyster et al., "Pharmacokinetic, Biodistribution, and Biophysical Profiles of TNF Nanobodies Conjugated to Linear or Branched Poly(ethylene glycol)," *Bioconjug. Chem.*, 23(7): 1452-1462 (2012).
Yang et al., "Synthesis and Characterization of Enzymatically Degradable PEG-Based Peptide-Containing Hydrogels," *Macromol. Biosci.*, 10(4): 445-454 (2010).
Japanese Patent Office, International Search Report in International Patent Application No. PCT/JP2020/013600 (Jun. 23, 2020).
Veiman et al., "PEG Shielded MMP Sensitive CPPs for Efficient and Tumor Specific Gene Delivery In Vivo," *J. Control. Release*, 209: 238-247 (2015).

* cited by examiner

BRANCHED DEGRADABLE POLYETHYLENE GLYCOL BINDER

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 3,894 bytes ASCII (Text) file named "757811SequenceListing.txt," created Sep. 28, 2021.

TECHNICAL FIELD

The present invention relates to a bio-related substance bonded to a branched and degradable polyethylene glycol derivative that is degraded in the cells.

BACKGROUND ART

Pharmaceutical products that use bio-related substances such as hormone, cytokine, antibody, and enzyme are generally rapidly discharged from the body after administration to the body due to glomerular filtration in the kidney and uptake by macrophages in the liver and spleen. Therefore, the half-life in blood is short, and it is often difficult to obtain a sufficient pharmacological effect. To solve this problem, attempts have been made to chemically modify bio-related substances with sugar chain, hydrophilic polymers such as polyethylene glycol, albumin and the like. As a result, it becomes possible to prolong the blood half-life of bio-related substances by increasing the molecular weight, forming a hydration layer, and the like. In addition, it is also well known that modification with polyethylene glycol provides effects such as reduction of toxicity and antigenicity of bio-related substances, and improvement of solubility of hardly water-soluble drugs.

The bio-related substances modified with polyethylene glycol are covered with a hydration layer formed by an ether bond of polyethylene glycol and a hydrogen bond with water molecule, has an increased molecular size, and thus can avoid glomerular filtration in the kidney. Furthermore, it is known that the interaction with opsonin and the cell surface that constitutes each tissue decreases, and the migration to each tissue decreases. Polyethylene glycol is a superior material that extends the blood half-life of bio-related substances, and it has been found as regards the property thereof that a higher effect is obtained when the molecular weight is higher. Many studies have been made on bio-related substances modified with high-molecular-weight polyethylene glycol with a molecular weight of not less than 40,000, and the results show that the half-life in blood thereof can be significantly extended.

Polyethylene glycol is regarded as the optimum standard among the modified preparations used for improving the property of bio-related substances. At present, a plurality of polyethylene glycol modified formulations is placed on the market and used in medical sites. On the other hand, the European Medicines Agency (EMA) reported in 2012 that administration of a bio-related substance modified with high-molecular-weight polyethylene glycol with a molecular weight of 40,000 or more to an animal for a long time at a certain dose or above led to a phenomenon of the generation of vacuoles in the cells of a part of the tissues (non-patent document 1). In consideration of the facts that there is no report at present that the vacuole formation itself has an adverse effect on the human body, and the dose used in the above EMA report is extremely high compared to the dose generally applied in medical sites, the safety of therapeutic preparations modified with polyethylene glycol having a molecular weight of 40,000 or more which are currently manufactured and sold does not pose any problem. However, in the treatment of very special diseases (for example, dwarfism), it may be assumed that a treatment protocol in which a polyethylene glycol-modified preparation is administered to a patient at a high dose for a long period of time will be adopted. Therefore, it is expected that a potential demand exists for the development of a polyethylene glycol-modified preparation that does not cause vacuole formation in cells and can be applied even in such a special situation.

In non-patent document 2, a large excess of polyethylene glycol alone was administered to animals for a long term compared to the dose of general polyethylene glycol-modified preparations. As a result, vacuole was not seen at a molecular weight of 20,000, and the generation of vacuole was confirmed at a molecular weight of 40,000. One of the means to suppress vacuoles is to reduce the molecular weight of polyethylene glycol. However, reducing the molecular weight causes a problem that the half-life in blood of bio-related substances cannot be improved sufficiently.

There are reports relating to the technique for degrading high-molecular-weight polyethylene glycol into low-molecular-weight polyethylene glycol in the body and promoting excretion from the kidney.

Patent document 1 describes a polyethylene glycol derivative having a sulfide bond or peptide binding site that is cleaved in vivo. It is described that the polyethylene glycol derivative is degraded in vivo to a molecular weight suitable for excretion from the kidney. However, no specific data relating to the degradation is shown, nor is there any data on enhanced excretion from the kidney. Furthermore, there is no description about the vacuoles in cells.

Patent document 2 describes a polyethylene glycol derivative having an acetal site that can be hydrolyzed under low pH environment in the body. It is described that the polyethylene glycol derivative is degraded in vivo to a molecular weight suitable for excretion from the kidney. However, no specific data on enhanced excretion from the kidney is shown. Furthermore, there is no description about the vacuoles in cells. In addition, the hydrolyzable acetal moiety is known to gradually degrade also in blood, and it is expected that the half-life in blood of modified bio-related substances cannot be improved sufficiently.

On the other hand, there are reports on polyethylene glycol derivatives containing degradable oligopeptides introduced thereinto for effective release of drugs, hydrogels that degrade in the body, and the like.

Non-patent document 3 describes a polyethylene glycol derivative having an oligopeptide site that is degraded by enzymes. Here, the oligopeptide was introduced as a linker between an anticancer agent and polyethylene glycol, and it has been reported that the oligopeptide is degraded by the enzyme specifically expressed around the tumor, and the anticancer agent is efficiently released. The purpose is release of an anticancer agent, and the degradability is not imparted to polyethylene glycol for the purpose of suppressing cell vacuoles.

Non-patent document 4 describes hydrogels using cross-linked molecules having an oligopeptide site that is degraded by enzymes and a multi-branched polyethylene glycol derivative. Here, the oligopeptide is used as a cross-linking molecule that connects the multi-branched polyethylene glycol derivative, and can further impart degradability by enzymes to the hydrogel. It aims to prepare a degradable hydrogel, where the degradability is not imparted to polyethylene glycol for the purpose of suppressing cell vacuoles.

Patent document 3 describes a branched polyethylene glycol derivative with oligopeptide as the skeleton. Here, oligopeptide is used as the basic skeleton of polyethylene glycol derivatives and does not impart degradability by enzymes. It is characterized by containing amino acids having an amino group or a carboxyl group in the side chain, such as lysine and aspartic acid, in the oligopeptide, and aims to synthesize a branched polyethylene glycol derivative by utilizing them in the reaction. Patent document 3 is not directed to a polyethylene glycol derivative for the purpose of suppressing cell vacuoles.

Polyethylene glycol derivatives used for modifying bio-related substances generally include a linear type and a branched type. Non-patent document 5 describes that the branched type, rather than the linear type, significantly prolongs the half-life in blood of bio-related substances. In recent years, most of the polyethylene glycol-modified preparations on the market adopt the branched type. However, there have been no reports on a bio-related substance modified by a branched polyethylene glycol derivative that suppresses cell vacuoles in the pertinent field.

As described above, a bio-related substance modified by a branched, high-molecular-weight polyethylene glycol derivative that is stable in blood, can improve half-life in blood of the modified bio-related substance, is specifically degraded in cell, and can suppress generation of vacuoles in cells is demanded.

DOCUMENT LIST

Patent Documents patent document 1: Japanese Translation of PCT Application Publication No. 2009-527581
patent document 2: WO 2005/108463
patent document 3: WO 2006/088248

Non-Patent Documents non-patent document 1: EMA/CHMP/SWP/647258/2012
non-patent document 2: Daniel G. Rudmann, et al., Toxicol. Pathol., 41, 970-983(2013)
non-patent document 3: Francesco M Veronese, et al., Bioconjugate Chem., 16, 775-784(2005)
non-patent document 4: Jiyuan Yang, et al., Marcomol. Biosci., 10(4), 445-454(2010)
non-patent document 5: Yulia Vugmeysterang, et al., Bioconjugate Chem., 23, 1452-1462(2012)

SUMMARY OF INVENTION

Technical Problem

The problem of the present invention is to provide a bio-related substance bonded to a branched, high-molecular-weight polyethylene glycol derivative that does not cause vacuolation of cells. More specifically, it is to provide a bio-related substance with improved half-life in blood that is stable in the blood of living organisms, and modified by a branched, degradable polyethylene glycol derivative that is degraded in cells.

Solution to Problem

The present inventors have conducted intensive studies in an attempt to solve the aforementioned problems and invented a bio-related substance bonded to a branched and degradable polyethylene glycol derivative having an oligopeptide that degrades in cells.

Accordingly, the present invention provides the following.

[1] A degradable polyethylene glycol derivative-bonded bio-related substance represented by the following formula (A):

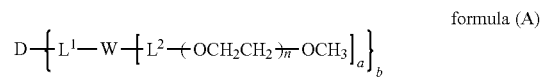

formula (A)

wherein n is 45-950, W is an oligopeptide consisting of 5 to 47 residues and having a symmetrical structure centered on glutamic acid, a is 2-8, D is a bio-related substance, $L^1$ and $L^2$ are each independently a divalent spacer, and b is 1-40.

[2] A degradable polyethylene glycol derivative-bonded bio-related substance represented by the following formula (1):

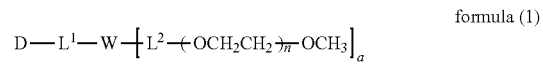

formula (1)

wherein n is 45-950, W is an oligopeptide consisting of 5 to 47 residues and having a symmetrical structure centered on glutamic acid, a is 2-8, D is a bio-related substance, and $L^1$ and $L^2$ are each independently a divalent spacer.

[3] The bio-related substance of [1] or [2], wherein the oligopeptide for W with a symmetrical structure centered on glutamic acid is an oligopeptide having the following structure of w1, w2 or w3:

(w1)

(w2)

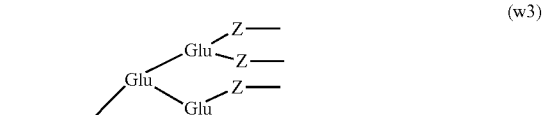

(w3)

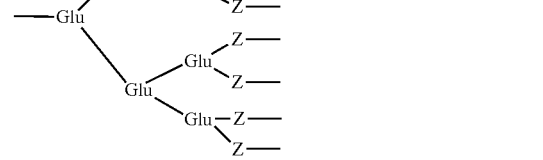

wherein Glu is a glutamic acid residue, and Z is a degradable oligopeptide of 2-5 residues consisting of neutral amino acids excluding cysteine.

[4] The bio-related substance of [3], wherein the degradable oligopeptide for Z is an oligopeptide having glycine as C-terminal amino acid.

[5] The bio-related substance of [3] or [4], wherein the degradable oligopeptide for Z is an oligopeptide having at least one hydrophobic neutral amino acid having a hydropathy index of not less than 2.5.

[6] The bio-related substance of any one of [1] to [5], wherein a molecular weight of one molecule of the degradable polyethylene glycol derivative is not less than 20,000.
[7] The bio-related substance of any one of [1] to [6], wherein $L^1$ is a urethane bond, an amide bond, an ether bond, a thioether bond, a secondary amino group, a carbonyl group, a urea bond, a triazolyl group, a bond of maleimide and mercapto, or an oxime bond; or an alkylene group optionally comprising such bond and/or group.
[8] The bio-related substance of any of [1] to [7], wherein $L^2$ is an alkylene group; or an alkylene group comprising at least one bond and/or group selected from a urethane bond, an amide bond, an ether bond, a thioether bond, a secondary amino group, a carbonyl group, and a urea bond.
[9] The bio-related substance of any of [1] to [8], wherein the bio-related substance for D is a hormone, a cytokine, an antibody, an aptamer or an enzyme.

Advantageous Effects of Invention

The bio-related substance of the present invention is modified by a branched and degradable polyethylene glycol derivative having, in its structure, an oligopeptide which is stable in blood in the body and degraded by intracellular enzymes. Therefore, the bio-related substance is stable in blood and has a half-life in blood that is equivalent to that of a bio-related substance modified by a conventional polyethylene glycol derivatives without degradability. Furthermore, when the bio-related substance is incorporated into cells, the oligopeptide site of the degradable polyethylene glycol derivative is rapidly degraded, thus suppressing the generation of vacuoles in cells which has been a problem to date. The oligopeptide constituting the degradable polyethylene glycol derivative has a symmetrical structure centered on glutamic acid, and the same degradable oligopeptide Z is bonded to the ends of all polyethylene glycol chains. Therefore, the polyethylene glycol degradation products generated during intracellular degradation have the same molecular weight and the same structure, and characteristically show uniform discharge from tissues and cells.

DESCRIPTION OF EMBODIMENTS

Figure 1:
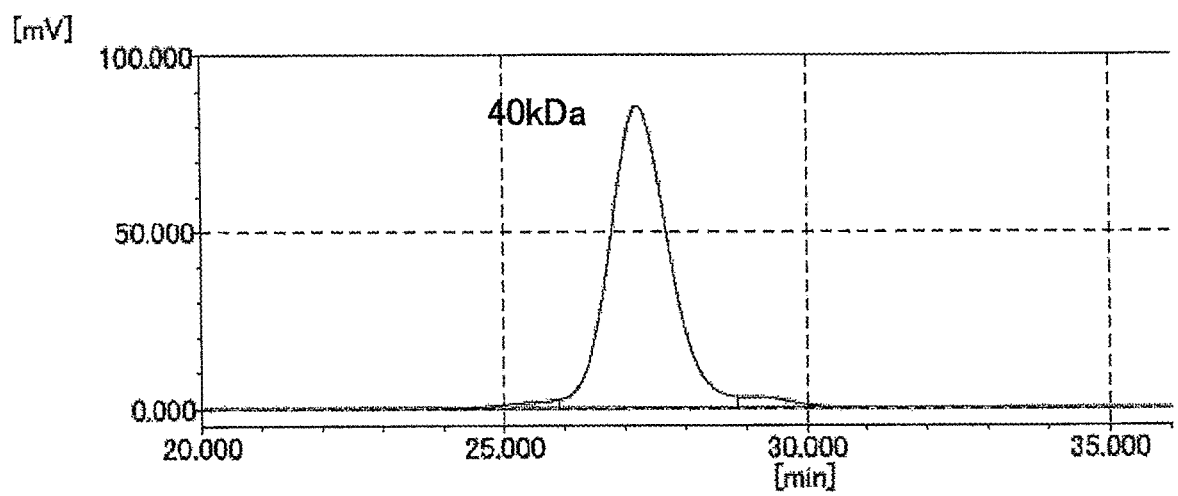
FIG. 1 shows GPC analysis results of the compound (p3) (NH$_2$-E(FG-200ME)$_2$) of Example 1.
Figure 2:
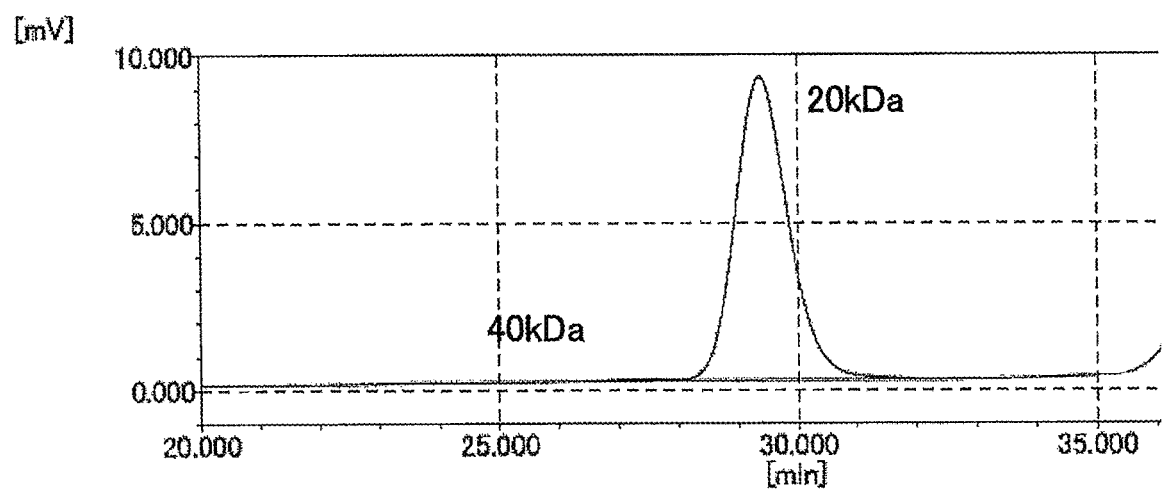
FIG. 2 shows GPC analysis results of the compound (p3) (NH$_2$-E(FG-200ME)$_2$) recovered from inside the cell in the degradability test using the cells in Example 8.
Figure 3:
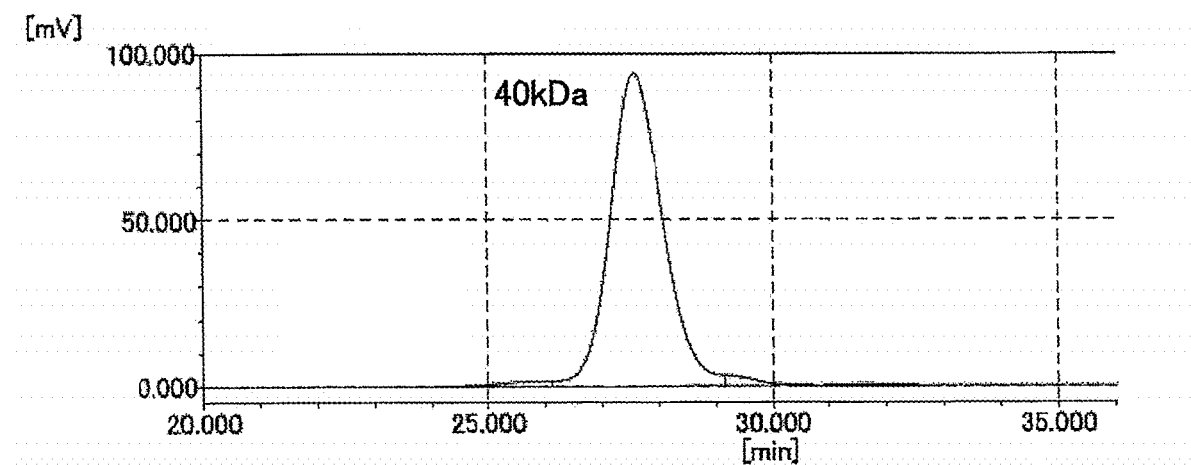
FIG. 3 shows GPC analysis results of the compound (p13) (NH$_2$-E{E (FG-100ME)$_2$}$_2$) of Example 5.
Figure 4:
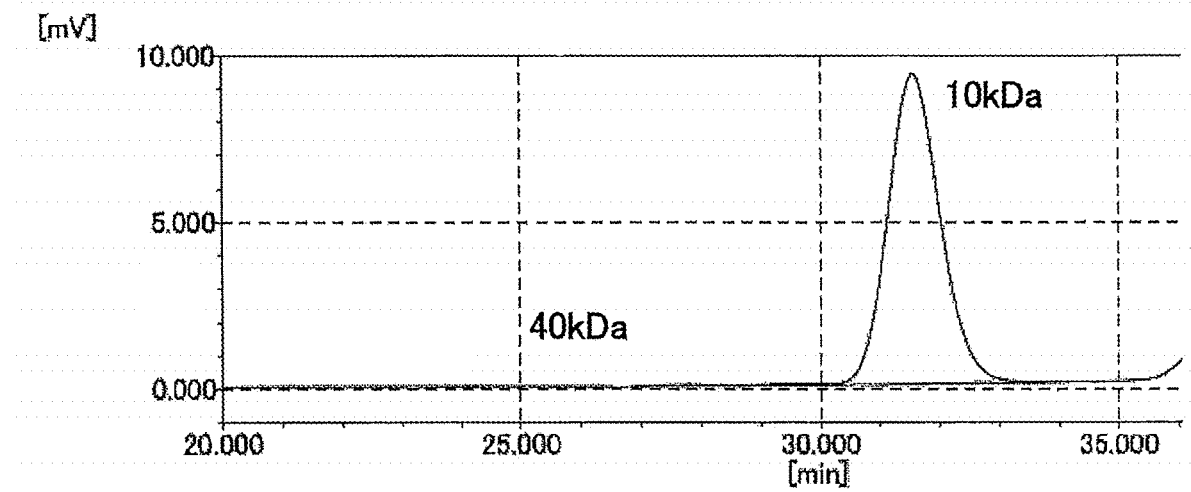
FIG. 4 shows GPC analysis results of the compound (p13) (NH$_2$-E{E(FG-100ME)$_2$}$_2$) recovered from inside the cell in the degradability test using the cells in Example 8.

The present invention is explained in detail in the following.
The degradable polyethylene glycol derivative-bonded bio-related substance of the present invention is represented by the following formula (A).

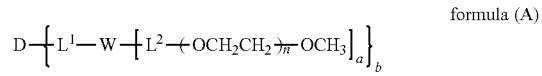

formula (A)

wherein n is 45-950, W is an oligopeptide consisting of 5 to 47 residues and having a symmetrical structure centered on glutamic acid, a is 2-8, D is a bio-related substance, $L^1$ and $L^2$ are each independently a divalent spacer, and b is 1-40.

The molecular weight of one molecule of the polyethylene glycol derivative bonded to the bio-related substance of the formula (A) of the present invention is generally 4,000-160,000, preferably 10,000-120,000, further preferably 20,000-80,000. In one preferred embodiment of the present invention, the molecular weight of one molecule of the polyethylene glycol derivative of the formula (A) of the present invention is not less than 20,000. The molecular weight here is a number average molecular weight (Mn).

In the formula (A), n is a repeating unit number of polyethylene glycol. It is generally 45-950, preferably 110-690, further preferably 220-460.

In the formula (A), a shows the number of polyethylene glycol chains bonded to oligopeptide. It is generally 2-8, preferably 2 or 4 or 8, further preferably 2 or 4.

In the formula (A), b shows the number of molecules of a degradable polyethylene glycol derivative bonded to a bio-related substance. It is generally 1-40, preferably 1-20, further preferably 1-10.

By increasing the number of molecules of the polyethylene glycol derivative bonded to a bio-related substance, effects such as extended half-life in blood, reduced antigenicity and the like are afforded. However, the activity may be reduced depending on the bio-related substance. On the other hand, it is known that the activity of bio-related substances such as a part of enzymes does not decrease even when a plurality of polyethylene glycol derivatives are bonded.

In the formula (A), $L^1$ and $L^2$ are each independently a divalent spacer. These spacers are not particularly limited as long as they are groups capable of forming a covalent bond. $L^1$ is preferably amide bond, ether bond, thioether bond, urethane bond, secondary amino group, carbonyl group, urea bond, triazolyl group, a bond of maleimide and mercapto, or oxime bond; or alkylene group optionally containing such bond and/or group.

$L^2$ is preferably an alkylene group; or an alkylene group containing at least one bond and/or group selected from amide bond, ether bond, thioether bond, urethane bond, secondary amino group, carbonyl group, and urea bond. $L_2$ is preferably bonded to the repeating unit of polyethylene glycol via a carbon atom.

Particularly preferred embodiments of $L^1$ and $L^2$ are shown in the following Group (I). Two to five spacers of Group (I) may be used in combination. An ester bond and a carbonate bond are not suitable as the divalent spacers since they are gradually degraded in the blood of living organisms.

Group (I):

(z1)

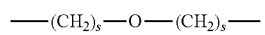
(z2)

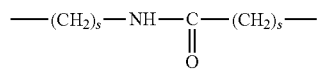
(z3)

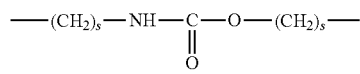
(z4)

(z5)

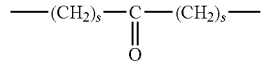
(z6)

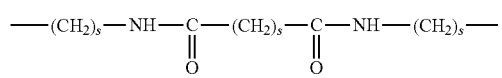
(z7)

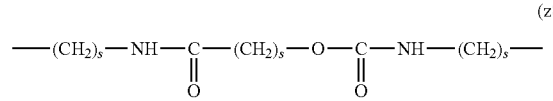
(z8)

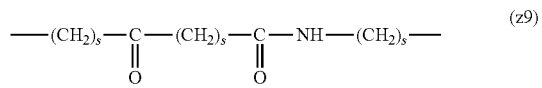
(z9)

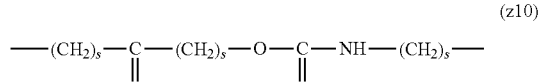
(z10)

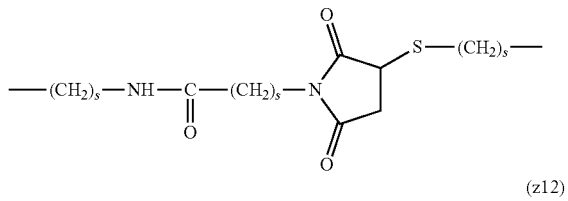
(z11)

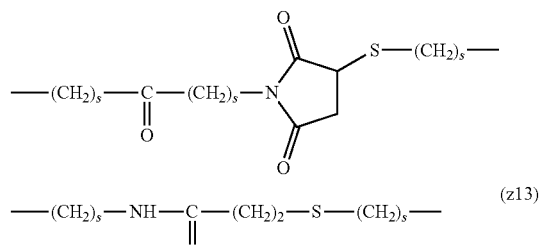
(z12)

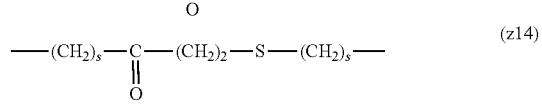
(z13)

(z14)

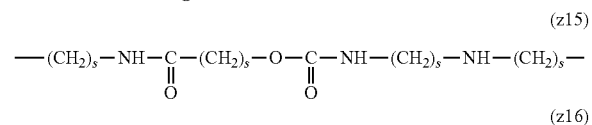
(z15)

(z16)

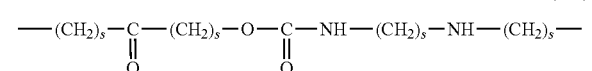
(z17)

(z18)

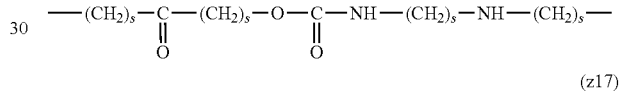
(z19)

(z20)

In (z1)-(z20), s is an integer of 0-10, preferably an integer of 0-6, further preferably an integer of 0-3. In (z2)-(z20), each s may be the same or different. When $L^1$ is an asymmetric divalent spacer, the bonding position with other adjacent groups is not particularly limited and it can take both coupling positions of the right side of the spacer represented by the aforementioned formula in the above-mentioned Group (I) indicating the bonding position with W, and the left side indicating the bonding position with D; and the left side indicating the bonding position with W, and the right side indicating the bonding position with D. Similarly, when $L^2$ is an asymmetric divalent spacer, the right side of the spacer represented by the aforementioned formula in the above-mentioned Group (I) may indicate the bonding position with $OCH_2CH_2$ and the left side may indicate the bonding position with W; or the left side may indicate the bonding position with $OCH_2CH_2$ and the right side may indicate the bonding position with W.

L¹ in the formula (A) is preferably a group represented by (z3), (z6), (z7)-(z20) in Group (I), more preferably a group represented by (z6), (z9), (z10), (z12), (z14), (z16), (z18) or (z20) in Group (I), further preferably a group represented by (z10), (z12), (z16) or (z20) in Group (I).

L² in the formula (A) is preferably a group represented by (z1), (z2), (z3), (z4), (z5), (z6), (z7) or (z8) in Group (I), more preferably a group represented by (z3) or (z5) in Group (I).

W in the formula (A) is an oligopeptide of 5-47 residues having a symmetrical structure centered on glutamic acid, and is not particularly limited as long as it is an oligopeptide stable in the blood of living organisms and degraded by enzyme in cells. The amino acid constituting the oligopeptide preferably consists of neutral amino acid excluding cysteine, except for glutamic acid constituting the central portion. As used herein, the oligopeptide having a symmetrical structure centered on glutamic acid means a compound in which the same peptide is bonded to the α-position carboxyl group and the γ-position carboxyl group of glutamic acid, and is an oligopeptide in which paired peptides centered on glutamic acid have a symmetrical structure. The composition ratio of the number of neutral amino acids and glutamic acids in the oligopeptide (number of neutral amino acids/number of glutamic acids) is generally 2-10, preferably 2-8, further preferably 2-6. The amino acid constituting W is basically of an L type.

Particularly preferred embodiments of W are shown in the following Group (II).
Group (II):

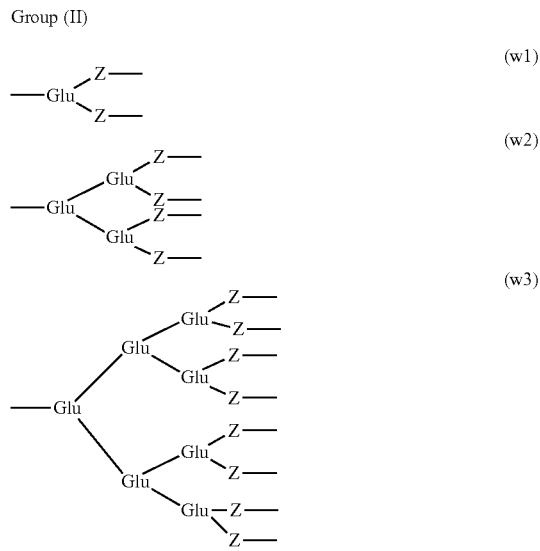

wherein Glu is a glutamic acid residue, and Z is a degradable oligopeptide of 2-5 residues consisting of neutral amino acids excluding cysteine.

In (w1)-(w3), Z is preferably an oligopeptide composed of an amino acid having an amino group and a carboxyl group in the side chain, specifically, neutral amino acids not including lysine, aspartic acid, or glutamic acid. In the synthesis of the branched and degradable polyethylene glycol derivative of the formula (A) of the present invention, the C-terminal carboxyl group of oligopeptide is utilized for the condensation reaction with a polyethylene glycol derivative when the polyethylene glycol derivative as a starting material is bonded to the oligopeptide by reaction. However, when the oligopeptide has an amino acid having an amino group or a carboxyl group in the side chain, a side reaction between the oligopeptides, and impurities in which the polyethylene glycol derivative is introduced into the side chain carboxyl group rather than the desired C-terminal carboxyl group are developed as a result of the condensation reaction.

Since this impurity is difficult to remove by a purification step such as general extraction or crystallization, to obtain the desired product with high purity, it is desirable to use an oligopeptide composed of amino acids having no amino group or carboxyl group in the side chain. The amino acid constituting Z is α-amino acid and is basically in the L form.

Cysteine, which is a neutral amino acid, has a mercapto group and forms a disulfide bond with other mercapto groups. Thus, in (w1)-(w3), Z is desirably an oligopeptide composed of neutral amino acids not including cysteine.

In (w1)-(w3), moreover, Z is preferably an oligopeptide having glycine as the C-terminal amino acid. When a C-terminal carboxyl group is reacted with a polyethylene glycol derivative, it is basically necessary to activate the C-terminal carboxyl group with a condensing agent and the like. It is known that epimerization tends to occur in amino acids other than glycine and stereoisomer is by-produced in this activation step. By using an achiral glycine as the C-terminal amino acid of the oligopeptide, a highly pure target product free from by-production of stereoisomer can be obtained.

In (w1)-(w3), moreover, Z is preferably a hydrophobic neutral amino acid having a hydropathy index of not less than 2.5, specifically, an oligopeptide having at least one of phenylalanine, leucine, valine, and isoleucine, more preferably an oligopeptide having phenylalanine. The hydropathic index (hydropathy index) created by Kyte and Doolittle that quantitatively indicates the hydrophobicity of amino acid shows that the larger the value, the more hydrophobic the amino acid (Kyte J & Doolittle R F, 1982, J Mol Biol, 157:105-132).

In (w1)-(w3), Z is not particularly limited as long as it is an oligopeptide with 2-5 residues composed of neutral amino acids excluding cysteine, is stable in the blood of living organisms, and has property of degradation by an enzyme in cells. Specific examples include glycine-phenylalanine-leucine-glycine (SEQ ID NO: 4), glycine-glycine-phenylalanine-glycine (SEQ ID NO: 5), glycine-phenylalanine-glycine, glycine-leucine-glycine, valine-citrulline-glycine, valine-alanine-glycine, phenylalanine-glycine and the like, preferably glycine-phenylalanine-leucine-glycine, glycine-glycine-phenylalanine-glycine, glycine-phenylalanine-glycine, valine-citrulline-glycine, valine-alanine-glycine, or phenylalanine-glycine, more preferably glycine-phenylalanine-leucine-glycine (SEQ ID NO: 4), glycine-phenylalanine-glycine, valine-citrulline-glycine, or phenylalanine-glycine, further more preferably glycine-phenylalanine-leucine-glycine (SEQ ID NO: 4), or phenylalanine-glycine.

D in the formula (A) is a bio-related substance and is not particularly limited. It is a substance related to diagnosis, cure, alleviation, treatment or prophylaxis of diseases in human or other animals. Specifically, it includes proteins, peptides, nucleic acids, cells, viruses and the like, and suitable protein or peptide includes hormones, cytokines, antibodies, aptamers, enzymes and the like.

More specifically, cytokine includes interferon type I, type II, type III, interleukin, tumor necrosis factor, receptor antagonist thereof, and the like that regulate immunity. The growth factor includes erythropoietin, which is a hematopoietic factor, granulocyte colony-stimulating factor (GCSF), which is a stimulating factor, and the like. The blood coagulation factor includes factor V, factor VII, factor VIII, factor IX, factor X, factor XII and the like. The hormone includes calcitonin, insulin, analog thereof, exenatide, GLP-1, somatostatin, human growth hormone, and the like. The antibody includes full-length antibody, and Fab and svFV as antibody fragments; the aptamer includes DNA aptamer, RNA aptamer and the like; and the enzyme includes superoxide dismutase, uricase and the like. These proteins have low stability in blood and are desirably modified with polyethylene glycol to prolong their half-life in blood.

Preferred proteins include interferon, interleukin, erythropoietin, GCSF, factor VIII, factor IX, human growth hormone, antibody fragment and the like. Human growth hormone, interferon, GCSF, erythropoietin or antibody fragment (particularly Fab) is more preferred, and human growth hormone GCSF is further preferred.

Preferred peptides include insulin, bivalirudin, teriparatide, exenatide, enfuvirtide, degarelix, mifamultide, nesiritide, goserelin, glatiramer, octreotide, lanreotide, icatibant, dicotinide, pramlintide, romiprostim, calcitonin, oxytocin, leuprorelin, and glucagon. More preferred are insulin, exenatide, and calcitonin (particularly salmon calcitonin).

One of the preferred embodiments of the bio-related substance represented by the formula (A) is a bio-related substance represented by the following formula (1) wherein b is 1.

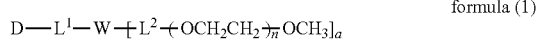

formula (1)

wherein n, W, a, D, $L^1$ and $L^2$ are each as defined above.

One of the preferred embodiments of the formula (1) is a bio-related substance represented by the following formula (2) wherein W is w1 and a=2.

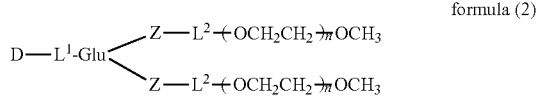

formula (2)

wherein Glu, Z, n, D, $L^1$ and $L^2$ are as defined above.

One of the preferred embodiments of the formula (1) is a bio-related substance represented by the following formula (3) wherein W is w2 and a=4.

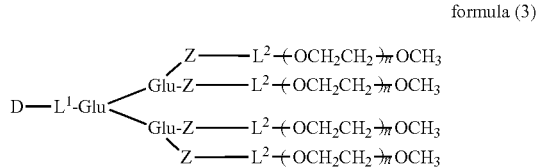

formula (3)

wherein Glu, Z, n, D, $L^1$ and $L^2$ are as defined above.

One of the preferred embodiments of the formula (1) is a bio-related substance represented by the following formula (4) wherein W is w3 and a=8.

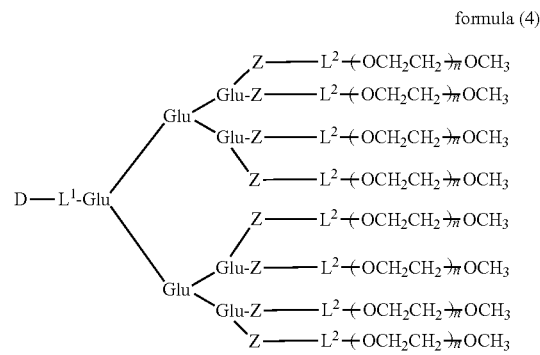

formula (4)

wherein Glu, Z, n, D, $L^1$ and $L^2$ are as defined above.

The bio-related substance of the formula (A) of the present invention can be obtained by reacting a degradable polyethylene glycol derivative represented by the following formula (5) and a bio-related substance.

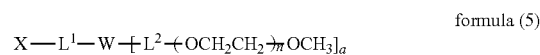

formula (5)

wherein X is a functional group that can react with a bio-related substance, and W, a, n, $L^1$ and $L^2$ are as defined above.

In the formula (5), X is not particularly limited as long as it is a functional group that reacts with a functional group present in bio-related substances such as a physiologically active protein, peptide, antibody, or nucleic acid to be chemically modified to form a covalent bond. For example, the functional groups described in "Harris, J. M. Poly (Ethylene Glycol) Chemistry; Plenum Press: New York, 1992", "Hermanson, G. T. Bioconjugate Techniques, 2nd ed.; Academic Press: San Diego, CA, 2008" and "PEGylated Protein Drugs: Basic Science and Clinical Applications; Veronese, F. M., Ed.; Birkhauser: Basel, Switzerland, 2009" and the like can be mentioned.

In the formula (5), the "functional group capable of reacting with a bio-related substance" for X is not particularly limited as long as it is a functional group that can be chemically bonded to a functional group of a bio-related substance such as such as amino group, mercapto group, aldehyde group, carboxyl group, unsaturated bond or azide group and the like.

Specifically, active ester group, active carbonate group, aldehyde group, isocyanate group, isothiocyanate group, epoxide group, carboxyl group, mercapto group, maleimide group, substituted maleimide group, hydrazide group, pyridyldithio group, substituted sulfonate group, vinylsulfonyl group, amino group, oxyamino group ($H_2N$—O— group), iodoacetamide group, alkylcarbonyl group, alkenyl group (e.g., allyl group, vinyl group), alkynyl group, substituted alkynyl group (e.g., alkynyl group substituted by hydrocarbon group with carbon number of 1-5 to be described later), azide group, acrylic group, sulfonyloxy group (e.g., alkylsulfonyloxy group), α-halo acetyl group and the like can be mentioned. It is preferably active ester group, active carbonate group, aldehyde group, isocyanate group, isothiocyanate group, epoxide group, maleimide group, substituted maleimide group, vinylsulfonyl group, acrylic group, sulfonyloxy group (e.g., alkyl-sulfonyloxy group with carbon number of 1-5), substituted sulfonate group, carboxyl group, mercapto group, pyridyldithio group, α-halo acetyl group, alkynyl group, substituted alkynyl group (e.g., alkynyl group with carbon number of 2-5 and substituted by hydrocarbon group with carbon number of 1-5 to be described later), allyl group, vinyl group, amino group, oxyamino group, hydrazide group or azide group, more preferably active ester group, active carbonate group, aldehyde group, maleimide group, oxyamino group or amino group, particularly preferably aldehyde group, maleimide group or oxyamino group.

In another preferred embodiment, the functional group X can be classified into the following Group (III), Group (IV), Group (V), Group (VI), Group (VII) and Group (VIII).

Group (III): functional group capable of reacting with amino group of bio-related substance The groups represented by the following (a), (b), (c), (d), (e), (f), (g), (j) and (k) can be mentioned.

Group (IV): functional group capable of reacting with mercapto group of bio-related substance The groups represented by the following (a), (b), (c), (d), (e), (f), (g), (h), (i), (j), (k) and (l) can be mentioned.

Group (V): functional group capable of reacting with aldehyde group of bio-related substance The groups represented by the following (h), (m), (n) and (p) can be mentioned.

Group (VI): functional group capable of reacting with carboxyl group of bio-related substance The groups represented by the following (h), (m), (n) and (p) can be mentioned.

Group (VII): functional group capable of reacting with unsaturated bond of bio-related substance The groups represented by the following (h), (m) and (o) can be mentioned.

Group (VIII): functional group capable of reacting with azide group of bio-related substance The group represented by the following (l) can be mentioned.

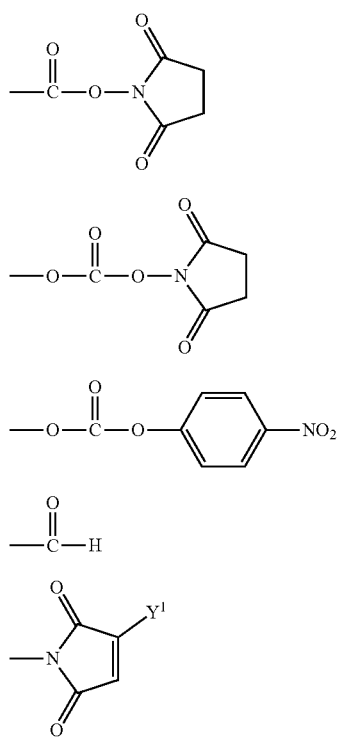

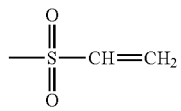

(f)

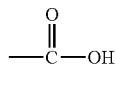

(g)

—SH (h)

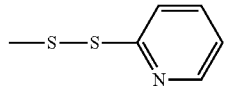

(i)

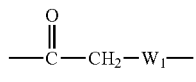

(j)

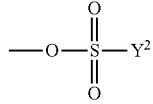

(k)

(l)

—NH$_2$ (m)

—ONH$_2$ (n)

—N$_3$ (o)

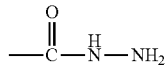

(p)

In functional group (j), W$_1$ is a halogen atom such as a chlorine atom (Cl), a bromine atom (Br) or an iodine atom (I), preferably Br or I, more preferably I.

In functional group (e) and functional group (l), Y$^1$ and Y$^3$ are each independently a hydrogen atom or a hydrocarbon group having 1 to 5 carbon atoms, preferably a hydrocarbon group having 1 to 5 carbon atoms. Specific examples of the hydrocarbon group having 1 to 5 carbon atoms include a methyl group, an ethyl group, a propyl group, an isopropyl group, a butyl group, a tertiary butyl group and the like, preferably a methyl group or an ethyl group.

In functional group (k), Y$^2$ is a hydrocarbon group having 1-10 carbon atoms and optionally containing a fluorine atom. Specifically, it is a methyl group, an ethyl group, a propyl group, an isopropyl group, a butyl group, a tertiary butyl group, a hexyl group, a nonyl group, a vinyl group, a phenyl group, a benzyl group, a 4-methylphenyl group, a trifluoromethyl group, a 2,2,2-trifluoroethyl group, a 4-(trifluoromethoxy)phenyl group or the like, preferably a methyl group, a vinyl group, a 4-methylphenyl group, or a 2,2,2-trifluoroethyl group.

The active ester group is an ester group having an alkoxy group with high elimination ability. As the alkoxy group with high elimination ability, an alkoxy group induced from nitrophenol, N-hydroxysuccinimide, pentafluorophenol and the like can be mentioned. The active ester group is preferably an ester group having an alkoxy group induced from N-hydroxysuccinimide.

The active carbonate group is a carbonate group having an alkoxy group with high elimination ability. As the alkoxy group with high elimination ability, an alkoxy group induced from nitrophenol, N-hydroxysuccinimide, pentafluorophenol and the like can be mentioned. The active carbonate group is preferably a carbonate group having an alkoxy group induced from nitrophenol or N-hydroxysuccinimide.

The substituted maleimide group is a maleimide group in which a hydrocarbon group is bonded to one carbon atom of the double bond of the maleimide group. The hydrocarbon group is specifically a methyl group, an ethyl group, a propyl group, an isopropyl group, a butyl group, a tertiary butyl group and the like, preferably a methyl group or an ethyl group.

The substituted sulfonate group is a sulfonate group in which a hydrocarbon group which may contain a fluorine atom is bonded to a sulfur atom of the sulfonate group. As the hydrocarbon group which may contain a fluorine atom, specifically, a methyl group, an ethyl group, a propyl group, an isopropyl group, a butyl group, a tertiary butyl group, a hexyl group, a nonyl group, a vinyl group, a phenyl group, a benzyl group, a 4-methylphenyl group, a trifluoromethyl group, a 2,2,2-trifluoroethyl group, a 4-(trifluoromethoxy) phenyl group and the like can be mentioned. It is preferably a methyl group, a vinyl group, a 4-methylphenyl group, or a 2,2,2-trifluoroethyl group.

The branched and degradable polyethylene glycol derivative to be used for the bio-related substance of the present invention can be produced, for example, by the following step.

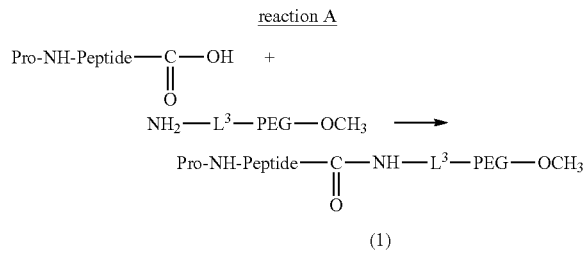

(PEG in the step is a polyethylene glycol chain, Peptide is an oligopeptide, Pro is a protecting group, and $L^3$ is a divalent spacer.)

PEG in the step is a polyethylene glycol chain, and the molecular weight thereof is as defined for the aforementioned n as the number of repeating units of polyethylene glycol, namely, since n is 45-950, the molecular weight thereof is within the range of 2000-42000.

Peptide in the step is an oligopeptide defined for the aforementioned Z. In this step, an oligopeptide in which the N-terminal amino group is protected by a protecting group is used.

Pro in the step is a protecting group. A protecting group here is a component that prevents or inhibits the reaction of a particular chemically reactive functional group in a molecule under certain reaction conditions. Protecting groups vary depending on the kind of chemically reactive functional group to be protected, the conditions to be used and the presence of other functional group or protecting group in the molecule. Specific examples of the protecting group can be found in many general books, and they are described in, for example, "Wuts, P. G. M.; Greene, T. W. Protective Groups in Organic Synthesis, 4th ed.; Wiley-Interscience: New York, 2007". The functional group protected by a protecting group can be deprotected, that is, chemically reacted, using a reaction condition suitable for each protecting group, whereby the original functional group can be regenerated. Representative deprotection conditions for protecting groups are described in the aforementioned literature.

In the step, $L^3$ is the same divalent spacer as in the aforementioned $L^1$, and $L^2$.

Reaction A is a process for bonding a carboxyl group of oligopeptide with the N-terminal amino group protected by a protecting group with an amino group of a polyethylene glycol derivative having a methoxy group at one terminal by a condensation reaction to give polyethylene glycol derivative (1).

The protecting group of the N-terminal amino group of oligopeptide is not particularly limited. For example, acyl protecting group and carbamate protecting group can be mentioned, and a trifluoroacetyl group, a 9-fluorenyl methyloxycarbonyl group (Fmoc), a tert-butyloxycarbonyl group and the like can be specifically mentioned.

The condensation reaction is not particularly limited, and a reaction using a condensing agent is desirable. As the condensing agent, a carbodiimide condensing agent such as dicyclohexylcarbodiimide (DCC), 1-ethyl-3-(3-dimethylaminopropyl)carbodiimide hydrochloride (EDC) or the like may be used alone, or it may be used in combination with a reagent such as N-hydroxysuccinimide (NHS), 1-hydroxybenzotriazole (HOBt), 1-hydroxy-7-azabenzotriazole (HOAt) and the like. Also, a condensing agent with higher reactivity such as HATU, HBTU, TATU, TBTU, COMU, DMT-MM and the like may be used. To promote the reaction, a base such as triethylamine, dimethylaminopyridine and the like may also be used.

Impurities by-produced in the reaction, or oligopeptides and condensing agents which were not consumed and remain in the reaction are preferably removed by purification. The purification is not particularly limited, and extraction, recrystallization, adsorption treatment, reprecipitation, column chromatography, supercritical extraction, and the like can be used for purification.

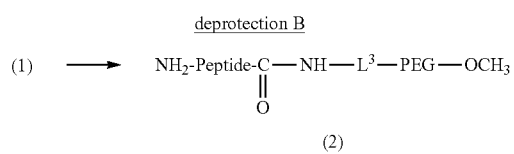

Deprotection B is a process for removing the protecting group of polyethylene glycol derivative (1) obtained in reaction A to give polyethylene glycol derivative (2). For the deprotection reaction, a conventionally-known method can be used. It is necessary to use conditions that do not cause degradation of oligopeptide and divalent spacer for $L^3$. This step can also be performed as a part of the step of reaction A.

Impurities and the like by-produced in the deprotection reaction are preferably removed by purification. The purification is not particularly limited, and extraction, recrystallization, adsorption treatment, reprecipitation, column chromatography, supercritical extraction, and the like can be used for purification.

reaction C

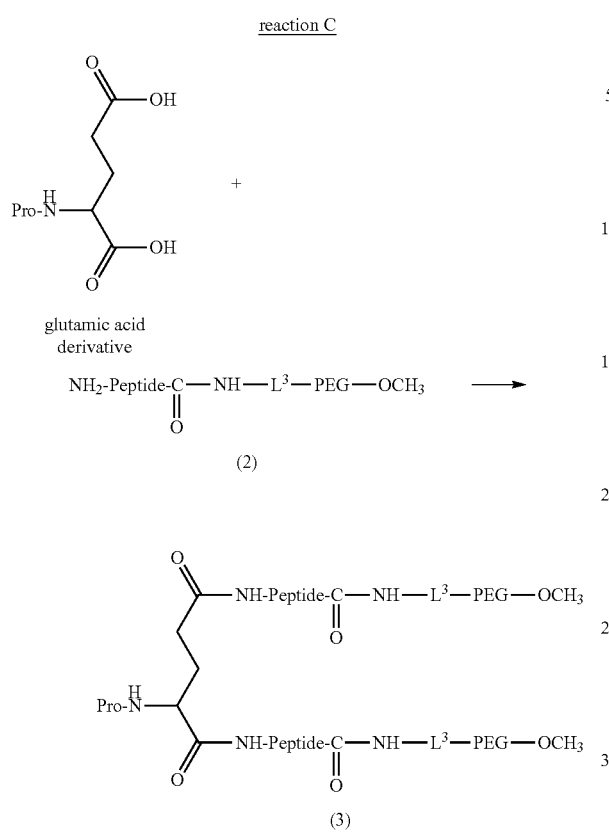

(2)

(3)

In reaction C, the amino group of the polyethylene glycol derivative (2) obtained in deprotection B and the two carboxyl groups of the glutamic acid derivative whose amino group is protected by a protecting group are bonded by a condensation reaction to give the branched polyethylene glycol derivative (3) having a structure in which two degradable polyethylene glycol chains are connected by a glutamic acid residue.

Similar to the aforementioned reaction A, a reaction using a condensing agent is desirable and, to promote the reaction, a base such as triethylamine, dimethylaminopyridine and the like may also be used.

The protecting group of amino group of glutamic acid is not particularly limited and, for example, an acyl protecting group and a carbamate protecting group can be mentioned, and a trifluoroacetyl group, a 9-fluorenyl methyloxycarbonyl group (Fmoc), a tert-butyloxycarbonyl group and the like can be specifically mentioned.

Impurities by-produced in the reaction, or polyethylene glycol derivative and the like which were not consumed and remain in the reaction are preferably removed by purification. The purification is not particularly limited, and extraction, recrystallization, adsorption treatment, reprecipitation, column chromatography, supercritical extraction, and the like can be used for purification.

deprotection D

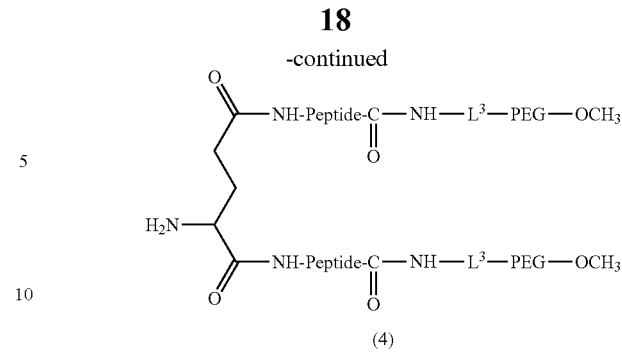

(4)

Deprotection D is a process for removing the protecting group of polyethylene glycol derivative (3) obtained in reaction C to give polyethylene glycol derivative (4). For the deprotection reaction, a conventionally-known method can be used. It is necessary to use conditions that do not cause degradation of oligopeptide and divalent spacer for $L^3$. This step can also be performed as a part of the step of reaction C.

Impurities and the like by-produced in the deprotection reaction are preferably removed by purification. The purification is not particularly limited, and extraction, recrystallization, adsorption treatment, reprecipitation, column chromatography, supercritical extraction, and the like can be used for purification.

reaction E

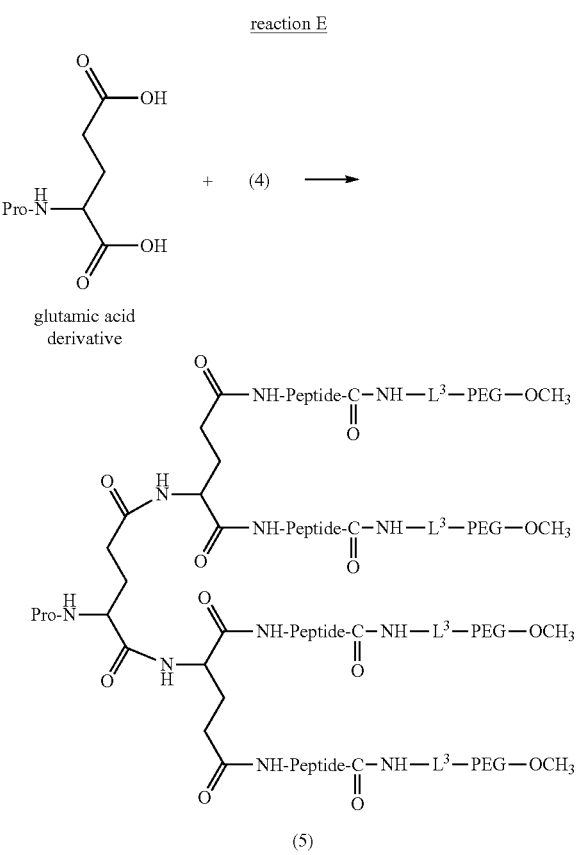

(5)

Reaction E is a process for bonding an amino group of polyethylene glycol derivative (4) obtained in deprotection D, and two carboxyl groups of a glutamic acid derivative in which an amino group is protected by a protecting group by a condensation reaction to give branched polyethylene glycol derivative (5) having a structure in which four degradable polyethylene glycol chains are linked by a glutamic acid residue.

The reaction and purification can be performed under the same conditions as in the aforementioned reaction C.

As a method for removing polyethylene glycol impurities having different molecular weight and different functional group from polyethylene glycol derivative (5), the purification techniques described in JP-A-2014-208786, JP-A-2011-79934 can be used.

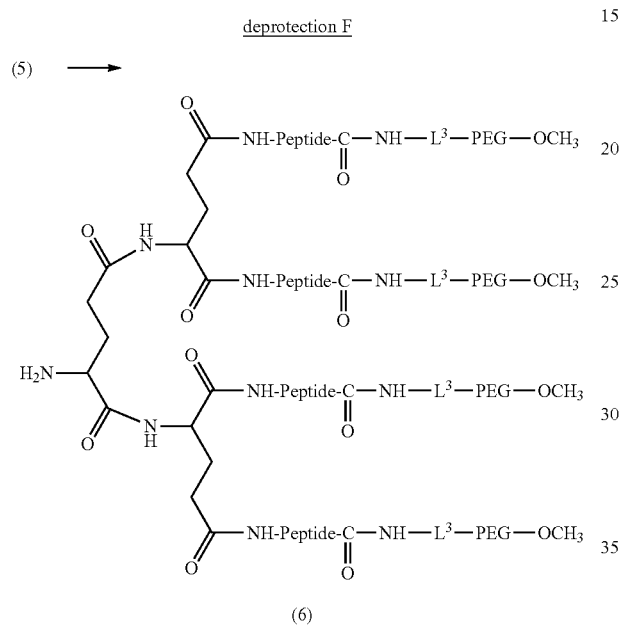

Deprotection F is a process for removing the protecting group of polyethylene glycol derivative (5) obtained in reaction E to give polyethylene glycol derivative (6). For the deprotection reaction, a conventionally-known method can be used. It is necessary to use conditions that do not cause degradation of oligopeptide and divalent spacer for $L^3$. The reaction and purification can be performed under the same conditions as in the aforementioned deprotection D. This step can also be performed as a part of the step of reaction E.

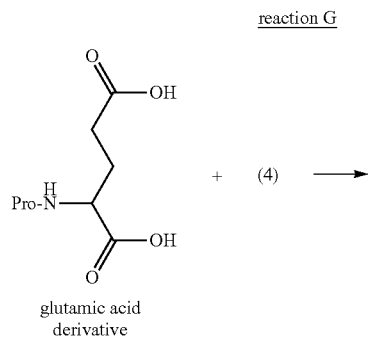

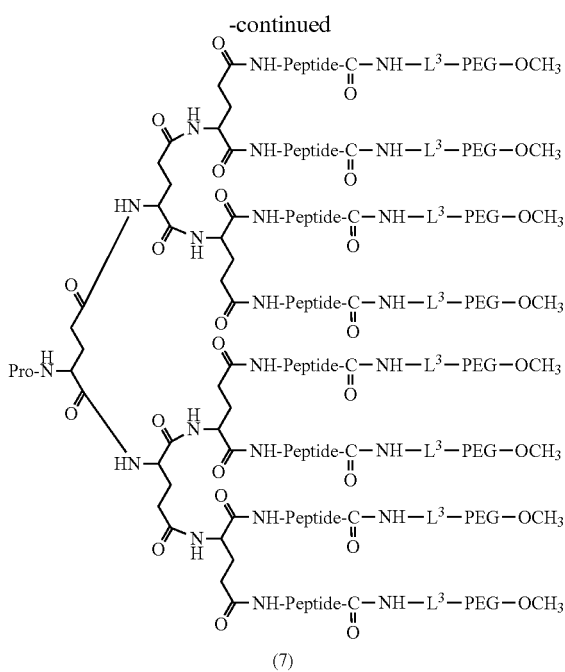

Reaction G is a process for bonding an amino group of polyethylene glycol derivative (6) obtained in deprotection F, and two carboxyl groups of a glutamic acid derivative in which an amino group is protected by a protecting group by a condensation reaction to give branched polyethylene glycol derivative (7) having a structure in which eight degradable polyethylene glycol chains are linked by a glutamic acid residue.

The reaction and purification can be performed under the same conditions as in the aforementioned reaction C.

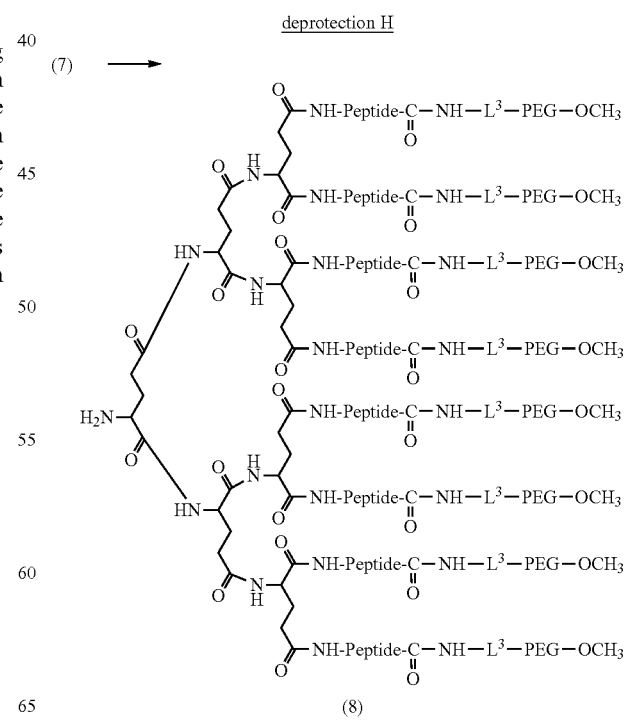

Deprotection H is a process for removing the protecting group of polyethylene glycol derivative (7) obtained in reaction G to give polyethylene glycol derivative (8). The reaction and purification can be performed under the same conditions as in the aforementioned deprotection F. This step can also be performed as a part of the step of reaction G.

By performing reaction A, deprotection B, reaction C and deprotection D mentioned above, the 2 branched and degradable polyethylene glycol derivative (4) is obtained. Using the 2 branched and degradable polyethylene glycol derivative (4) as a starting material, reaction E and deprotection F are successively performed to give the 4 branched and degradable polyethylene glycol derivative (6). By further performing reaction G and deprotection H successively, the 8 branched and degradable polyethylene glycol derivative (8) is obtained.

The polyethylene glycol derivatives (4), (6) and (8) obtained in deprotection D, deprotection F and deprotection H each has one amino group. Utilizing this, conversion to various functional groups is possible.

The step of converting the terminal amino group of the polyethylene glycol derivative into another functional group is not particularly limited. Basically, conversion to various functional groups can be easily performed using a compound having an active ester group capable of reacting with an amino group, or a general reaction reagent such as acid anhydride, acid chloride, or the like.

For example, when conversion of the terminal amino group of a polyethylene glycol derivative to a maleimide group is desired, the desired product can be obtained by reacting with the following reagents.

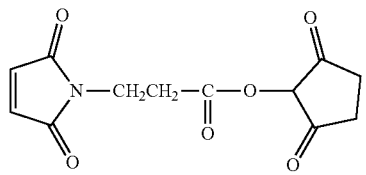

For example, when conversion of the terminal amino group of a polyethylene glycol derivative to a carboxyl group is desired, the desired product can be obtained by reacting with succinic anhydride or glutaric anhydride.

For example, when conversion of the terminal amino group of a polyethylene glycol derivative to a hydroxyl group is desired, the desired product can be obtained by condensation reacting with a ring-opening product of cyclic ester such as caprolactone and the like.

Since these reaction reagents are low-molecular-weight reagents and have solubility vastly different from that of polyethylene glycol derivatives, which are high-molecular-weight polymers, they can be easily removed by general purification methods such as extraction and crystallization.

The degradable polyethylene glycol obtained through the above steps is required to be stable in blood and have the property of being degraded only in cells. To properly evaluate the property, for example, the following test is performed, based on which the stability in blood and degradability in cells of the degradable polyethylene glycol can be evaluated.

In consideration of the influence of the kind of the functional group of the polyethylene glycol derivative in these evaluations, all the evaluation samples used for the tests were polyethylene glycol derivatives having one amino group.

The test method for evaluating the stability of degradable polyethylene glycol derivative in blood is not particularly limited. For example, a test using serum of mouse, rat, human or the like can be mentioned. Specifically, a polyethylene glycol derivative is dissolved in serum to a concentration of 1-10 mg/mL, incubated at 37° C. for 96 hr, the polyethylene glycol derivative contained in the serum is recovered and GPC is measured to evaluate the degradation rate. The degradation rate is calculated from the peak area % of the GPC main fraction of the polyethylene glycol derivative before the stability test and the peak area % of the GPC main fraction of the polyethylene glycol derivative after the stability test. Specifically, the following formula is used.

degradation rate=(peak area % before test−peak area % after test)÷peak area % before test×100

For example, when the peak area % of the GPC main fraction of the degradable polyethylene glycol derivative before the stability test is 95% and the peak area % of the GPC main fraction after the stability test is 90%, the degradation rate is calculated as follows.

degradation rate=(95−90)÷95×100=5.26(%)

When the degradable polyethylene glycol derivative is degraded in blood, the desired half-life in blood cannot be achieved. Thus, in the stability test, the degradation rate after 96 hr is preferably not more than 10%, more preferably not more than 5%.

The test method for evaluating the intracellular degradability of the degradable polyethylene glycol derivative is not particularly limited. For example, a test including culturing cells in a medium containing a degradable polyethylene glycol derivative and the like can be mentioned. The cells and medium to be used here are not particularly limited. Specifically, a polyethylene glycol derivative is dissolved in RPMI-1640 medium to a concentration of 1-20 mg/mL, macrophage cells RAW264.7 are cultured in the medium at 37° C. for 96 hr, the polyethylene glycol derivative in the cells is recovered, and GPC is measured to evaluate the degradation rate. The degradation rate is calculated using the peak area % of the GPC main fraction of the polyethylene glycol derivative before and after the test.

For example, when the peak area % of the GPC main fraction of the degradable polyethylene glycol derivative before the degradability test is 95% and the peak area % of the GPC main fraction after the test is 5%, the degradation rate is calculated as follows.

degradation rate=(95−5)÷95×100=94.7(%)

When the degradable polyethylene glycol derivative is not efficiently degraded in cells, the desired suppression of cell vacuoles cannot be achieved. Thus, in the degradability test, the degradation rate after 96 hr is preferably not less than 90%, more preferably not less than 95%.

The method for bonding the obtained degradable polyethylene glycol derivative to a bio-related substance is not particularly limited, and for example, the methods described in "Hermanson, G. T. Bioconjugate Techniques, 3rd ed.; Academic Press: San Diego, CA, 2013" and "Mark, Sonny S. Bioconjugate protocols, strategies and methods; 2011" can be used. Among them, for example, when targeting a side-chain amino group of a lysine residue of a protein or peptide, which is a bio-related substance, a polyethylene glycol derivative having an activated ester group or an activated carbonate group is used. When targeting a mercapto group of a cysteine residue of a protein or peptide, which is a bio-related substance, a polyethylene glycol derivative having a maleimide group or an iodoacetamide group is used. Since the number of free cysteine residues contained in a natural bio-related substance is extremely small, polyethylene glycol can be more selectively bonded to the bio-related substance by this method. Furthermore, as a method of generating or introducing a mercapto group, a method of cleaving a disulfide bond of a bio-related substance, a method of modifying a bio-related substance by genetic engineering to introduce a cysteine residue, and the like are available. It is known that, by combining with these techniques, a desired number of polyethylene glycol derivatives can be bonded to a desired site of a bio-related substance.

Next, when targeting the N-terminal amino group of a protein or peptide, which is a bio-related substance, a polyethylene glycol derivative having an aldehyde group is used. Specifically, a polyethylene glycol derivative can be selectively bonded to the N-terminal amino group of a protein or peptide by using a polyethylene glycol derivative having an aldehyde group and a suitable reducing agent in a low pH buffer solution.

Bio-related substances bonded to these polyethylene glycol derivatives can be purified by dialysis, gel permeation chromatography (GPC), ion exchange chromatography (IEC), and the like, which are known as general methods. In addition, the obtained bio-related substances can be generally evaluated by analytical methods such as matrix-assisted laser desorption/ionization time-of-flight mass spectrometer (MALDI-TOF-MS), polyacrylamide gel electrophoresis (SDS-PAGE), reverse phase chromatography (RPLC) and the like.

The method for evaluating the physiological activity of a degradable polyethylene glycol derivative-bonded bio-related substance is not particular limited. For example, when the bio-related substance is insulin, blood sugar concentration is measured, and when it is calcitonin, blood calcium concentration is measured, by periodically collecting blood from the animal that received administration and measuring the substance in the blood by using an appropriate analytical instrument, and the like, based on which the evaluation can be performed. Specifically, in the case of insulin, a glucose measurement kit is used to monitor a decrease in glucose concentration after administration and, in the case of calcitonin, a decrease in calcium concentration after administration is monitored using a calcium measurement kit, based on which the evaluation can be performed.

The test method for evaluating the half-life in blood and distribution in vivo of a degradable polyethylene glycol derivative-bonded bio-related substance is not particularly limited. For example, a test including labeling with radioactive isotope or fluorescent substance, administering to mice and rats, followed by monitoring and the like can be mentioned.

A degradable peptide introduced into a polyethylene glycol derivative imparts intracellular degradability to polyethylene glycol. However, the peptide structure thereof may change the pharmacokinetics of a polyethylene glycol-bonded bio-related substance. To confirm the effect of the introduced peptide structure on the pharmacokinetics, it is necessary to compare the blood half-life and distribution thereof in the body with those of a bio-related substance modified with a polyethylene glycol derivative with the same molecular weight and free of degradability. Specifically, radioisotope-labeled bio-related substances are respectively bonded with a non-degradable polyethylene glycol derivative and a degradable polyethylene glycol derivative, the obtained two kinds of bio-related substances are administered to mice, the radiation dose of blood and each organ is measured at plural time points, and quantification measurement can be performed.

The test method for evaluating the half-life in blood and distribution in vivo of the degradable polyethylene glycol derivative is not particularly limited. For example, a test including labeling with radioactive isotope or fluorescent substance, administering to mice and rats, followed by monitoring and the like can be mentioned.

A degradable peptide introduced into a polyethylene glycol derivative imparts intracellular degradability to polyethylene glycol. However, the peptide structure thereof may change the pharmacokinetics of polyethylene glycol. To confirm the effect of the introduced peptide structure on the pharmacokinetics, it is necessary to compare the blood half-life and distribution thereof in the body with those of a polyethylene glycol derivative with the same molecular weight and free of degradability. Specifically, a radioisotope-labeled non-degradable polyethylene glycol derivative and a radioisotope-labeled degradable polyethylene glycol derivative are administered to mice, the radiation dose of blood and each organ is measured at plural time points, and quantification measurement can be performed.

The test method for evaluating suppression of cell vacuoles by a degradable polyethylene glycol derivative is not particularly limited. For example, as described in non-patent document 2, a test including continuing administration to mice and rats at high frequency and high dose for a long period of time and confirming images of the sections of organ and internal organ that are said to be susceptible to vacuole formation can be mentioned.

Specifically, a polyethylene glycol derivative is dissolved in saline to a concentration of 10-250 mg/mL, 20-100 μL thereof is continuously administered from the mouse tail vein 3 times per week for 4 weeks or longer, paraffin sections of cerebral choroid plexus, spleen, and the like that are organs said to be susceptible to vacuole formation are prepared and stained, and the images of the sections are confirmed by a pathological method to evaluate suppression of vacuoles.

In this evaluation, the dose of polyethylene glycol needs to be in large excess compared to the dose of polyethylene glycol that is generally used in the art.

Non-patent document 2 describes that vacuolization of cells by high-molecular-weight polyethylene glycol is related to accumulation of polyethylene glycol in tissue. The test method for evaluating accumulation of a degradable polyethylene glycol derivative in cells is not particularly limited, and evaluation can be made using section images prepared by the same method as the above-mentioned evaluation of vacuole. Stained section images of cerebral choroid plexus, spleen, and the like that are organs said to be susceptible to polyethylene glycol accumulation are confirmed by a pathological method, and accumulation of polyethylene glycol can be evaluated.

In this evaluation, the dose of polyethylene glycol needs to be in large excess compared to the dose of polyethylene glycol that is generally used in the art.

EXAMPLE $^1$H-NMR obtained in the following Examples was obtained from JNM-ECP400 or JNM-ECA600 manufactured by JEOL Datam Co., Ltd. A φ5 mm tube was used for the measurement, and $D_2O$ or $CDCl_3$ and $d_6$-DMSO containing tetramethylsilane (TMS) as an internal standard substance were used as deuterated solvents. The molecular weight and amine purity of the obtained polyethylene glycol derivative were calculated using liquid chromatography (GPC and HPLC). As a liquid chromatography system, "HLC-8320GPC EcoSEC" manufactured by Tosoh Corporation was used for GPC, and "ALLIANCE" manufactured by WATERS was used for HPLC. The analysis conditions of GPC and HPLC are shown below.

GPC Analysis (Molecular Weight Measurement)
  standard polymer: Using polyethylene glycols with molecular weight of 8,000, 20,000, 50,000 and 100,000 as standard polymers, the molecular weight was measured by GPC analysis.
  detector: differential refractometer
  column: ultrahydrogel 500 and ultrahydrogel 250 (manufactured by WATERS)
  mobile phase: 100 mM Acetate buffer+0.02% $NaN_3$ (pH 5.2)
  flow rate: 0.5 mL/min
  sample volume: 5 mg/mL, 20 μL
  column temperature: 30° C.

HPLC Analysis (Amine Purity Measurement)
  detector: differential refractometer
  column: TSKgel SP-5PW (manufactured by Tosoh Corporation)
  mobile phase: 1 mM Sodium phosphate buffer (pH 6.5)
  flow rate: 0.5 mL/min
  injection volume: 5 mg/mL, 20 μL
  column temperature: 40° C.

Example 1

Synthesis of Compound (p3) ($NH_2$-E(FG-200ME)$_2$)

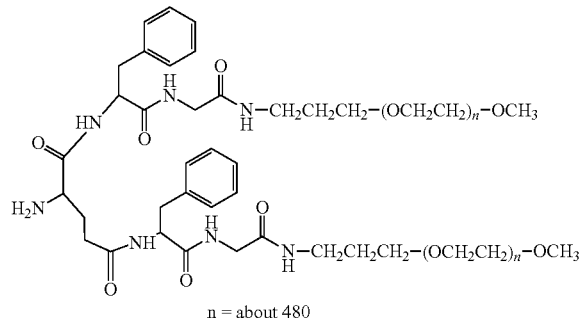

Example 1-1

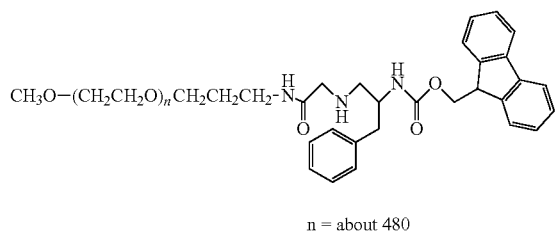

To L-phenylalanyl-glycine with the N terminal protected by a 9-fluorenylmethyloxycarbonyl group (Fmoc group) (Fmoc-Phe-Gly) (0.267 g, $6.0 \times 10^{-4}$ mol, manufactured by WATANABE CHEMICAL INDUSTRIES, LTD.) and methoxy PEG having a propylamino group at the terminal (6.0 g, $2.8 \times 10^{-4}$ mol, number average molecular weight=21,120, "SUNBRIGHT MEPA-20T" manufactured by NOF CORPORATION) was added dehydrated N,N'-dimethylformamide (60 g), and the mixture was dissolved by heating at 30° C. Thereafter, diisopropylethylamine (192 μL, $1.2 \times 10^{-3}$ mol, manufactured by KANTO CHEMICAL CO., INC.) and (1-cyano-2-ethoxy-2-oxoethylideneaminooxy)dimethyl-amino-morpholino-carbenium hexafluorophosphate (COMU) (0.321 g, $7.5 \times 10^{-4}$ mol, manufactured by Sigma-Aldrich Ltd.) were added, and the mixture was reacted at room temperature under a nitrogen atmosphere for 1 hr. After completion of the reaction, the mixture was diluted with chloroform (600 g), saturated aqueous sodium hydrogen carbonate solution (240 g) was added, and the mixture was stirred at room temperature for 15 min for washing. The aqueous layer and the organic layer were separated, saturated aqueous sodium hydrogen carbonate solution (240 g) was added again to the organic layer, the mixture was stirred at room temperature for 15 min for washing, and the organic layer was recovered. To the obtained organic layer (chloroform solution) was added magnesium sulfate (2.4 g), and the mixture was stirred for 30 min for dehydration, and suction filtration was performed using a Kiriyama funnel lined with Oplite on 5A filter paper. The obtained filtrate was concentrated at 40° C., ethyl acetate (240 g) was added to the concentrate, and the mixture was stirred to uniformity. Hexane (120 g) was added, and the mixture was stirred at room temperature for 15 min. The resultant product was precipitated and suction filtered using 5A filter paper. The precipitate was recovered, dissolved again in ethyl acetate (240 g), hexane (120 g) was added, and the mixture was stirred at room temperature for 15 min. The resultant product was precipitated and suction filtered using 5A filter paper. The precipitate was recovered, washed with hexane (120 g), suction filtered using 5A filter paper, and dried in vacuo to give the above-mentioned compound (p1) (ME-200GF-Fmoc). yield 5.1 g.

$^1$H-NMR ($d_6$-DMSO): 1.62 ppm (m, 2H, —CO—NH—$CH_2$—$\underline{CH_2}$—$CH_2$—O— ($CH_2$—$CH_2$—O)n-$CH_3$), 2.80 ppm (m, 1H, —NH—CO—CH—$\underline{CH_2}$—$C_6H_5$), 3.04 ppm (m, 1H, —NH—CO—CH—$\underline{CH_2}$—$C_6H_5$), 3.10 ppm (m, 2H, —CO—NH—$\underline{CH_2}$—$CH_2$—$CH_2$—O—($CH_2$—$CH_2$—O)n-$CH_3$), 3.24 ppm (s, 3H, —CO—NH—$CH_2$—$CH_2$—$CH_2$—O—($CH_2$—$CH_2$—O)n-$\underline{CH_3}$), 3.48 ppm (m, about 1,900H, —CO—NH—$CH_2$—$CH_2$—$CH_2$—O—($\underline{CH_2}$—$\underline{CH_2}$—O)n-$CH_3$), 4.20 ppm (m, 4H), 7.33 ppm (m, 9H), 7.66 ppm (m, 4H, Ar), 7.88 ppm (d, 2H, Ar), 8.27 ppm (t, 1H)

Example 1-2

(p2)

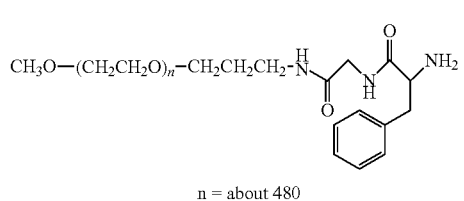

n = about 480

To ME-200GF-Fmoc (4.9 g, 2.3×10⁻⁴ mol) obtained in Example 1-1 was added N,N'-dimethylformamide (29.4 g), and the mixture was dissolved by heating at 30° C. Piperidine (1.55 g, 1.8×10⁻² mol, manufactured by Wako Pure Chemical Industries, Ltd.) was added, and the mixture was reacted at room temperature under a nitrogen atmosphere for 2 hr. After completion of the reaction, ethyl acetate (300 g) was added and the mixture was stirred to uniformity. Hexane (150 g) was added, and the mixture was stirred at room temperature for 15 min. The resultant product was precipitated and suction filtered using 5A filter paper. The precipitate was recovered, dissolved again in ethyl acetate (300 g), hexane (150 g) was added, and the mixture was stirred at room temperature for 15 min. The resultant product was precipitated and suction filtered using 5A filter paper. The precipitate was recovered, washed with hexane (150 g), suction filtered using 5A filter paper, and dried in vacuo to give the above-mentioned compound (p2) (ME-200GF-NH₂). yield 3.9 g.

¹H-NMR (d₆-DMSO): 1.62 ppm (m, 2H, —CO—NH—CH₂—CH₂—CH₂—O— (CH₂—CH₂—O)n-CH₃), 1.64 ppm (broad, 1H), 2.59 ppm (dd, 1H, —NH—CO—CH—CH₂—C₆H₅), 2.98 ppm (dd, 1H, —NH—CO—CH—CH₂—C₆H₅), 3.10 ppm (q, 2H, —CO—NH—CH₂—CH₂—CH₂—O—(CH₂—CH₂—O)n-CH₃), 3.24 ppm (s, 3H, —CO—NH—CH₂—CH₂—CH₂—O—(CH₂—CH₂—O)n-CH₃), 3.48 ppm (m, about 1,900H, —CO—NH—CH₂—CH₂—O— (CH₂—CH₂—O)n-CH₃), 7.24 ppm (m, 6H, —NH—CO—CH—CH₂—C₆H₅, —NH—), 7.73 ppm (t, 1H), 8.12 ppm (broad, 1H)

Example 1-3

(p3)

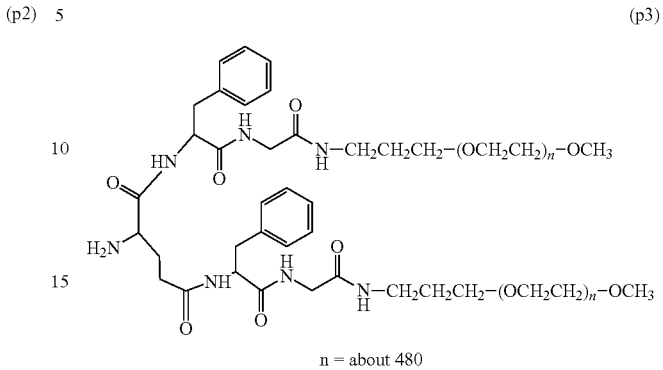

n = about 480

L-glutamic acid with N terminal protected by an Fmoc group (Fmoc-Glu-OH) (16.0 mg, 4.3×10⁻⁵ mol, manufactured by WATANABE CHEMICAL INDUSTRIES, LTD.) and ME-200GF-NH₂ (2.0 g, 1.0×10⁻⁴ mol) obtained in Example 1-2 was added dehydrated N,N'-dimethylformamide (10 g), and the mixture was dissolved by heating at 30° C. Thereafter, diisopropyl ethylamine (19.2 µL, 1.1×10⁻⁴ mol, manufactured by KANTO CHEMICAL CO., INC.) and 4-(4,6-dimethoxy-1,3,5-triazin-2-yl)-4-methylmorpholinium chloride n hydrate (DMT-MM) (39.0 mg, 1.1×10⁻⁴ mol, manufactured by Wako Pure Chemical Industries, Ltd.) were added, and the mixture was reacted at room temperature under a nitrogen atmosphere for 1 hr. Thereafter, piperidine (0.5 g, 5.9×10⁻³ mol, manufactured by Wako Pure Chemical Industries, Ltd.) was added, and the mixture was reacted at room temperature under a nitrogen atmosphere for 2 hr. After completion of the reaction, the reaction solution was diluted with toluene (80 g). Hexane (40 g) was added, and the mixture was stirred at room temperature for 15 min. The resultant product was precipitated and suction filtered using 5A filter paper. The precipitate was recovered, dissolved again in toluene (80 g), hexane (40 g) was added, and the mixture was stirred at room temperature for 15 min. The resultant product was precipitated and suction filtered using 5A filter paper. The precipitate was recovered, washed with hexane (40 g), suction filtered using 5A filter paper, and dried in vacuo to give the above-mentioned compound (p3) (NH₂-E(FG-200ME)₂). yield 1.6 g. The molecular weight is shown in Table 1. HPLC: amine purity 92%.

¹H-NMR (d₆-DMSO): 1.54 ppm (m, 2H, —NH—CO—CH(NH₂)—CH₂—CH₂—), 1.62 ppm (m, 4H, —CO—NH—CH₂—CH₂—CH₂—), 1.97 ppm (m, 2H, —NH—CO—CH(NH₂)—CH₂—CH₂—), 2.74 ppm (dd, 1H, —CO—NH—CH—CH₂—C₆H₅), 2.81 ppm (dd, 1H, —CO—NH—CH—CH₂—C₆H₅), 3.11 ppm (m, 11H), 3.24 ppm (s, 6H, —CO—NH—CH₂—CH₂—CH₂—O—(CH₂—CH₂—O)n-CH₃), 3.64 ppm (m, about 3,800H, —CO—NH—CH₂—CH₂—CH₂—O—(CH₂—CH₂—O)n-CH₃), 4.49 ppm (m, 1H, —CO—NH—CH—CH₂—C₆H₅), 4.57 ppm (m, 1H, —CO—NH—CH—CH₂—C₆H₅), 7.25 ppm (m, 10H, —CO—NH—CH—CH₂—C₆H₅), 7.74 ppm (m, 2H), 8.44 ppm (m, 2H), 8.61 ppm (m, 2H)

Example 2

Synthesis of Compound (p4) (MA-E(FG-200ME)$_2$)

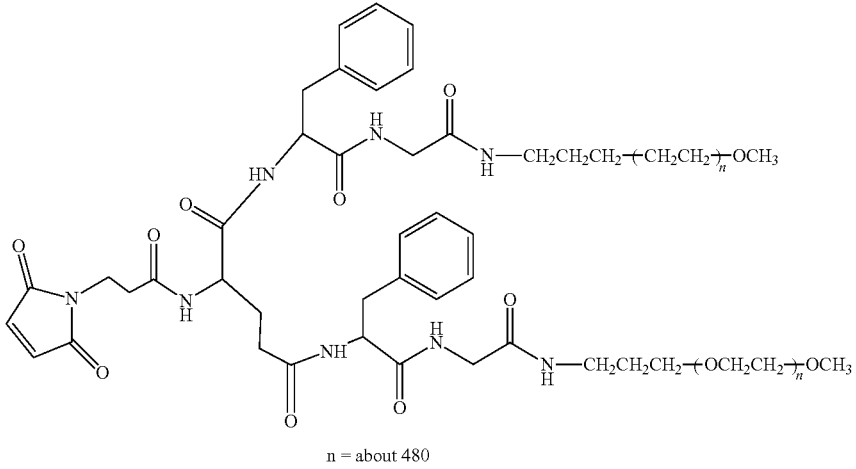

(p4)

n = about 480

The compound (p3) (200 mg, 5.0×10$^{-6}$ mol) obtained in Example 1 was dissolved in acetonitrile (160 mg) and toluene (1.0 g). Thereafter, N-methylmorpholine (10 mg, 1.0×10$^{-5}$ mol, manufactured by KANTO CHEMICAL CO., INC.) and 3-maleimide propionic acid N-succinimidyl (8.0 mg, 3.0×10$^{-5}$ mol, manufactured by Osaka Synthesis Organic Chemistry Laboratory Co., Ltd.) were added, and the mixture was reacted at room temperature under a nitrogen atmosphere and shading for 6 hr. After completion of the reaction, the reaction solution was diluted with ethyl acetate (50 g) containing 2,6-di-tert-butyl-p-cresol (BHT) (10 mg). Hexane (25 g) was added and the mixture was stirred at room temperature for 15 min. The resultant product was precipitated and suction filtered using 5A filter paper. The precipitate was recovered, washed with hexane (25 g) containing BHT (5 mg), suction filtered using 5A filter paper, and dried in vacuo to give the above-mentioned compound (p4) (MA-E(FG-200ME)$_2$). yield 137 mg. The molecular weight is shown in Table 1. Maleimide purity was 90% ($^1$H-NMR).

$^1$H-NMR (d$_6$-DMSO): 1.62 ppm (m, 6H), 1.99 ppm (m, 2H, —NH—CO—CH(NH$_2$)—CH$_2$—CH$_2$—), 2.34 ppm (m, 2H, —NH—CO—CH$_2$—CH$_2$-Maleimide), 2.75 ppm (dd, 1H, —CO—NH—CH—CH$_2$—C$_6$H$_5$), 2.82 ppm (dd, 1H, —CO—NH—CH—CH$_2$—C$_6$H$_5$), 3.11 ppm (m, 11H), 3.24 ppm (s, 6H, —CO—NH—CH$_2$—CH$_2$—CH$_2$—O—(CH$_2$—CH$_2$—O)n-CH$_3$), 3.64 ppm (m, about 3,800H, —CO—NH—CH$_2$—CH$_2$—CH$_2$—O—(CH$_2$—CH$_2$—O)n-CH$_3$), 4.04 ppm (m, 2H, —NH—CO—CH$_2$—CH$_2$-Maleimide), 4.49 ppm (m, 2H, —CO—NH—CH—CH$_2$—C$_6$H$_5$), 6.98 ppm (s, 2H, —CO—CH—CH—CO—), 7.25 ppm (m, 10H, —CO—NH—CH—CH$_2$—C$_6$H$_5$), 7.69 ppm (dt, 2H), 8.04 ppm (d, 1H), 8.29 ppm (dd, 2H), 8.41 ppm (dt, 2H)

Example 3

Synthesis of Compound (p8) (AL-E(FG-200ME)$_2$)

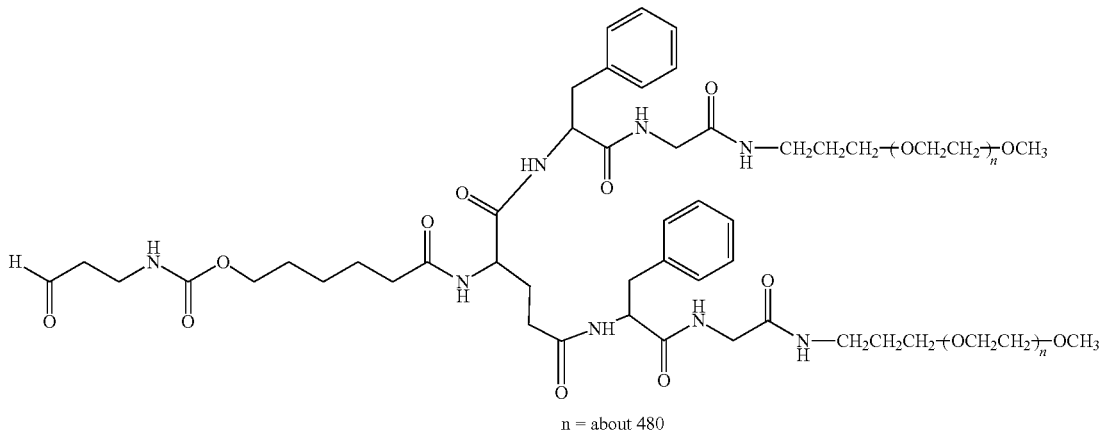

(p8)

n = about 480

Example 3-1

Synthesis of Compound (p5) (HO-E(FG-200ME)$_2$)

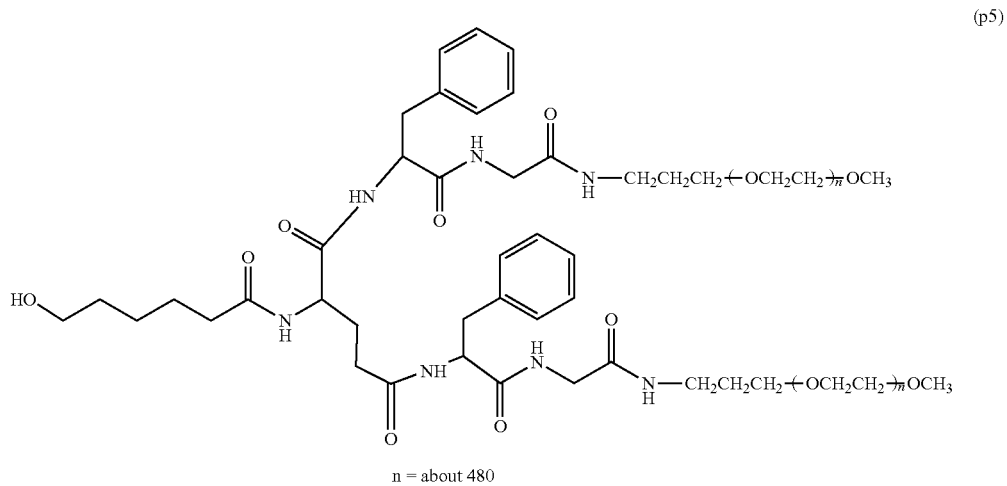

n = about 480

ε-Caprolactone (114 mg, $1.0 \times 10^{-3}$ mol, manufactured by Tokyo Chemical Industry Co., Ltd.) was dissolved in 1N NaOH (0.8 mL, $8.0 \times 10^{-4}$ mol, manufactured by KANTO CHEMICAL CO., INC.) and reacted for 2 hr to prepare 6-hydroxycaproic acid aqueous solution (0.88M). The compound (p3) (2.0 g, $5.0 \times 10^{-5}$ mol) obtained in Example 1 was dissolved in acetonitrile (8.0 g). Thereafter, the above-mentioned 6-hydroxycaproic acid aqueous solution (114 μL, $1.0 \times 10^{-4}$ mol), diisopropyl ethylamine (20 μL, $1.2 \times 10^{-4}$ mol, manufactured by KANTO CHEMICAL CO., INC.), and DMT-MM (21 mg, $6.0 \times 10^{-5}$ mol, manufactured by Wako Pure Chemical Industries, Ltd.) were added to an acetonitrile solution of the above-mentioned (p3), and the mixture was reacted at room temperature under a nitrogen atmosphere for 1 hr. After completion of the reaction, the reaction solution was concentrated at 40° C., chloroform (24 g) was added, and the obtained concentrate was dissolved therein. Saturated aqueous sodium hydrogen carbonate solution (10 g) was added, and the mixture was stirred at room temperature for 15 min for washing. The aqueous layer and the organic layer were separated, saturated aqueous sodium hydrogen carbonate solution (10 g) was added again to the organic layer, the mixture was stirred at room temperature for 15 min for washing, and the organic layer was recovered. Magnesium sulfate (1.2 g) was added to the obtained organic layer (chloroform solution). The mixture was stirred for 30 min for dehydration, and suction filtration was performed using a Kiriyama funnel lined with Oplite on 5A filter paper. The obtained filtrate was concentrated at 40° C., toluene (50 g) was added to the concentrate and the mixture was stirred to uniformity. Hexane (25 g) was added, and the mixture was stirred at room temperature for 15 min. The resultant product was precipitated and suction filtered using 5A filter paper. The precipitate was recovered, dissolved again in toluene (50 g) Hexane (25 g) was added, and the mixture was stirred at room temperature for 15 min. The resultant product was precipitated and suction filtered using 5A filter paper. The precipitate was recovered, washed with hexane (10 g) containing BHT (2 mg), suction filtered using 5A filter paper, and dried in vacuo to give the above-mentioned compound (p5) (HO-E(FG-200ME)$_2$). yield 1.5 g.

$^1$H-NMR (CDCl$_3$): 1.37 ppm (m, 2H, HO—CH$_2$—CH$_2$—CH$_2$—CH$_2$—CH$_2$—CO—NH—), 1.55 ppm (m, 4H, HO—CH$_2$—CH$_2$—CH$_2$—CH$_2$—CH$_2$—CO—NH—), 1.77 ppm (m, 4H, —CO—NH—CH$_2$—CH$_2$—CH$_2$—O—(CH$_2$—CH$_2$-0)n-CH$_3$), 1.85 ppm (m, 1H), 2.01 ppm (m, 2H, HO—CH$_2$—CH$_2$—CH$_2$—CH$_2$—CH$_2$—CO—NH—), 3.01 ppm (m, 1H), 3.24 ppm (m, 8H), 3.38 ppm (s, 6H, —CO—NH—CH$_2$—CH$_2$—CH$_2$—O—(CH$_2$—CH$_2$—O)n-CH$_3$), 3.64 ppm (m, about 3,800H, —CO—NH—CH$_2$—CH$_2$—CH$_2$—O—(CH$_2$—CH$_2$—O)n-CH$_3$), 4.03 ppm (m, 4H), 4.14 ppm (m, 1H), 4.48 ppm (m, 2H, —CO—NH—CH—

$CH_2$—$C_6H_5$), 6.95 ppm (broad, 1H), 7.00 ppm (broad, 1H), 7.26 ppm (m, 10H, —CO—NH—CH—$CH_2$—$\underline{C_6H_5}$), 7.66 ppm (broad, 1H), 8.29 ppm (broad, 1H)

Example 3-2

Synthesis of Compound (p6) (SC-E(FG-200ME)$_2$)

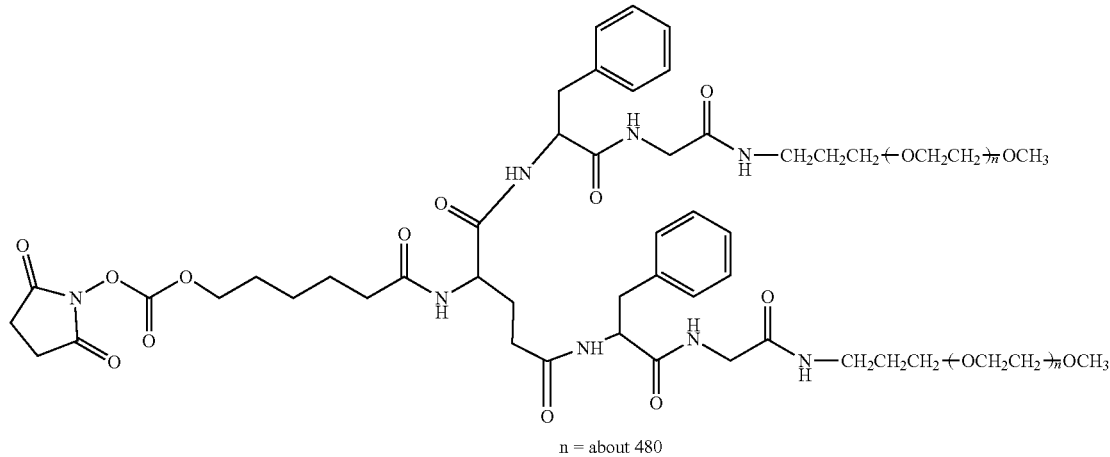

(p6)

n = about 480

The compound (p5) (500 mg, $1.3 \times 10^{-5}$ mol) obtained in Example 3-1 was dissolved in dichloromethane (3.5 g). Thereafter, di(N-succinimidyl)carbonate (51 mg, $2.0 \times 10^{-4}$ mol, manufactured by Tokyo Chemical Industry Co., Ltd.) and pyridine (24 μL, $3.0 \times 10^{-4}$ mol, manufactured by KANTO CHEMICAL CO., INC.) were added, and the mixture was reacted at room temperature under a nitrogen atmosphere for 8 hr. After completion of the reaction, the reaction solution was washed with 5% brine, magnesium sulfate (0.1 g) was added, and the mixture was stirred at 25° C. for 30 min, and suction filtration was performed using a Kiriyama funnel lined with Oplite on 5A filter paper. The obtained filtrate was concentrated, and toluene (50 g) was dissolved in the concentrate. Hexane (25 g) was added, and the mixture was stirred at room temperature for 15 min. The resultant product was precipitated and suction filtered using 5A filter paper. The precipitate was recovered, dissolved again in toluene (50 g). Hexane (25 g) was added and the mixture was stirred at room temperature for 15 min. The resultant product was precipitated and suction filtered using 5A filter paper. The precipitate was recovered, washed with hexane (25 g) containing BHT (5 mg), suction filtered using 5A filter paper, and dried in vacuo to give the above-mentioned compound (p6) (SC-E(FG-200ME)$_2$). yield 286 mg. The active carbonate purity was 92% ($^1$H-NMR).

$^1$H-NMR (CDCl$_3$): 1.38 ppm (m, 2H, Succinimide-OCO—$CH_2$—$CH_2$—$\underline{CH_2}$—$CH_2$—$CH_2$—CO—NH—), 1.59 ppm (m, 2H, Succinimide-OCO—$CH_2$—$CH_2$—$CH_2$—$\underline{CH_2}$—$CH_2$—CO—NH—), 1.75 ppm (m, 6H), 1.85 ppm (m, $\underline{1H}$), 2.13 ppm (m, 2H, Succinimide-OCO—$CH_2$—$CH_2$—$CH_2$—$CH_2$—$\underline{CH_2}$—CO—NH—), 2.83 ppm (s, 4H, —CO—$\underline{CH_2}$—$\underline{CH_2}$—CO—), 3.01 ppm (m, 1H), 3.19 ppm (m, 6H), 3.38 ppm (s, 6H, —CO—NH—$CH_2$—$CH_2$—$CH_2$—O—($CH_2$—$CH_2$—O)n-$\underline{CH_3}$), 3.64 ppm (m, about 3,800H, —CO—NH—$CH_2$—$CH_2$—$CH_2$—O—($\underline{CH_2}$—$\underline{CH_2}$—O)n-$CH_3$), 4.03 ppm (m, 3H), 4.18 ppm (m, 1H), 4.31 ppm (t, 2H, Succinimide-OCO—$\underline{CH_2}$—$CH_2$—$CH_2$—$CH_2$—$CH_2$—CO—NH—), 4.50 ppm (m, 2H, —CO—NH—$\underline{CH}$—$CH_2$—$C_6H_5$), 6.98 ppm (broad, 1H), 7.15 ppm (broad, $\underline{1H}$), 7.26 ppm (m, 10H, —CO—NH—CH—$CH_2$—$\underline{C_6H_5}$), 7.81 ppm (broad, 1H), 8.37 ppm (broad, 1H)

Example 3-3

Synthesis of Compound (p7) (DE-E(FG-200ME)$_2$)

(p7)

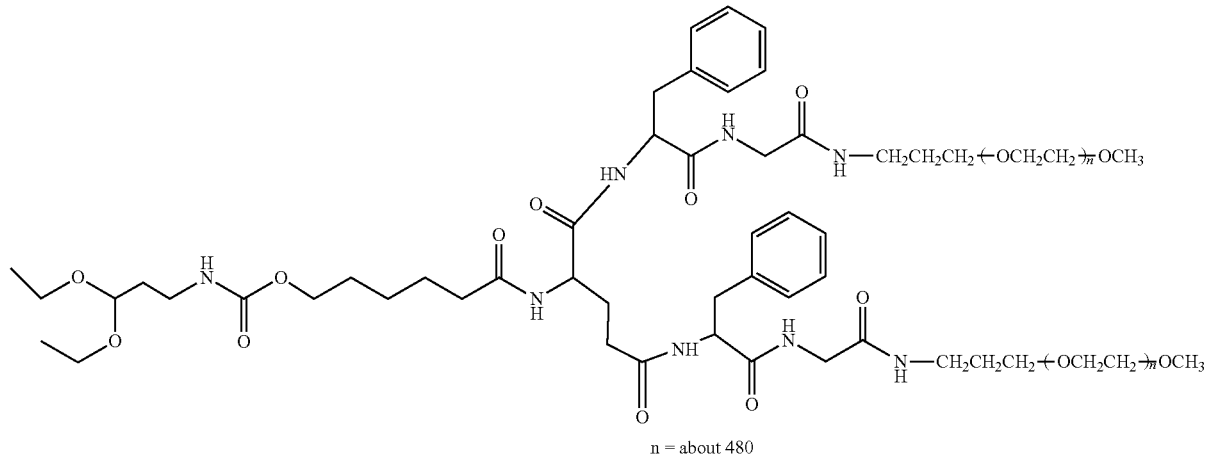

n = about 480

The compound (p6) (250 mg, 6.3×10$^{-6}$ mol) obtained in Example 3-2 was dissolved in chloroform (2 g). Thereafter, 1-amino-3,3-diethoxypropane (10 μL, 6.3×10$^{-5}$ mol, manufactured by ACROS ORGANICS) was added, and the mixture was reacted at room temperature under a nitrogen atmosphere for 3 hr. After completion of the reaction, the reaction solution was diluted with toluene (25 g). Hexane (12.5 g) was added and the mixture was stirred at room temperature for 15 min. The resultant product was precipitated and suction filtered using 5A filter paper. The precipitate was recovered, washed with hexane (12.5 g) containing BHT (2.5 mg), suction filtered using 5A filter paper, and dried in vacuo to give the above-mentioned compound (p47) (DE-E(FG-200ME)$_2$). yield 185 mg.

$^1$H-NMR (CDCl$_3$): 1.20 ppm (t, 6H, (CH$_3$—CH$_2$—O)$_2$—CH—), 1.32 ppm (m, 2H, (CH$_3$—CH$_2$—O)$_2$—CH—CH$_2$—CH$_2$—NH—COO—CH$_2$—CH$_2$—CH$_2$—CH$_2$—CH$_2$—CO—NH—), 1.58 ppm (m, 2H, (CH$_3$—CH$_2$—O)$_2$—CH—CH$_2$—CH$_2$—NH—COO—CH$_2$—CH$_2$—CH$_2$—CH$_2$—CH$_2$—CO—NH—), 1.76 ppm (m, 4H, —CO—NH—CH$_2$—CH$_2$—CH$_2$—O—(CH$_2$—CH$_2$—O)n-CH$_3$), 1.82 ppm (m, 2H, (CH$_3$—CH$_2$—O)$_2$—CH—CH$_2$—CH$_2$—NH—COO—CH$_2$—CH$_2$—CH$_2$—CH$_2$—CH$_2$—CO—NH—), 2.11 ppm (m, 2H, (CH$_3$—CH$_2$—O)$_2$—CH—CH$_2$—CH$_2$—NH—COO—CH$_2$—CH$_2$—CH$_2$—CH$_2$—CH$_2$—CO—NH—), 2.16 ppm (m, 1H), 2.70 ppm (m, 1H), 3.06 ppm (m, 2H), 3.25 ppm (m, 11H), 3.38 ppm (s, 6H, —CO—NH—CH$_2$—CH$_2$—CH$_2$—O—(CH$_2$—CH$_2$—O)n-CH$_3$), 3.64 ppm (m, about 3,800H, —CO—NH—CH$_2$—CH$_2$—CH$_2$—O—(CH$_2$—CH$_2$—O)n-CH$_3$), 4.02 ppm (m, 8H), 4.17 ppm (m, 1H), 4.51 ppm (m, 2H, —CO—NH—CH—CH$_2$—C$_6$H$_5$), 4.55 ppm (t, 1H, (CH$_3$—CH$_2$—O)$_2$—CH—), 5.36 ppm (broad, 1H), 6.47 ppm (broad, 1H), 6.98 ppm (broad, 2H), 7.26 ppm (m, 10H, —CO—NH—CH—CH$_2$—C$_6$H$_5$), 7.81 ppm (broad, 1H), 8.36 ppm (broad, 1H)

Example 3-4

Synthesis of Compound (p8) (AL-E(FG-200ME)$_2$)

(p8)

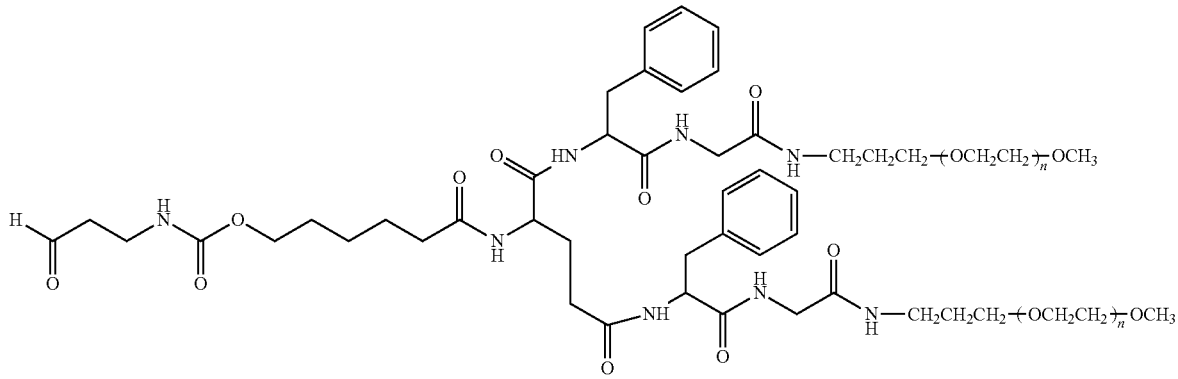

n = about 480

The compound (p7) (150 mg, 3.8×10⁻⁶ mol) obtained in Example 3-3 was dissolved in phosphate buffer solution (2.25 g) adjusted to pH 1.90, and the mixture was reacted at room temperature under a nitrogen atmosphere for 3 hr. After the reaction, the pH of the mixture was adjusted to 6.40 by adding 0.1N sodium hydroxide aqueous solution (0.89 g), and sodium chloride (0.56 g) was added and dissolved. To the obtained solution was added dropwise 0.1N sodium hydroxide aqueous solution (0.60 g) to adjust the pH to 7.06, chloroform (3 g) containing BHT (0.6 mg) was added, and the mixture was stirred at room temperature for 20 min. The resultant product was extracted into the organic layer. The organic layer and the aqueous layer were separated, the organic layer was recovered, chloroform (3 g) containing BHT (0.6 mg) was added again to the aqueous layer, and the mixture was stirred at room temperature for 20 min. The resultant product was extracted into the organic layer. The organic layers obtained by the first extraction and the second extraction were combined and concentrated at 40° C., and the obtained concentrate was diluted with toluene (30 g). Hexane (15 g) was added, and the mixture was stirred at room temperature for 15 min. The resultant product was precipitated and suction filtered using 5A filter paper. The precipitate was recovered, washed with hexane (15 g) containing BHT (3.0 mg), suction filtered using 5A filter paper, and dried in vacuo to give the above-mentioned compound (p8) (AL-E(FG-200ME)₂). yield 84 mg. The molecular weight is shown in Table 1. Aldehyde purity was 92% (¹H-NMR).

¹H-NMR (CDCl₃): 1.32 ppm (m, 2H, CHO—CH₂—CH₂—NH—COO—CH₂—CH₂—C̲H̲₂—CH₂—CH₂—CO—NH—), 1.57 ppm (m, 2H, CHO—CH₂—CH₂—NH—COO—CH₂—CH₂—CH₂—C̲H̲₂—CH₂—CO—NH—), 1.76 ppm (m, 4H, —CO—N̲H̲—CH₂—C̲H̲₂—CH₂—O—(CH₂—CH₂—O)n-CH₃), 1.82 ppm (m, 1H̲), 2.10 ppm (m, 2H, CHO—CH₂—CH₂—NH—COO—CH₂—C̲H̲₂—CH₂—CH₂—CH₂—CO—NH—), 2.16 ppm (m, 1H), 2.71 ppm (m, 2H, CHO—C̲H̲₂—CH₂—NH—COO—CH₂—CH₂—CH₂—CH₂—CO—NH—), 3.02 ppm (m, 1H), 3.26 ppm (m, 8H), 3.38 ppm (s, 6H, —CO—NH—CH₂—CH₂—CH₂—O—(CH₂—CH₂—O)n-C̲H̲₃), 3.64 ppm (m, about 3,800H, —CO—NH—CH₂—CH₂—CH₂—O—(C̲H̲₂—C̲H̲₂—O)n-CH₃), 4.01 ppm (m, 4H), 4.16 ppm (m, 1H), 4.49 ppm (m, 2H, —CO—NH—C̲H̲—CH₂— C₆H₅), 5.59 ppm (broad, 1H), 6.36 ppm (broad, 1H), 6.93 ppm (broad, 2H), 7.08 ppm (broad, 1H), 7.26 ppm (m, 10H, —CO—NH—CH—CH₂—C̲₆H̲₅), 7.80 ppm (broad, 1H), 8.37 ppm (broad, 1H), 9.79 ppm (s, 1H, C̲H̲O—CH₂—CH₂—NH—COO—)

Example 4

Synthesis of Compound (p9) (NH₂O-E(FG-200ME)₂)

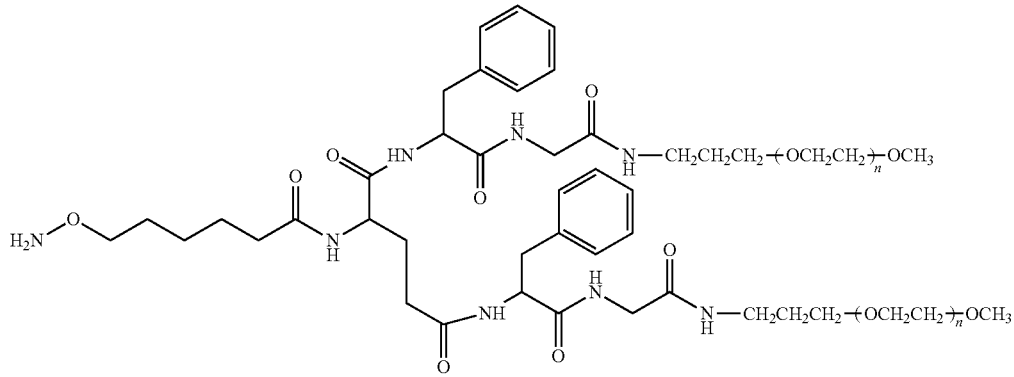

(p9)

n = about 480

The compound (p5) (300 mg, 7.5×10⁻⁶ mol) obtained in Example 3-1 was dissolved in toluene (2.4 g) by heating at 30° C., and azeotropically distilled with dehydrating under reduced pressure. Thereafter, the concentrate was dissolved in chloroform (2.4 g), N-hydroxyphthalimide (7.3 mg, 4.5×10⁻⁵ mol, manufactured by Wako Pure Chemical Industries, Ltd.), triphenyl phosphine (35 mg, 1.4×10⁻⁴ mol, manufactured by KANTO CHEMICAL CO., INC.) and diisopropyl azodicarboxylate (22 μL, 1.1×10⁻⁴ mol, manufactured by ACROS ORGANICS) were added, and the mixture was reacted at room temperature under a nitrogen atmosphere for 4 hr. After completion of the reaction, methanol (9.1 μL) was added to the reaction solution and the mixture was stirred at 25° C. for 30 min and concentrated at 40° C. The concentrate was diluted with toluene (3.0 g) and azeotropically distilled. The concentrate was dissolved in toluene (1.5 g), ethylenediamine monohydrate (24 μL, 3.0×10⁻⁴ mol, manufactured by KANTO CHEMICAL CO., INC.)) was added, and the mixture was reacted at room temperature under a nitrogen atmosphere for 1 hr. After completion of the reaction, the reaction solution was diluted with toluene (50 g). Hexane (25 g) was added, and the mixture was stirred at room temperature for 15 min. The resultant product was precipitated and suction filtered using 5A filter paper. The precipitate was recovered, dissolved again in ethyl acetate (50 g). Hexane (25 g) was added at room temperature, and the mixture was stirred at room temperature for 15 min. The resultant product was precipitated and suction filtered using 5A filter paper. The precipitate was recovered, washed with hexane (20 g), suction filtered using 5A filter paper, and dried in vacuo to give the above-mentioned compound (p9) (NH₂O-E(FG-200ME)₂). yield 156 mg. The molecular weight is shown in Table 1. HPLC: oxyamine purity 91%.

¹H-NMR (CDCl₃): 1.32 ppm (m, 2H, H₂N—O—CH₂—CH₂—C̲H̲₂—CH₂—CH₂—CO—NH—), 1.56 ppm (m, 4H, H₂N—O—CH₂—CH₂—CH₂—CH₂—CH₂—CO—NH—), 1.76 ppm (m, 4H, —CO—NH—CH₂—CH₂—CH₂—O—(CH₂—CH₂—O)n-CH₃), 1.85 ppm (m, 1H), 2.10 ppm (m, 2H, H₂N—O—CH₂—CH₂—CH₂—CH₂—CH₂—CO—NH—), 2.17 ppm (m, 1H), 3.01 ppm (m, 1H), 3.24 ppm (m, 8H), 3.38 ppm (s, 6H, —CO—NH—CH₂—CH₂—CH₂—O—(CH₂—CH₂—O)n-CH₃), 3.64 ppm (m, about 3,800H, —CO—NH—CH₂—CH₂—CH₂—O—(CH₂—CH₂—O)n-CH₃), 4.03 ppm (m, 2H), 4.17 ppm (m, 1H), 4.49 ppm (m, 2H, —CO—NH—CH—CH₂—C₆H₅), 5.37 ppm (broad, 2H), 6.40 ppm (broad, 1H), 6.95 ppm (broad, 2H), 7.12 ppm (broad, 1H), 7.26 ppm (m, 10H, —CO—NH—CH—CH₂—C₆H₅), 7.74 ppm (broad, 1H), 8.31 ppm (broad, 1H)

Example 5

Synthesis of Compound (p13) (NH₂-E{E(FG-100ME)₂}₂)

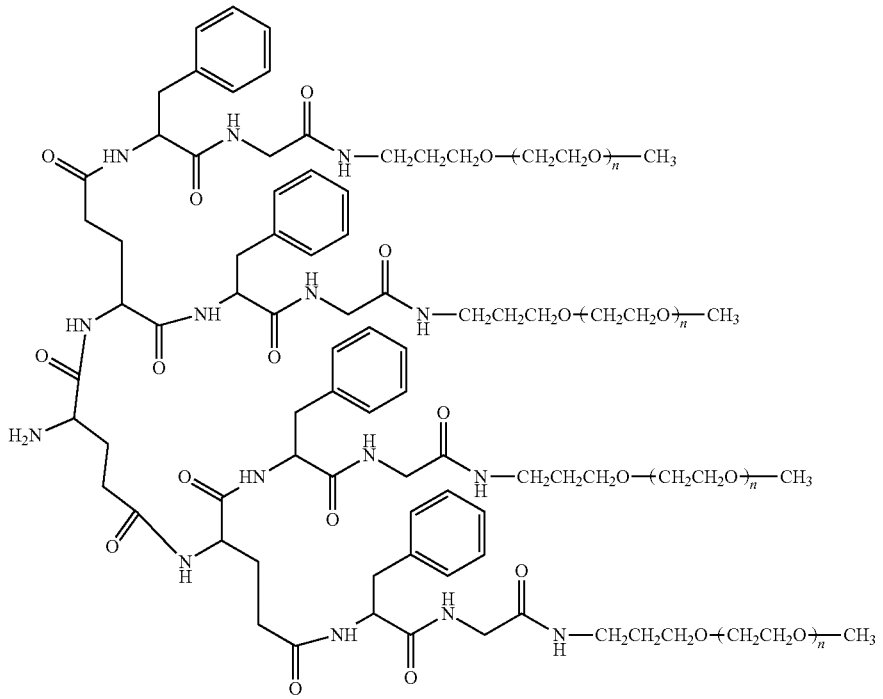

(p13)

n = about 225

Example 5-1

Synthesis of Compound (p10) (ME-100GF-Fmoc)

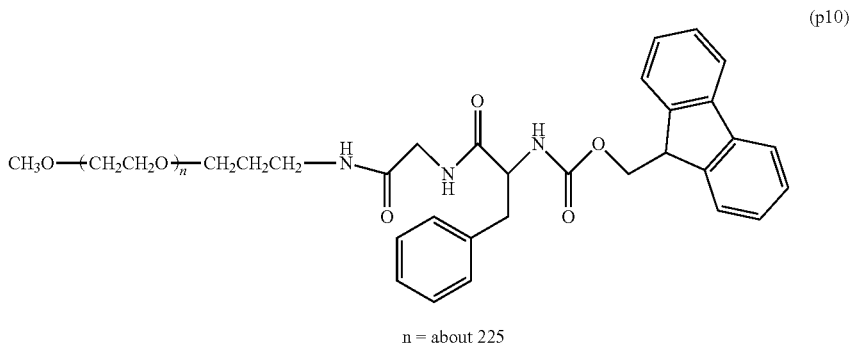

n = about 225

By the same production method as in Example 1-1, and using L-phenylalanyl-glycine with the N terminal protected by an Fmoc group (Fmoc-Phe-Gly) (533 mg, $1.2 \times 10^{-3}$ mol, manufactured by WATANABE CHEMICAL INDUSTRIES, LTD.) and methoxy PEG having a propylamino group at the terminal (9.9 g, $1.0 \times 10^{-3}$ mol, number average molecular weight=9,896, "SUNBRIGHT MEPA-10T" manufactured by NOF CORPORATION) as starting materials, the above-mentioned compound (p10) (ME-100GF-Fmoc) was obtained. yield 9.2 g.

$^1$H-NMR ($d_6$-DMSO): 1.62 ppm (m, 2H, —CO—NH—$CH_2$—$\underline{CH_2}$—$CH_2$—O— ($CH_2$—$CH_2$—O)n-$CH_3$), 2.80 ppm (m, 1H, —NH—CO—CH—$\underline{CH_2}$—$C_6H_5$), 3.04 ppm (m, 1H, —NH—CO—CH—$\underline{CH_2}$—$C_6H_5$), 3.10 ppm (m, 2H, —CO—NH—$\underline{CH_2}$—$CH_2$—$CH_2$—O— ($CH_2$—$CH_2$—O)n-$CH_3$), 3.24 ppm (s, 3H, —CO—NH—$CH_2$—$CH_2$—$CH_2$—O—($\underline{CH_2}$—$CH_2$—O)n-$CH_3$), 3.48 ppm (m, about 900H, —CO—NH—$CH_2$—$CH_2$—$CH_2$—O—($\underline{CH_2}$—$\underline{CH_2}$—O)n-$CH_3$), 4.20 ppm (m, 4H), 7.33 ppm (m, 9H), 7.66 ppm (m, 4H, Ar), 7.88 ppm (d, 2H, Ar), 8.27 ppm (t, 1H)

Example 5-2

Synthesis of Compound (p11) (ME-100GF-$NH_2$)

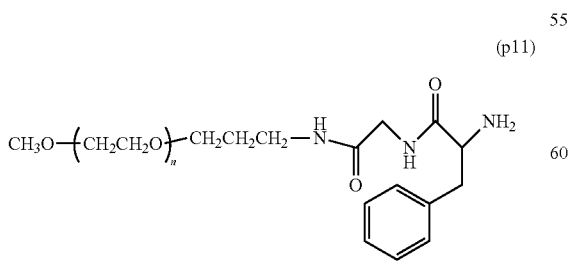

n = about 225

By the same production method as in Example 1-2, and using the compound (p10) (9.2 g, $4.6 \times 10^{-4}$ mol) obtained in Example 5-1, a deprotection reaction was performed to give the above-mentioned compound (p11) (ME-100GF-$NH_2$). yield 8.7 g.

$^1$H-NMR ($d_6$-DMSO): 1.62 ppm (m, 2H, —CO—NH—$CH_2$—$\underline{CH_2}$—$CH_2$—O— ($CH_2$—$CH_2$—O)n-$CH_3$), 1.64 ppm (broad, 1H), 2.59 ppm (dd, 1H, —NH—CO—CH—$\underline{CH_2}$—$C_6H_5$), 2.98 ppm (dd, 1H, —NH—CO—CH—$\underline{CH_2}$—$C_6H_5$), 3.10 ppm (q, 2H, —CO—NH—$\underline{CH_2}$—$CH_2$—$CH_2$—O—($CH_2$—$CH_2$-O)n-$CH_3$), 3.24 ppm (s, 3H, —CO—NH—$CH_2$—$CH_2$—$CH_2$—O—($CH_2$—$CH_2$—O)n-$\underline{CH_3}$), 3.48 ppm (m, about 900H, —CO—NH—$CH_2$—$CH_2$—$CH_2$—O—($\underline{CH_2}$—$\underline{CH_2}$—O)n-$CH_3$), 7.24 ppm (m, 6H, —NH—CO—CH—$CH_2$—$\underline{C_6H_5}$, —NH—), 7.73 ppm (t, 1H), 8.12 ppm (broad, 1H)

Example 5-3

Synthesis of Compound (p12) ($NH_2$-E(FG-100ME)$_2$)

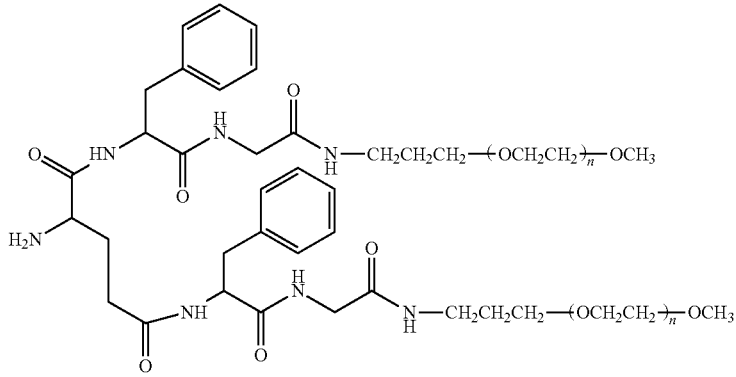

(p12)

n = about 225

By the same production method as in Example 1-3, and using L-glutamic acid with the N terminal protected by an Fmoc group (Fmoc-Glu-OH) (135 mg, $3.7 \times 10^{-4}$ mol, manufactured by WATANABE CHEMICAL INDUSTRIES, LTD.) and the compound (p11) (8.5 g, $8.5 \times 10^{-4}$ mol) obtained in Example 5-2 as starting materials, reaction and deprotection were continuously performed to give the above-mentioned compound (p12) ($NH_2$-E(FG-100ME)$_2$). yield 6.6 g. HPLC: amine purity 95%.

$^1$H-NMR ($d_6$-DMSO): 1.54 ppm (m, 2H, —NH—CO—CH($NH_2$)—$\underline{CH_2}$—$CH_2$—), 1.62 ppm (m, 4H, —CO—NH—$CH_2$—$\underline{CH_2}$—$CH_2$—), 1.97 ppm (m, 2H, —NH—CO—CH($NH_2$)—$CH_2$—$\underline{CH_2}$—), 2.74 ppm (dd, 1H, —CO—NH—CH—$\underline{CH_2}$—$C_6H_5$), 2.81 ppm (dd, 1H, —CO—NH—CH—$\underline{CH_2}$—$C_6H_5$), 3.11 ppm (m, 11H), 3.24 ppm (s, 6H, —CO—NH—$CH_2$—$CH_2$—$CH_2$—O—($CH_2$—$CH_2$—O)n-$\underline{CH_3}$), 3.64 ppm (m, about 1,800H, —CO—NH—$CH_2$—$CH_2$—$CH_2$—O—($\underline{CH_2}$—$\underline{CH_2}$—O)n-$CH_3$), 4.49 ppm (m, 1H, —CO—NH—$\underline{CH}$—$CH_2$—$C_6H_5$), 4.57 ppm (m, 1H, —CO—NH—$\underline{CH}$—$CH_2$—$C_6H_5$), 7.25 ppm (m, 10H, —CO—NH—CH—$CH_2$—$\underline{C_6H_5}$), 7.74 ppm (m, 2H), 8.44 ppm (m, 2H), 8.61 ppm (m, 2H)

Example 5-4

Synthesis of Compound (p13) (NH$_2$-E{E(FG-100ME)$_2$}$_2$)

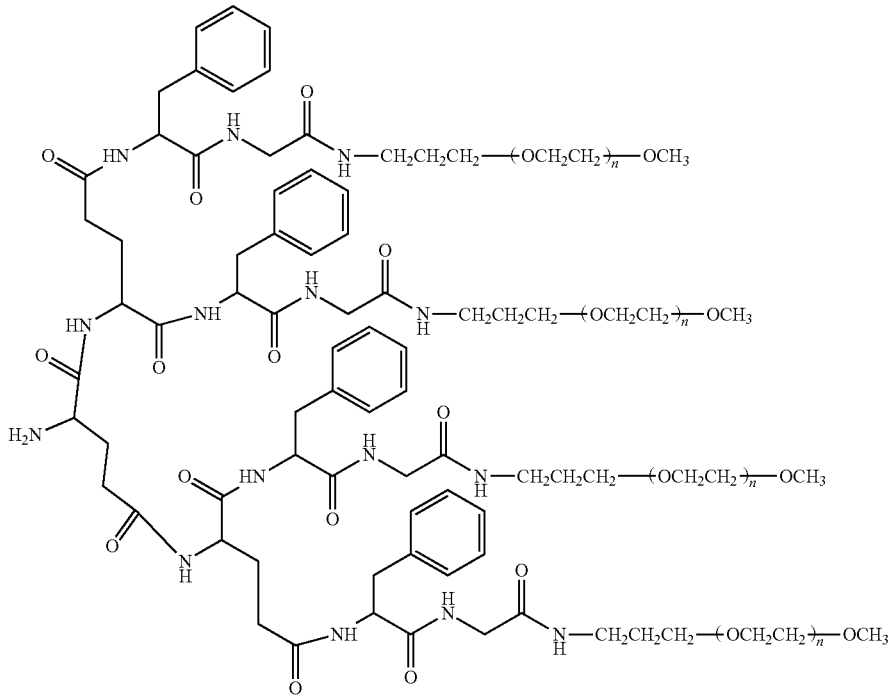

(p13)

n = about 225

By the same production method as in Example 1-3, and using L-glutamic acid with the N terminal protected by an Fmoc group (Fmoc-Glu-OH) (15.2 mg, 4.1×10$^{-5}$ mol, manufactured by WATANABE CHEMICAL INDUSTRIES, LTD.) and the compound (p12) (2.0 g, 1.0×10$^{-4}$ mol) obtained in Example 5-3 as starting materials, reaction and deprotection were continuously performed to give the above-mentioned compound (p13) (NH$_2$-E {E (FG-100ME)$_2$}$_2$). yield 1.2 g. The molecular weight is shown in Table 1. HPLC: amine purity 94%.

$^1$H-NMR (d$_6$-DMSO): 1.62 ppm (m, 14H), 2.00 ppm (m, 6H, —NH—CO—CH(NH$_2$)—CH$_2$—CH$_2$—), 2.78 ppm (m, 4H), 3.11 ppm (m, 14H), 3.24 ppm (s, 16H, —CO—NH—CH$_2$—CH$_2$—CH$_2$—O—(CH$_2$—CH$_2$—O)n-CH$_3$), 3.64 ppm (m, about 3,600H, —CO—NH—CH$_2$—CH$_2$—CH$_2$—O—(CH$_2$—CH$_2$—O)n-CH$_3$), 4.19 ppm (m, 2H), 4.51 ppm (m, 4H), 7.25 ppm (m, 20H, —CO—NH—CH—CH$_2$—C$_6$H$_5$), 7.71 ppm (m, 4H), 7.89 ppm (m, 1H), 8.45 ppm (m, 9H)

Example 6

Synthesis of Compound (p16) (NH$_2$-E(GFLG-200ME)$_2$)

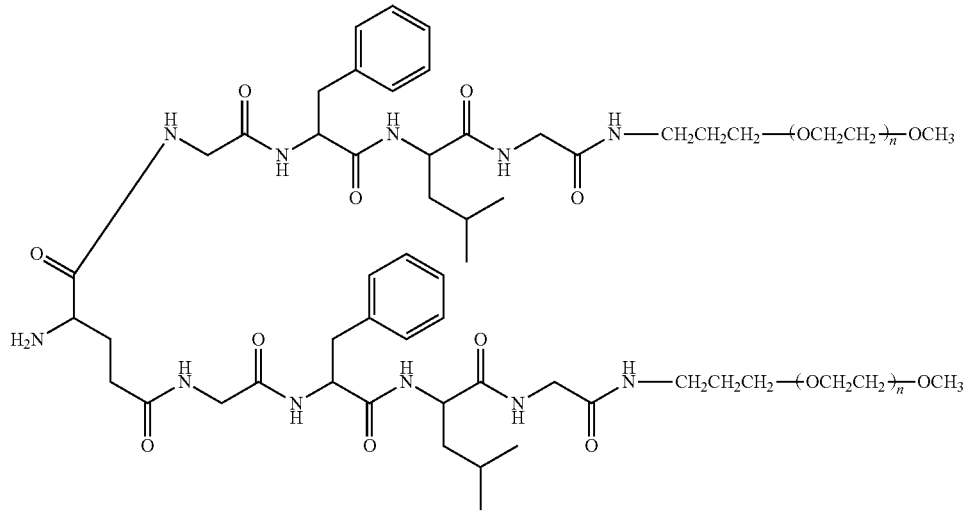

n = about 480

Example 6-1

Synthesis of Compound (p14) (ME-200GLFG-Fmoc)

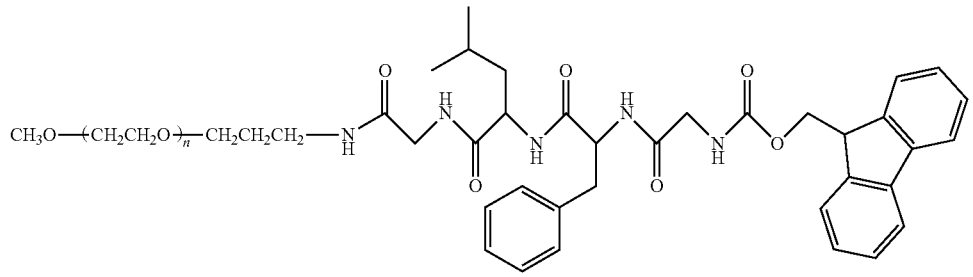

n = about 480

By the same production method as in Example 1-1, and using L-glycyl-phenylalanyl-leucyl-glycine (SEQ ID NO: 4) with the N terminal protected by an Fmoc group (Fmoc-Gly-Phe-Leu-Gly) (SEQ ID NO: 4) (66 mg, $1.1 \times 10^{-4}$ mol, manufactured by WATANABE CHEMICAL INDUSTRIES, LTD.) and methoxy PEG (1.5 g, $7.1 \times 10^{-5}$ mol, number average molecular weight=21,120, manufactured by NOF CORPORATION, "SUNBRIGHT MEPA-20T") with a propylamino group at the terminal as starting materials, the above-mentioned compound (p14) (ME-200GLFG-Fmoc) was obtained. yield 1.2 g.

$^1$H-NMR (CDCl$_3$): 0.89 ppm (d, 3H, —NH—CO—CH—CH$_2$—CH(CH$_3$)$_2$), 0.91 ppm (d, 3H, —NH—CO—CH—CH$_2$—CH(CH$_3$)$_2$), 1.53 ppm (m, 2H, —NH—CO—CH—CH$_2$—CH(CH$_3$)$_2$), 1.70 ppm (m, 1H, —NH—CO—CH—CH$_2$—CH(CH$_3$)$_2$), 1.80 ppm (m, 2H, —CO—NH—CH$_2$—CH$_2$—CH$_2$—O— (CH$_2$—CH$_2$—O)n-CH$_3$), 3.10 ppm (dd, 1H, —NH—CO—CH—CH$_2$—C$_6$H$_5$), 3.18 ppm (dd, 1H, —NH—CO—CH—CH$_2$—C$_6$H$_5$), 3.33 ppm (m, 7H), 3.74 ppm (m, about 1,900H, —CO—NH—CH$_2$—CH$_2$—CH$_2$—O—(CH$_2$—CH$_2$—O)n-CH$_3$), 4.31 ppm (broad, 1H), 4.55 ppm (t, 1H, —NH—CO—CH—CH$_2$—C$_6$H$_5$), 6.91 ppm (broad, 1H), 7.00 ppm (broad, 1H), 7.28 ppm (m, 5H, —NH—CO—CH—CH$_2$—C$_6$H$_5$), 7.33 ppm (t, 2H, Ar), 7.41 ppm (m, 3H, Ar), 7.73 ppm (m, 3H, Ar), 7.89 ppm (d, 2H, Ar), 7.98 ppm (broad, 1H)

Example 6-2

Synthesis of Compound (p15) (ME-200GLFG-NH$_2$)

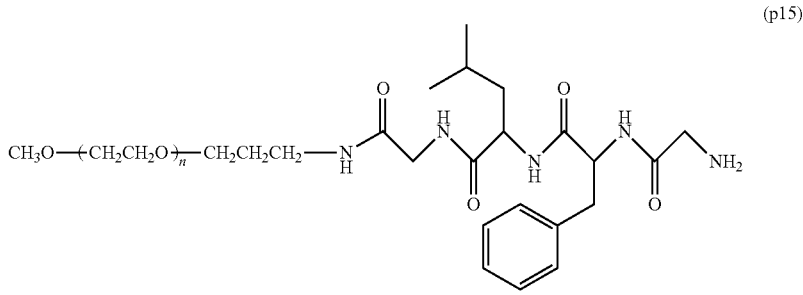

(p15)

n = about 480

By the same production method as in Example 1-2, and using the compound (p14) (1.2 g, 5.7×10$^{-5}$ mol) obtained in Example 6-1, a deprotection reaction was performed to give the above-mentioned compound (p15) (ME-200GLFG-NH$_2$). yield 1.0 g.

$^1$H-NMR (CDCl$_3$): 0.89 ppm (d, 3H, —NH—CO—CH—CH$_2$—CH(CH$_3$)$_2$), 0.91 ppm (d, 3H, —NH—CO—CH—CH$_2$—CH(CH$_3$)$_2$), 1.53 ppm (m, 2H, —NH—CO—CH—CH$_2$—CH(CH$_3$)$_2$), 1.70 ppm (m, 1H, —NH—CO—CH—CH$_2$—CH(CH$_3$)$_2$), 1.80 ppm (m, 2H, —CO—NH—CH$_2$—CH$_2$—CH$_2$—O—(CH$_2$—CH$_2$—O)n-CH$_3$), 3.10 ppm (dd, 1H, —NH—CO—CH—CH$_2$—C$_6$H$_5$), 3.18 ppm (dd, 1H, —NH—CO—CH—CH$_2$—C$_6$H$_5$), 3.33 ppm (m, 7H), 3.74 ppm (m, about 1,900H, —CO—NH—CH$_2$—CH$_2$—CH$_2$—O—(CH$_2$—CH$_2$—O)n-CH$_3$), 4.31 ppm (broad, 1H), 4.55 ppm (t, 1H, —NH—CO—CH—CH$_2$—C$_6$H$_5$), 6.91 ppm (broad, 1H), 7.00 ppm (broad, 1H), 7.28 ppm (m, 5H, —NH—CO—CH—CH$_2$—C$_6$H$_5$), 7.98 ppm (broad, 1H)

Example 6-3

Synthesis of Compound (p16) (NH$_2$-E(GFLG-200ME)$_2$)

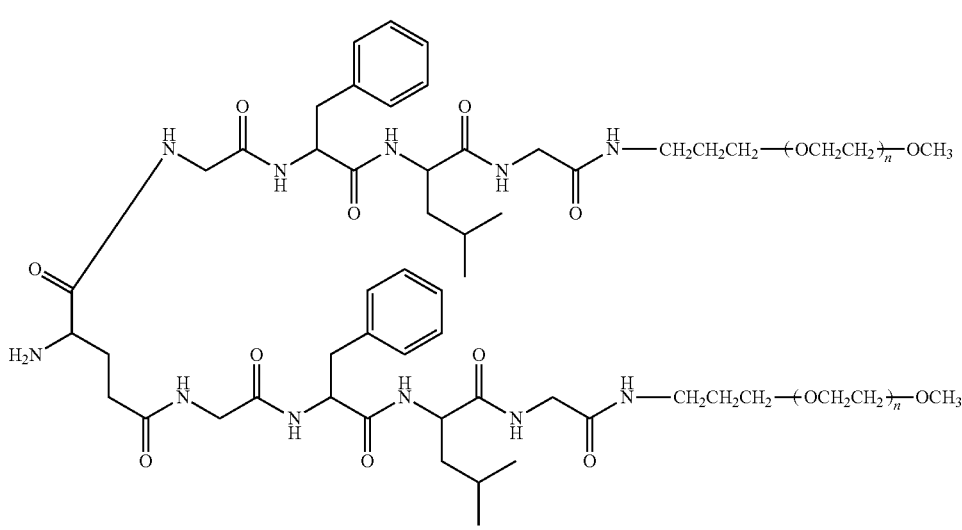

(p16)

n = about 480

By the same production method as in Example 1-3, and using L-glutamic acid with the N terminal protected by an Fmoc group (Fmoc-Glu-OH) (8.3 mg, $2.3\times10^{-5}$ mol, manufactured by WATANABE CHEMICAL INDUSTRIES, LTD.) and the compound (p15) (1.0 g, $4.8\times10^{-5}$ mol) obtained in Example 6-2 as starting materials, reaction and deprotection were continuously performed to give the above-mentioned compound (p16) ($NH_2$-E(GFLG-200ME)$_2$). yield 0.5 g. The molecular weight is shown in Table 1. HPLC: amine purity 90%.

$^1$H-NMR (CDCl$_3$): 0.89 ppm (d, 6H, —NH—CO—CH—CH$_2$—CH(CH$_3$)$_2$), 0.91 ppm (d, 6H, —NH—CO—CH—CH$_2$—CH(CH$_3$)$_2$), 1.53 ppm (m, 4H, —NH—CO—CH—CH$_2$—CH(CH$_3$)$_2$), 1.70 ppm (m, 2H, —NH—CO—CH—CH$_2$—CH(CH$_3$)$_2$), 1.77 ppm (m, 4H, —CO—NH—CH$_2$—CH$_2$—CH$_2$—O—(CH$_2$—CH$_2$—O)n-CH$_3$), 1.85 ppm (m, 1H), 3.01 ppm (m, 1H), 3.24 ppm (m, 8H), 3.38 ppm (s, 6H, —CO—NH—CH$_2$—CH$_2$—CH$_2$—O—(CH$_2$—CH$_2$—O)n-CH$_3$), 3.64 ppm (m, about 3,800H, —CO—NH—CH$_2$—CH$_2$—CH$_2$—O—(CH$_2$—CH$_2$—O)n-CH$_3$), 4.03 ppm (m, 4H), 4.14 ppm (m, 1H), 4.48 ppm (m, 2H, —CO—NH—CH—CH$_2$—C$_6$H$_5$), 6.95 ppm (broad, 1H), 7.00 ppm (broad, 1H), 7.26 ppm (m, 10H, —CO—NH—CH—CH$_2$—C$_6$H$_5$), 7.66 ppm (broad, 2H), 8.29 ppm (broad, 2H)

Comparative Example 1

Synthesis of Compound (p18) (LY-400NH$_2$)

A two-branched polyethylene glycol activation ester with lysine skeleton (3.0 g, $7.5\times10^{-5}$ mol, number average molecular weight=39,700, manufactured by NOF CORPORATION, "SUNBRIGHT LY-400NS") which is used in polyethylene glycol modifying agents on the market was dissolved in toluene (15 g) by heating at 40° C., N-(tert-butoxycarbonyl)-1,2-diaminoethane (48 μL, $3.0\times10^{-4}$ mol, manufactured by Tokyo Chemical Industry Co., Ltd.) was added, and the mixture was reacted at 40° C. under a nitrogen atmosphere for 1 hr. After completion of the reaction, the reaction solution was diluted with ethyl acetate (12 g). Hexane (14 g) was added, and the mixture was stirred at room temperature for 15 min. The resultant product was precipitated and suction filtered using 5A filter paper. The precipitate was recovered, and dissolved again in ethyl acetate (27 g). Hexane (14 g) was added, and the mixture was stirred at room temperature for 15 min. The resultant product was precipitated and suction filtered using 5A filter paper. The precipitate was recovered, washed with hexane (30 g), suction filtered using 5A filter paper, and dried in vacuo to give the above-mentioned compound (p17) (LY-400BO). yield 2.7 g.

$^1$H-NMR (CDCl$_3$): 1.37 ppm (m, 2H), 1.43 ppm (s, 9H, —CH$_2$—NH—CO$_2$—C—(CH$_3$)$_3$), 1.51 ppm (m, 2H), 3.15 ppm (m, 2H), 3.38 ppm (s, 6H, —O—(CH$_2$—CH$_2$—O)n-CH$_3$), 3.65 ppm (m, about 3,650H, —O—(CH$_2$—CH$_2$—O)n-CH$_3$), 4.21 ppm (m, 4H)

(p18)

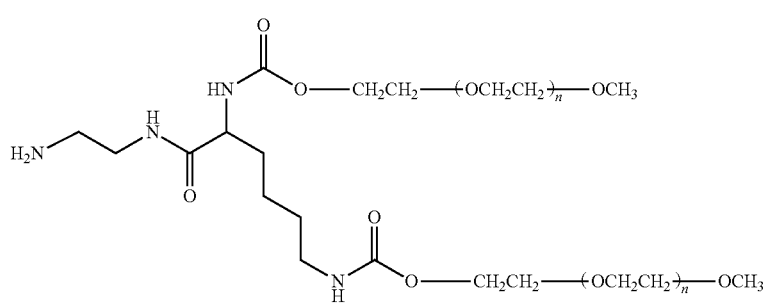

n = about 455

Comparative Example 1-1

Synthesis of Compound (p17) (LY-400BO)

(p17)

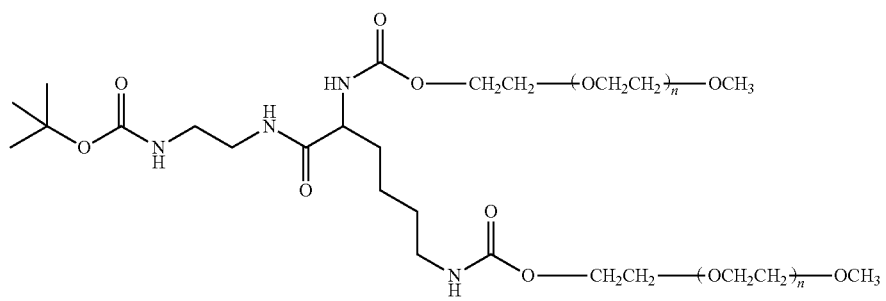

n = about 455

Comparative Example 1-2

Synthesis of Compound (p18) (LY-400NH$_2$)

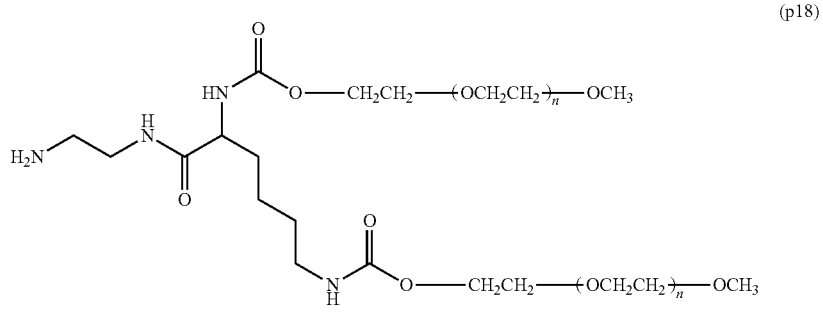

n = about 455

The compound (p17) (1.0 g, 2.5×10$^{-6}$ mol) obtained in Comparative Example 1-1 was dissolved in ion-exchanged water (4.0 g), methanesulfonic acid (57 μL, 8.8×10$^{-4}$ mol, manufactured by KANTO CHEMICAL CO., INC.) was added, and the mixture was reacted at 40° C. under a nitrogen atmosphere for 6 hr. After the reaction, the mixture was diluted with ion-exchanged water (6.0 g), 1N sodium hydroxide aqueous solution (0.9 g) was added to adjust the pH to 12, sodium chloride (2.5 g) was added and dissolved. To the obtained solution was added chloroform (10 g) containing BHT (1.0 mg), and the mixture was stirred at room temperature for 20 min. The resultant product was extracted into the organic layer. The organic layer and the aqueous layer were separated, the organic layer was recovered and concentrated at 40° C., and the obtained concentrate was diluted with toluene (30 g). Hexane (15 g) was added and the mixture was stirred at room temperature for 15 min. The resultant product was precipitated and suction filtered using 5A filter paper. The precipitate was recovered, washed with hexane (15 g) containing BHT (3.0 mg), suction filtered using 5A filter paper, and dried in vacuo to give the above-mentioned compound (p18) (LY-400NH$_2$). yield 0.7 g. The molecular weight is shown in Table 1. HPLC: amine purity 97%.

$^1$H-NMR (CDCl$_3$): 1.37 ppm (m, 2H), 1.51 ppm (m, 2H), 3.15 ppm (m, 2H), 3.38 ppm (s, 6H, —O—(CH$_2$—CH$_2$—O)n-CH$_3$), 3.65 ppm (m, about 3,650H, —O—(CH$_2$—CH$_2$—O)n-CH$_3$), 4.21 ppm (m, 4H)

TABLE 1

| sample name | molecular weight (Mn) |
|---|---|
| Example 1 | compound (p3) | 42,417 |
| Example 2 | compound (p4) | 42,534 |
| Example 3 | compound (p8) | 42,334 |
| Example 4 | compound (p9) | 42,190 |
| Example 5 | compound (p13) | 38,234 |
| Example 6 | compound (p16) | 42,398 |
| Comparative Example 1 | compound (p18) | 39,654 |

Example 7

Stability Test in Serum

Mouse or human serum (1 mL) was added to a 1.5 mL Eppendorf tube, and various polyethylene glycol derivatives were added to a concentration of 5.0 mg/mL. After incubation at 37° C. for 96 hr, 200 μL was sampled. Acetonitrile was added thereto, and the mixture was stirred by vortex for 1 min to precipitate the protein in serum. After centrifugation, the supernatant was collected. Then, to remove hydrophobic substances such as fatty acid and the like, hexane was added to the collected liquid, and the mixture was stirred by vortex for 1 min, centrifuged, and the lower layer was collected. This solution was concentrated under vacuum conditions and the polyethylene glycol derivative was recovered from the serum. Then, GPC analysis was performed and the degradation rate of the degradable polyethylene glycol derivative was calculated.

The degradation rate was calculated by the following formula.

degradation rate=(peak area % at 40 kDa before test–peak area % at 40 kDa after test)–(peak area % at 40 kDa before test)×100

The results are shown in the following Table 2.

TABLE 2

| | sample name | degradation rate in mouse serum | degradation rate in human serum |
|---|---|---|---|
| Example 1 | compound (p3) | 2% | 1% |
| Example 5 | compound (p13) | 0% | 1% |
| Example 6 | compound (p16) | 0% | 0% |
| Comparative Example 1 | compound (p18) | 0% | 1% |
| non-degradable | methoxy PEG amine 40 ka | 0% | 0% |

According to Table 2, the compounds (p3), (p13), (p16) which are degradable polyethylene glycol derivatives were not degraded in the serum, similar to compound (p18) which is a non-degradable polyethylene glycol derivative and methoxy PEG amine kDa. That is, it was shown that the degradable polyethylene glycol derivative is stable in blood.

Example 8

Degradability Test Using Cells

Using medium RPMI-1640 (10% FBS Pn/St) (10 mL), RAW264.7 was seeded at 10×10⁶ cells in a 100 mm dish, and cultured at 37° C. for 24 hr. The medium was exchanged with a medium in which various polyethylene glycol derivatives had been dissolved at a concentration of 10 mg/mL, and the cells were cultured at 37° C. for 96 hr. After culturing, the cells were lysed with 1% SDS solution, diluted with phosphate buffered saline (PBS), acetonitrile was added thereto, and the mixture was stirred for 1 min by vortex to precipitate the protein in the cell lysate, and after centrifugation, the supernatant was collected. Then, to remove hydrophobic substances such as fatty acids, hexane was added to the recovered liquid, and the mixture was stirred by vortex for 1 min, centrifuged, and the lower layer was recovered. This solution was concentrated under vacuum conditions to recover the polyethylene glycol derivative from the cells.

To confirm the degradation in the medium used for cell culture, media in which various polyethylene glycol derivatives had been dissolved at a concentration of 10 mg/mL were only cultured at 37° C. for 96 hr, and the polyethylene glycol derivative was recovered by the same operation as that described above.

Thereafter, the collected various polyethylene glycol derivatives were subjected to GPC analysis, and the degradation rate of the degradable polyethylene glycol derivative was calculated by the same calculation formula as in Example 7.

The results are shown in the following Table 3. The GPC charts before and after the cell experiment of compound (p3), (p13) are each shown in FIG. 1 and FIG. 2, and FIG. 3 and FIG. 4.

TABLE 3

|  | sample name | degradation rate in medium | degradation rate in cell |
|---|---|---|---|
| Example 1 | compound (p3) | 0% | 99% |
| Example 5 | compound (p13) | 1% | 99% |
| Example 6 | compound (p16) | 0% | 99% |
| Comparative Example 1 | compound (p18) | 0% | 0% |
| non-degradable | methoxy PEG amine 40 ka | 0% | 0% |

According to Table 3, it was confirmed that compounds (p3) and (p16) which are degradable polyethylene glycol derivatives are effectively degraded in the cells (degradation rate 99%), and effectively degraded into a molecular weight of 40,000 to 20,000. Also, it was confirmed that compound (p13) is degraded into a molecular weight of 40,000 to 10,000 at a degradation rate 99%. These degradable polyethylene glycol derivatives are not degraded in the medium used for cell culture. Thus, it was confirmed that they were specifically degraded in the cells. On the other hand, compound (p18) which is a non-degradable polyethylene glycol derivative and methoxy PEG amine 40 kDa were not degraded in the cells.

Example 9

PEGylation of Salmon Calcitonin (sCT)

salmon calcitonin (sCT) with the amino acid sequence: CSNLSTCVLG KLSQELHKLQ TYPRTNTGSG TP (SEQ ID NO: 1) (0.5 mg, 1.5×10⁻⁷ mol, manufactured by PH Japan Co., Ltd.) was dissolved in 100 mM sodium acetate buffer (pH 5.0), the compound (p8) obtained in Example 3 or methoxy PEG aldehyde 40 kDa (18 mg, 4.5×10⁻⁷ mol), and a reducing agent, 2-picolylborane (2.0×10⁻⁶ mol), were added, sCT concentration was adjusted to 1.0 mg/mL, and the mixture was reacted at 4° C. for 24 hr. Thereafter, the reaction solution was dialyzed against 10 mM sodium acetate buffer (pH 5.0), and purified by ion exchange chromatography using HiTrap SP HP (5 mL, manufactured by GE Healthcare) to give sCT-E (FG-200ME)₂ or methoxy PEG 40 kDa-sCT. The molar yield was 36% and 49%, respectively.

RPLC Analysis
  apparatus: "ALLIANCE" manufactured by WATERS
  detector: UV (280 nm)
  column: Inertsil WP300 C18 (GL Science)
  mobile phase A: 0.05% TFA-H₂O
  mobile phase B: 0.05% TFA-ACN
  gradient: changed to the order of B30% (0 min)→B40% (5 min)→B50% (15 min)→B100% (16 min)→B100% (20 min)
  flow rate: 1.0 mL/min
  column temperature: 40° C.

Figure 5:
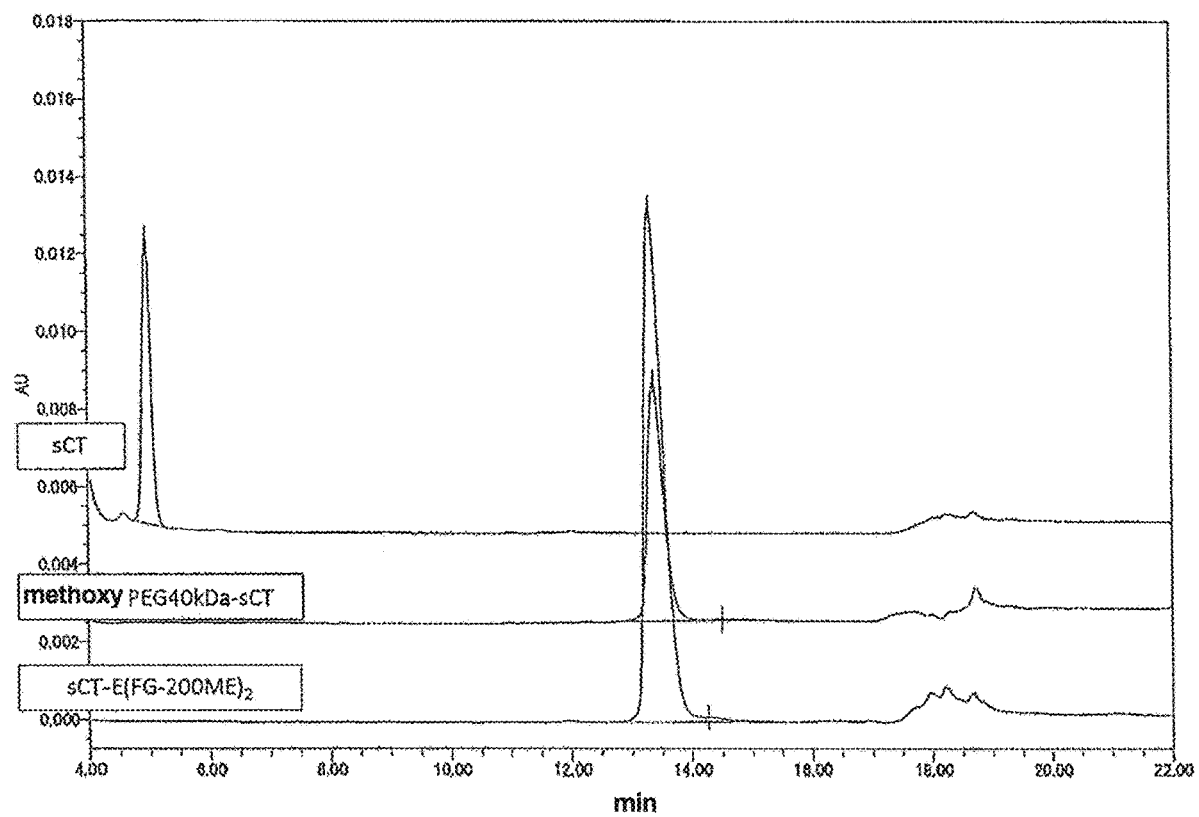
FIG. 5 shows RPLC analysis results of the conjugate (1) with salmon calcitonin, methoxy PEG 40 kDa-sCT in Example 9.

The purity of PEGylated sCT was calculated under the above-mentioned RPLC analysis conditions. The results are shown in FIG. 5.

RPLC purity of sCT-E (FG-200ME)₂ 99%
  RPLC purity of methoxy PEG 40 kDa-sCT 99%

MALDI-TOF-MS Analysis
  apparatus: "autoflex3" manufactured by Bruker
  sample: 0.5 mg/mL, PBS solution
  matrix: saturated α-cyano-4-hydroxycinnamic acid (CHCA) solution (0.01% TFA-H₂O:ACN=2:1)

The sample (1 μL) and matrix (19 μL) were mixed and 1 L was spotted on the target.

The molecular weight of the starting material PEG and PEGylated sCT was measured under the above-mentioned MALDI-TOF-MS analysis conditions.

Figure 6:
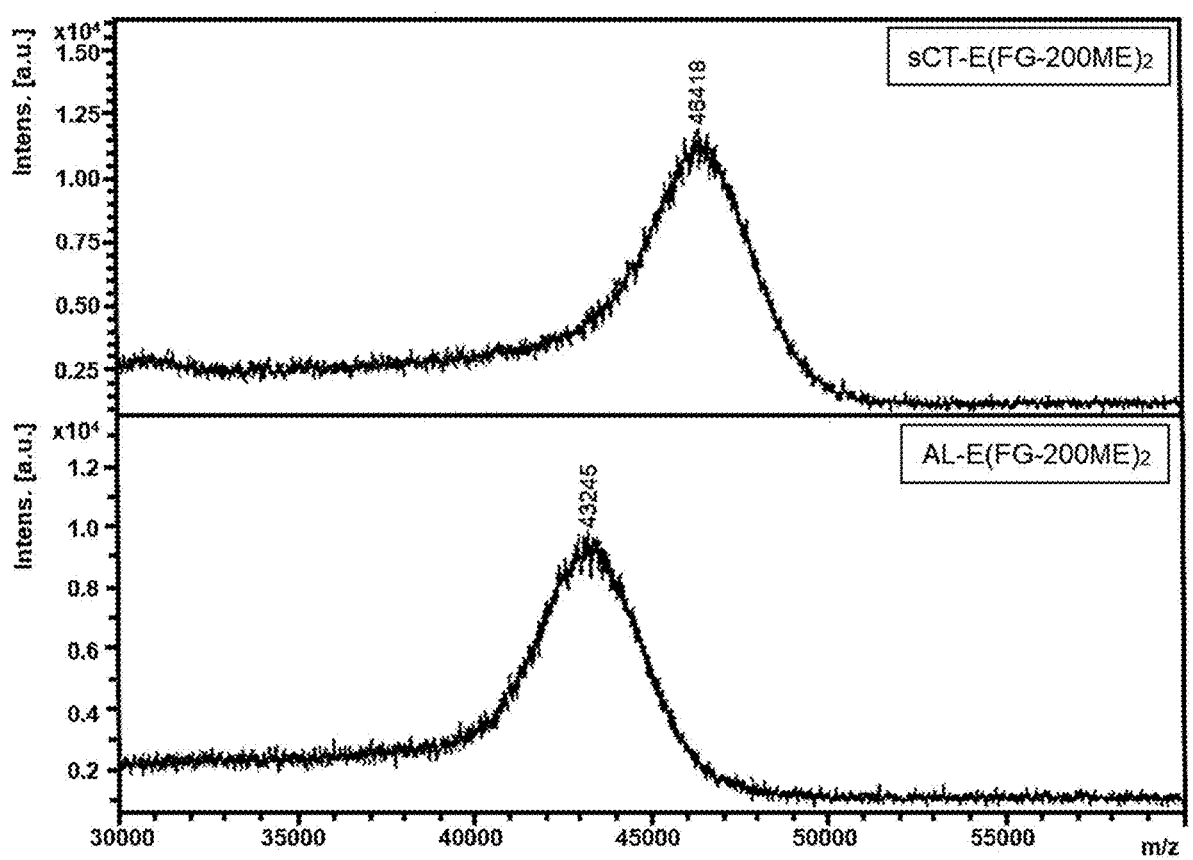
FIG. 6 shows MALDI-TOF-MS analysis results of the compound (p8) obtained in Example 3 and the conjugate (1) obtained in Example 9.

FIG. 6 concurrently shows the results of MALDI-TOF-MS of the compound (p8) as the starting material and sCT-E(FG-200ME)₂. molecular weight of sCT-E(FG-200ME)₂ 46,405 molecular weight of compound (p8) 43,136

Figure 7:
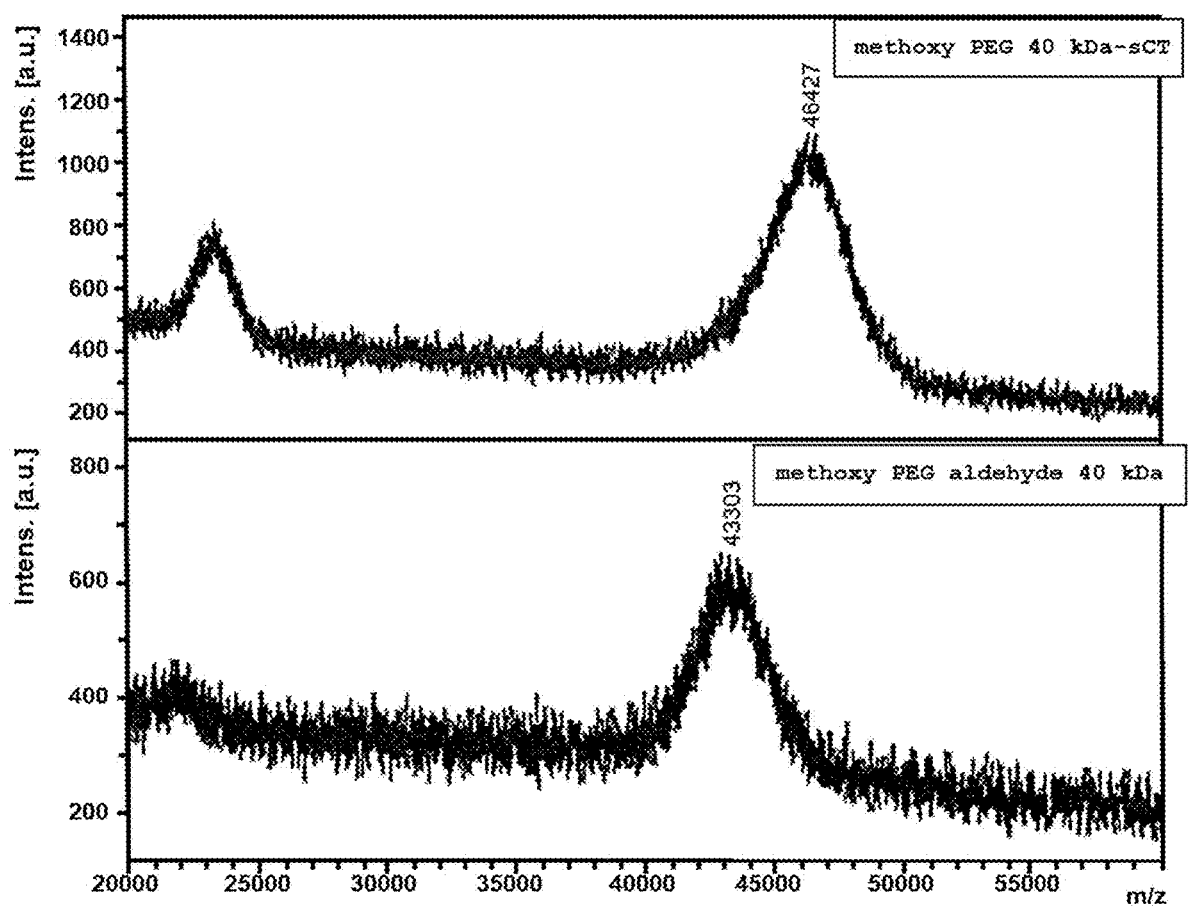
FIG. 7 shows MALDI-TOF-MS analysis results of methoxy PEG aldehyde 40 kDa and methoxy PEG 40 kDa-sCT obtained in Example 9.

FIG. 7 concurrently shows the results of MALDI-TOF-MS of the starting material methoxy PEG aldehyde 40 kDa and methoxy PEG 40 kDa-sCT.

molecular weight of methoxy PEG 40 kDa-sCT 46,427
  molecular weight of methoxy PEG aldehyde 40 kDa 43,303

According to FIG. 7, it could be confirmed that the molecular weight of PEGylated sCT increased by about the molecular weight of sCT compared to the molecular weight of the starting material, PEG derivative.

SDS-PAGE Analysis
  kit: NuPAGE (registered trade mark) Bis-Tris Precast Gel (gel concentration 4-12%) manufactured by Thermo Fisher Scientific
  staining solution: Coomassie brilliant blue solution (CBB solution) or iodine staining solution (BaCl₂+I₂ solution)

Figure 8:
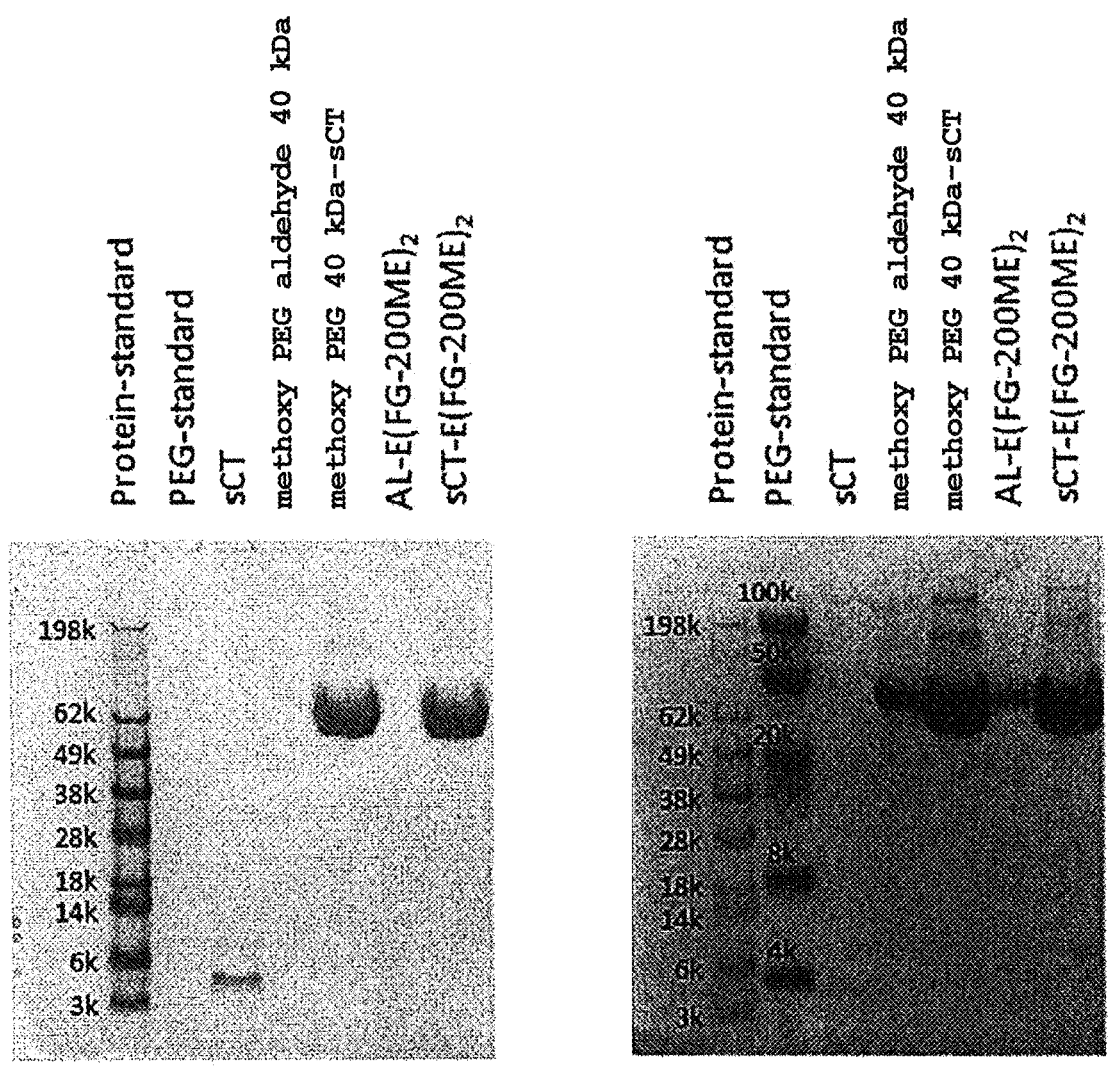
FIG. 8 shows SDS-PAGE analysis results of the conjugate (1) with salmon calcitonin, methoxy PEG 40 kDa-sCT in Example 9 (left figure: CBB staining, right figure: iodine staining).

The PEGylated sCT was evaluated according to the recommended measurement conditions of the above-mentioned SDS-PAGE kit. The results are shown in FIG. 8. According to FIG. 8, in PEGylated sCT, a band was observed by CBB staining that selectively stains proteins and peptides, and a band was also observed by iodine staining that stains polyethylene glycol. Bands were seen in both stains, thus confirming that the polyethylene glycol derivative was bonded to sCT.

Example 10

PEGylation of Human Growth Hormone (hGH)
Human growth hormone (hGH) with the amino acid sequence:

(SEQ ID NO: 2)
MFPTIPLSRL FDNAMLRAHR LHQLAFDTYQ EFEEAYIPKE

QKYSFLQNPQ TSLCFSESIP TPSNREETQQ KSNLELLRIS

LLLIQSWLEP VQFLRSVFAN SLVYGASDSN VYDLLKDLEE

GIQTLMGRLE DGSPRTGQIF KQTYSKFDTN SHNDDALLKN

YGLLYCFRKD MDKVETFLRI VQCRSVEGSC GF (0.4 mg, $1.8 \times 10^{-8}$ mol, manufactured by Shenandoah Biotechnology) was dissolved in 100 mM sodium acetate buffer (pH 5.5), the compound (p8) obtained in Example 3 or methoxy PEG aldehyde 40 kDa (3.6 mg, $9.0 \times 10^{-8}$ mol), and a reducing agent, sodium cyanoborohydride ($9.0 \times 10^{-7}$ mol) were added, hGH concentration was adjusted to 1.0 mg/mL, and the mixture was reacted at 25° C. for 24 hr. Thereafter, the reaction solution was dialyzed against 10 mM sodium acetate buffer (pH 4.7), and purified by ion exchange chromatography using HiTrap SP HP (5 mL, manufactured by GE Healthcare) to give hGH-E(FG-200ME)$_2$ or methoxy PEG 40 kDa-hGH. The molar yield was 28% and 32%, respectively.
RPLC analysis
    apparatus: "ALLIANCE" manufactured by WATERS
    detector: UV (280 nm)
    column: Inertsil WP300 C18 (GL Science)
    mobile phase A: 0.1% TFA-H$_2$O
    mobile phase B: 0.1% TFA-ACN
    gradient: changed to the order of B40% (0 min)→B80% (25 min)→B90% (27 min)→B40% (27.1 min)
    flow rate: 1.0 mL/min
    column temperature: 25° C.

Figure 9:
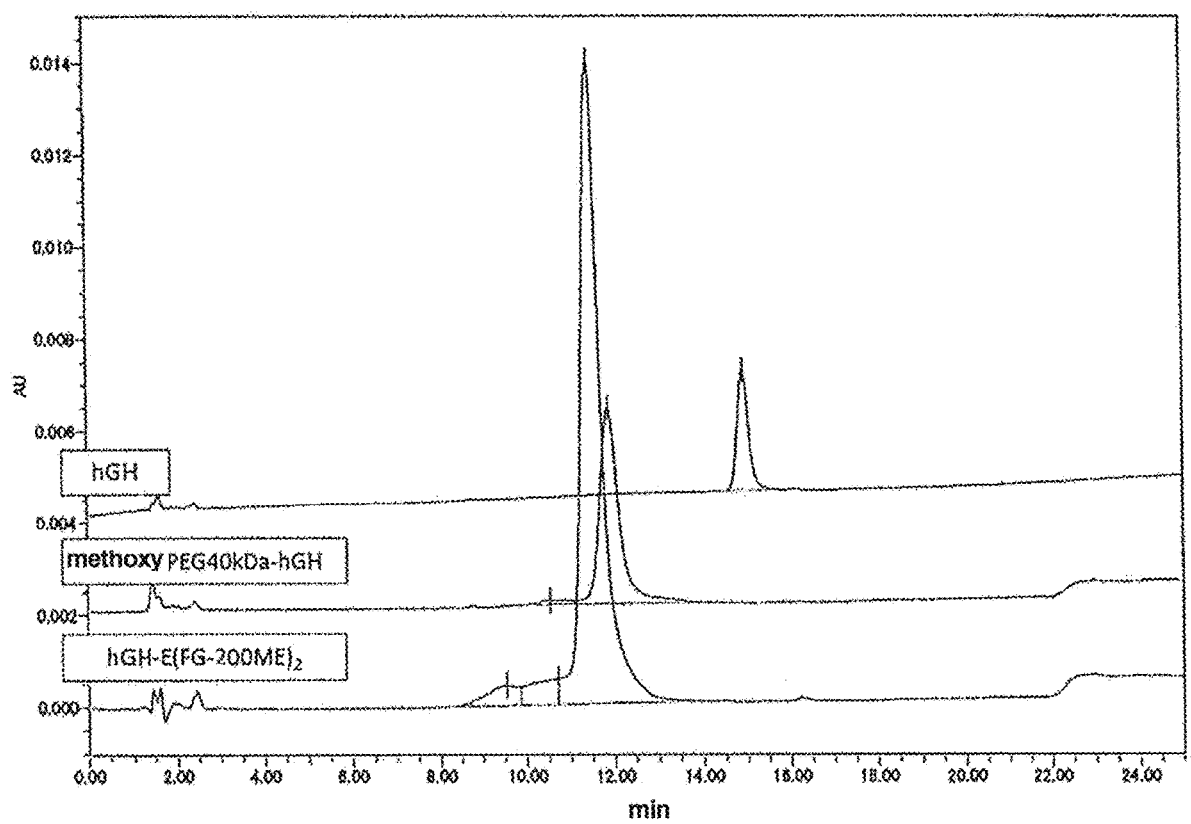
FIG. 9 shows RPLC analysis results of and the conjugate (2) with human growth hormone, methoxy PEG 40 kDa-hGH in Example 10.

The purity of PEGylated hGH was calculated under the above-mentioned RPLC analysis conditions. The results are shown in FIG. 9.
    RPLC purity of hGH-E(FG-200ME)$_2$ 90%
    RPLC purity of methoxy PEG 40 kDa-hGH 97%
MALDI-TOF-MS Analysis
    apparatus: "autoflex3" manufactured by Bruker
    sample: 0.5 mg/mL, PBS solution
    matrix: saturated cinnamic acid (SA) solution (0.01% TFA-H$_2$O:ACN=2:1)

The sample (1 μL) and matrix (19 μL) were mixed and 1 μL was spotted on the target.

The molecular weight of PEGylated hGH was measured under the above-mentioned MALDI-TOF-MS analysis conditions. The results are shown in FIG. 10 and FIG. 11. molecular weight of hGH-E(FG-200ME)$_2$ 65,584 molecular weight of methoxy PEG 40 kDa-hGH 65,263

Figure 10:
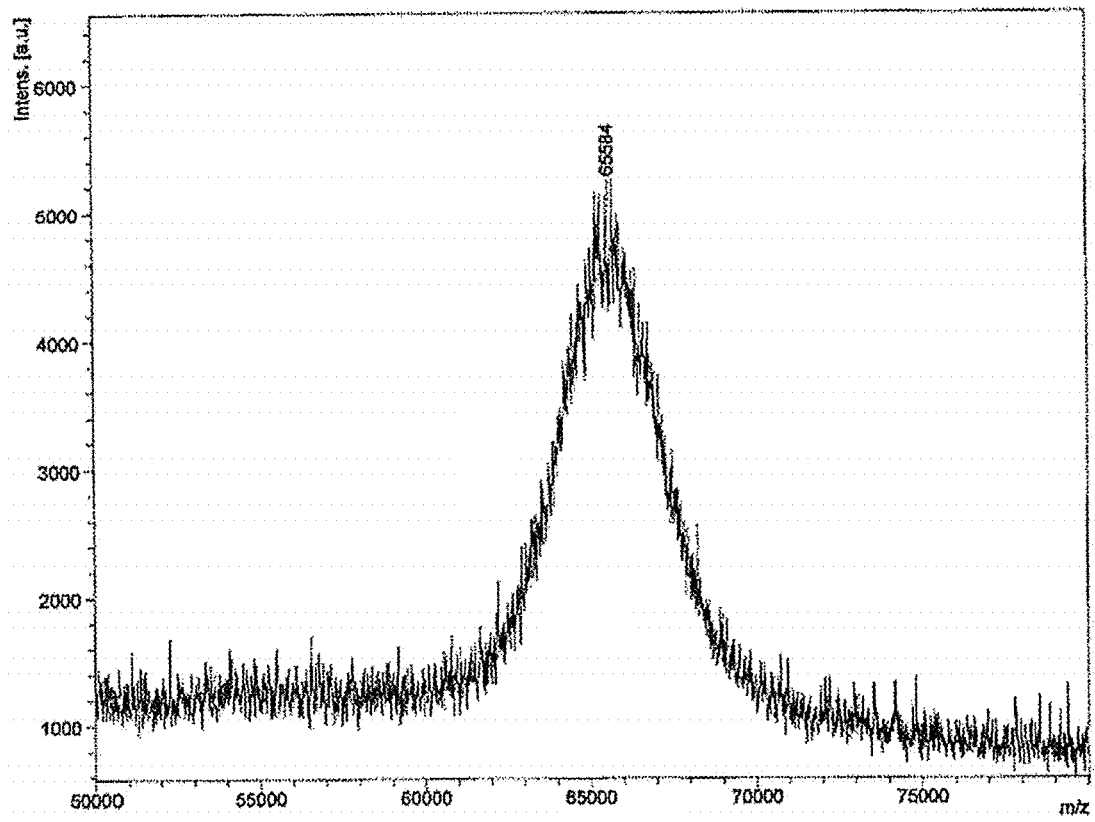
FIG. 10 shows MALDI-TOF-MS analysis results of the conjugate (2) with human growth hormone in Example 10.
Figure 11:
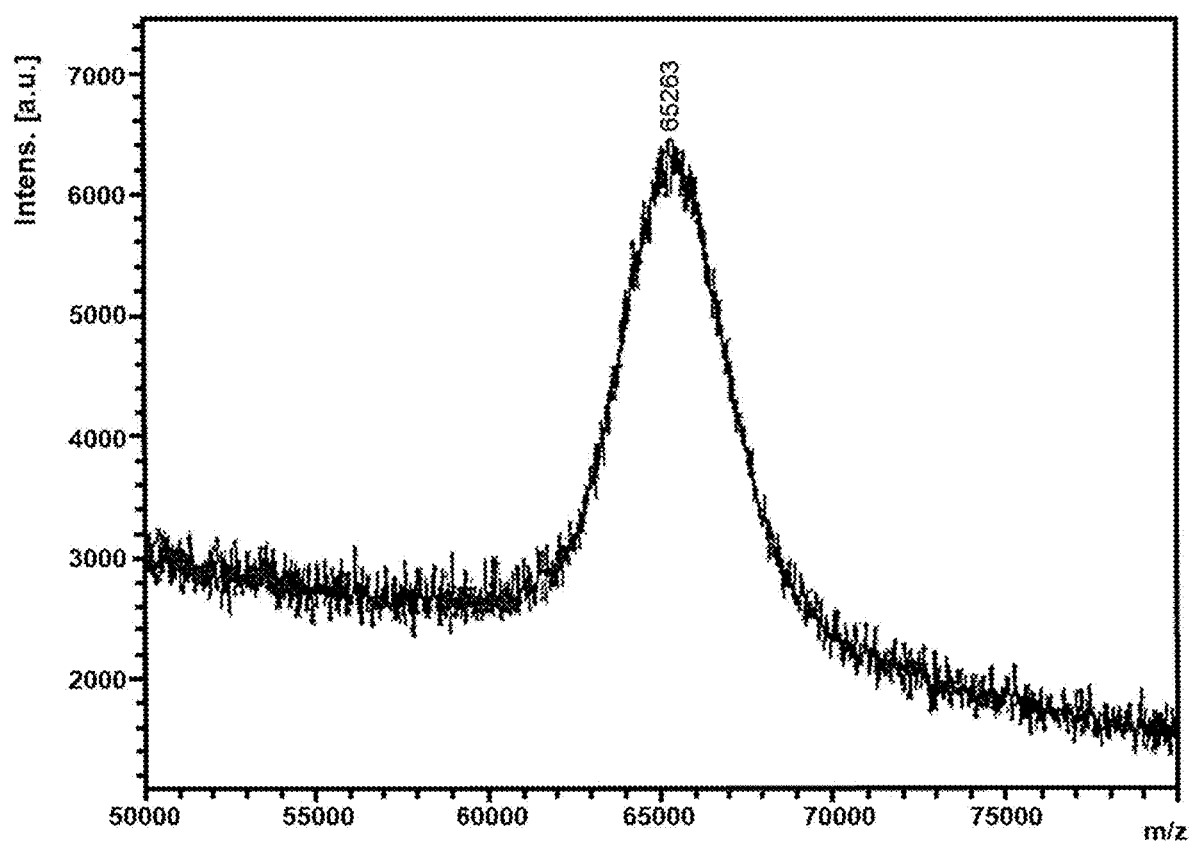
FIG. 11 shows MALDI-TOF-MS analysis results of human growth hormone and methoxy PEG aldehyde 40 kDa in Example 10.

According to FIG. 10 and FIG. 11, it was confirmed that the molecular weight of PEGylated hGH increased by about the molecular weight of hGH compared to the molecular weight of the starting material, PEG derivative (see FIG. 6 and lower drawing of FIG. 7).

SDS-PAGE Analysis
    kit: NuPAGE (registered trade mark) Bis-Tris Precast Gel (gel concentration 4-12%) manufactured by Thermo Fisher Scientific
    staining solution: Coomassie brilliant blue solution (CBB solution) or iodine staining solution (BaCl$_2$+I$_2$ solution)

Figure 12:
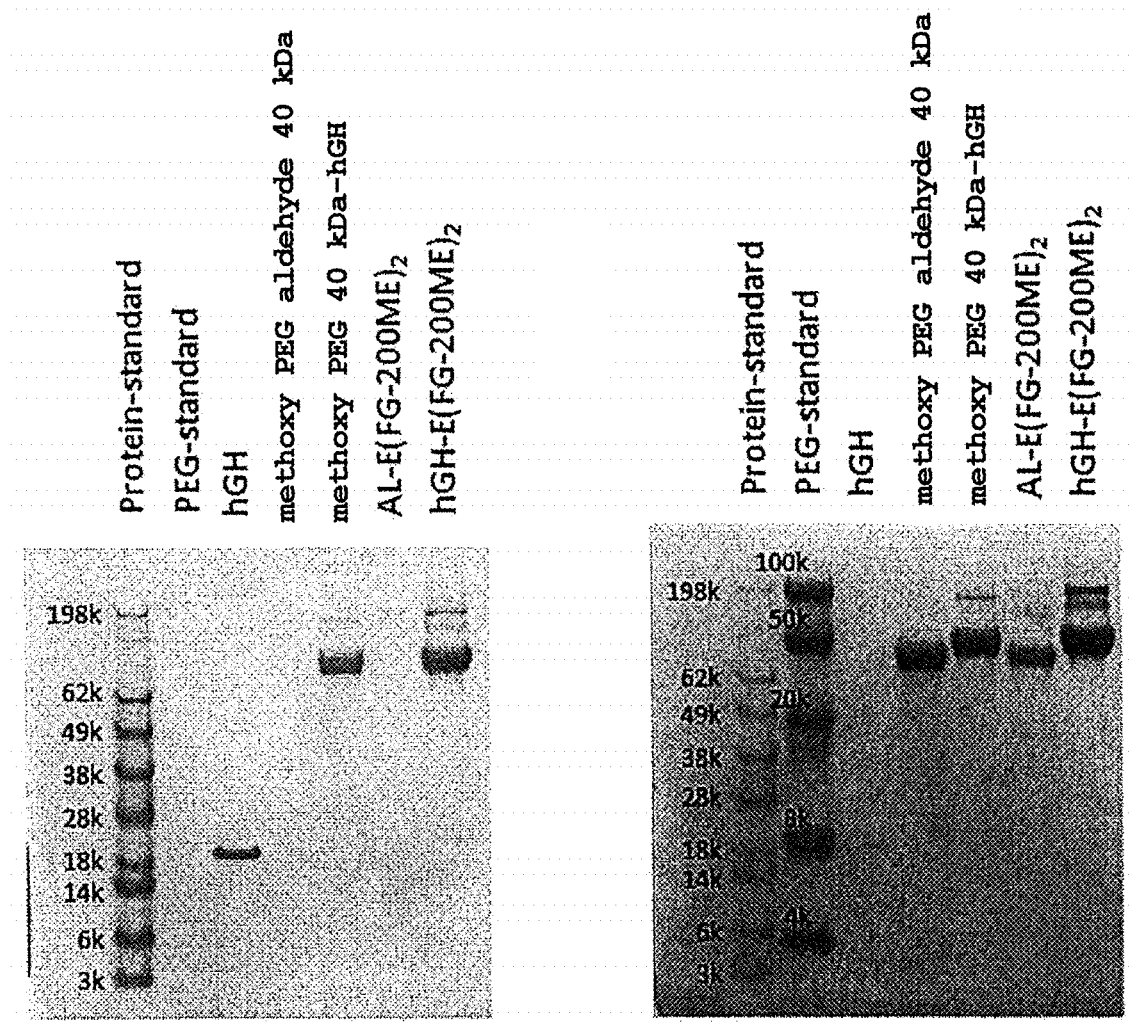
FIG. 12 shows SDS-PAGE analysis results of the conjugate (2) with human growth hormone, methoxy PEG 40 kDa-hGH in Example 10 (left figure: CBB staining, right figure: iodine staining).

The PEGylated hGH was evaluated according to the recommended measurement conditions of the above-mentioned SDS-PAGE kit. The results are shown in FIG. 12. According to FIG. 12, in PEGylated hGH, a band was observed by CBB staining that selectively stains proteins and peptides, and a band was also observed by iodine staining that stains polyethylene glycol. Bands were seen in both stains, thus confirming that the polyethylene glycol derivative was bonded to hGH.

Example 11

PEGylation of Granulocyte Colony Stimulating Factor (GCSF)
A granulocyte colony stimulating factor (GCSF) with the amino acid sequence: TPLGPASSLP QSFLLKCLEQ VRKIQGDGAA LQEKLCATYK LCHPEELVLL GHSL-GIPWAP LSSCPSQALQ LAGCLSQLHS GLFLYQGLLQ ALEGISPELG PTLDTLQLDV ADFATTIWQQ MEELG-MAPAL QPTQGAMPAF ASAFQRRAGG VLVASHLQSF LEVSYRVLRH LAQP (SEQ ID NO: 3) (0.1 mg, $5.3 \times 10^{-9}$ mol, manufactured by PeproTech) was dissolved in 10 mM sodium acetate buffer (pH 4.6, containing 5% sorbitol), the compound (p8) obtained in Example 3 and a reducing agent, sodium cyanoborohydride ($5.3 \times 10^{-7}$ mol) were added, GCSF concentration was adjusted to 2.0 mg/mL, and the mixture was reacted at 4° C. for 24 hr. Thereafter, the reaction solution was diluted with 10 mM sodium acetate buffer (pH 4.6), and purified by ion exchange chromatography using HiTrap SP HP (5 mL, manufactured by GE Healthcare) to give GCSF-E(FG-200ME)$_2$. molar yield 41%.
RPLC Analysis
    apparatus: "ALLIANCE" manufactured by WATERS
    detector: UV (280 nm)
    column: Inertsil WP300 C18 (GL Science)
    mobile phase A: 0.1% TFA-H$_2$O
    mobile phase B: 0.1% TFA-ACN
    gradient: changed to the order of B40% (0 min)→B70% (25 min)→B90% (27 min)→B40% (29 min)
    flow rate: 1.0 mL/min
    column temperature: 40° C.

The purity of PEGylated GCSF was calculated under the above-mentioned RPLC analysis conditions.
    RPLC purity of GCSF-E(FG-200ME)$_2$ 97%
MALDI-TOF-MS Analysis
    apparatus: "autoflex3" manufactured by Bruker
    sample: 0.5 mg/mL, PBS solution
    matrix: saturated cinnamic acid (SA) solution (0.01% TFA-H$_2$O:ACN=2:1)

The sample (1 μL) and matrix (19 μL) were mixed and 1 L was spotted on the target.

The molecular weight of PEGylated GCSF was measured under the above-mentioned MALDI-TOF-MS analysis conditions. molecular weight of GCSF-E(FG-200ME)$_2$ 62,199

According to the above-mentioned MALDI-TOF-MS analysis results, it could be confirmed that the molecular weight of PEGylated GCSF increased by about the molecular weight of GCSF compared to the molecular weight of the starting material, PEG derivative.

SDS-PAGE Analysis kit: NuPAGE (registered trade mark) Bis-Tris Precast Gel (gel concentration 4-12%) manufactured by Thermo Fisher Scientific staining solution: Coomassie brilliant blue solution (CBB solution) or iodine staining solution ($BaCl_2+I_2$ solution)

The PEGylated GCSF was evaluated according to the recommended measurement conditions of the above-mentioned SDS-PAGE kit. According to the above-mentioned SDS-PAGE analysis results, in PEGylated GCSF, a band was observed by CBB staining that selectively stains proteins and peptides, and a band was also observed by iodine staining that stains polyethylene glycol. Bands were seen in both stains, thus confirming that the polyethylene glycol derivative was bonded to GCSF.

Example 12

Evaluation of Physiological Activity of PEGylated Salmon Calcitonin (sCT)

The physiological activities of 4 groups of sCT-E(FG-200ME)$_2$ which is SCT to which degradable polyethylene glycol derivative with a molecular weight of 40,000 is bonded and methoxy PEG 40 kDa-sCT, in which non-degradable methoxy PEG 40 kDa is bonded, each of which is obtained in Example 9, unmodified sCT, and PBS were comparatively evaluated in animal experiments. Mouse strain was Balb/c (8-week-old, male), PEGylated sCT solution and unmodified sCT solution were prepared to achieve sCT concentration of 8.0 g/mL with PBS, and administered at a sCT dose of 40 g/kg. Blood was collected to obtain plasma from the mice at 1, 6, 24 hr, and calcium concentration was measured using calcium E-Test Wako (manufactured by FUJIFILM Wako Pure Chemical Industries, Ltd.). The results thereof are shown in FIG. 16.

Figure 16:
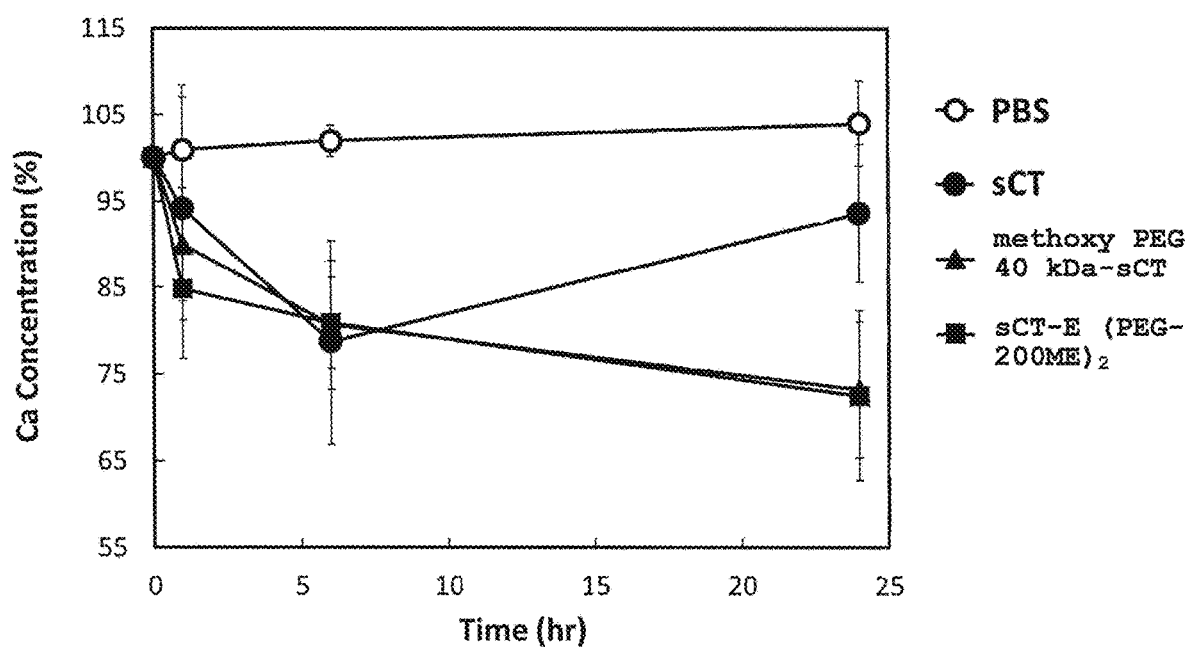
FIG. 16 shows evaluation results of the physiological activity (blood calcium concentration) of salmon calcitonin and PEGylated salmon calcitonin in Example 12.

According to FIG. 16, all sCTs significantly reduced calcium concentration as compared to the PBS group. Unmodified sCT showed an increase in calcium concentration from 6 hr after administration. It was found that a low calcium concentration was continuously maintained in sCT-E(FG-200ME)$_2$ and methoxy PEG kDa-sCT. It was confirmed that PEGylation prolonged the half-life in blood of sCT and the physiological activity was maintained without impairment.

Example 13

Vacuole Formation Evaluation Test by Animal Experiment

Figure 13:
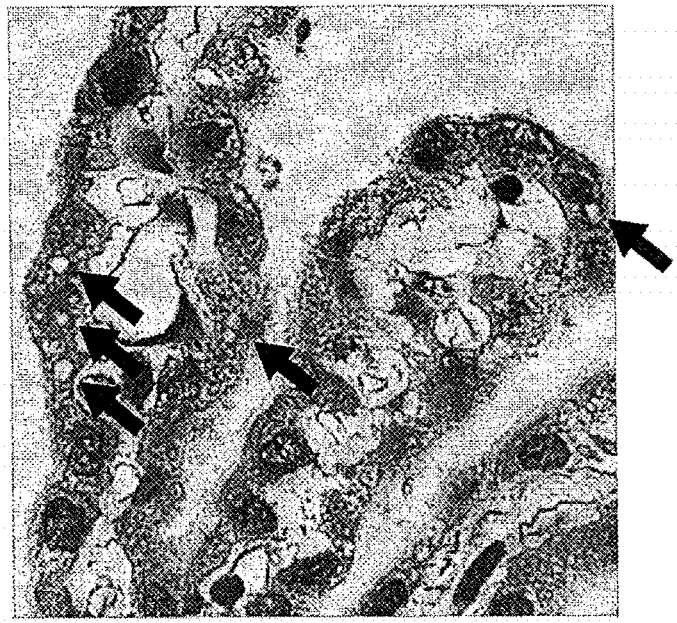
FIG. 13 shows an image of a section of cerebral choroid plexus of a mouse that received long-term administration of methoxy PEG amine 40 kDa in Example 13 (arrows show vacuoles).
Figure 14:
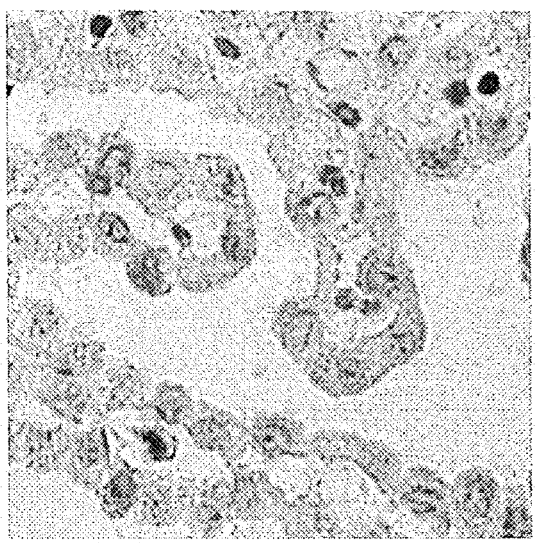
FIG. 14 shows an image of a section of cerebral choroid plexus of a mouse that received long-term administration of the compound (p3) (NH$_2$-E(FG-200ME)$_2$) in Example 13.

Using compound (p3)NH$_2$-E(FG-200ME)$_2$ which is a degradable polyethylene glycol derivative with a molecular weight of 40,000 and having an amino group at the terminal, and non-degradable methoxy PEG amine 40 kDa, vacuole formation was evaluated by an animal experiment. Mouse strain was Balb/c (8-week-old, male) and, as a polyethylene glycol solution, a polyethylene glycol derivative was prepared at a concentration of 100 mg/mL using physiological saline, and 20 μL was administered from the mouse tail vein. The administration was continued 3 times a week continuously for 4 weeks. After the completion of administration, the mice were perfused and fixed with a 4% aqueous paraformaldehyde solution to prepare paraffin sections. HE staining and immunostaining with anti-PEG antibody were performed to evaluate vacuole formation in choroid plexus epithelial cells of the brain. Immunostaining was performed using an immunostaining kit (BOND Refine Polymer Detection Kit, manufactured by Leica) and an anti-PEG antibody (B-47 antibody, manufactured by Abcam). Images of choroid plexus sections of the brain immunostained with anti-PEG antibody are shown in FIG. 13 (methoxy PEG amine 40 kDa) and FIG. 14 (NH$_2$-E(FG-200ME)$_2$)

As a result, NH$_2$-E(FG-200ME)$_2$ which is a degradable polyethylene glycol significantly suppressed vacuole formation as compared with methoxy PEG amine 40 kDa.

The amount of polyethylene glycol administered in this Example is an amount optimized to evaluate vacuolation, and extremely large compared with the dose of polyethylene glycol that is generally used in the art.

Example 14

Accumulation Evaluation Test of Polyethylene Glycol by Animal Experiment

Using compound (p3)NH$_2$-E(FG-200ME)$_2$ which is a degradable polyethylene glycol derivative with a molecular weight of 40,000 and having an amino group at the terminal, and non-degradable methoxy PEG amine 20 kDa, non-degradable methoxy PEG amine 40 kDa, and PBS as a control, accumulation of polyethylene glycol was evaluated by an animal experiment. Mouse strain was Balb/c (8-week-old, male) and, as a polyethylene glycol solution, a polyethylene glycol derivative was prepared at a concentration of 62.5 mg/mL using physiological saline, and 100 μL was administered from the mouse tail vein. The administration was continued 3 times a week continuously for 4 weeks. After the completion of administration, the mice were perfused and fixed with a 4% aqueous paraformaldehyde solution to prepare paraffin sections. Immunostaining with anti-PEG antibody was performed to evaluate accumulation in choroid plexus epithelial cells of the brain. Images of each immunostained choroid plexus section of the brain are shown in FIG. 15.

Figure 15:
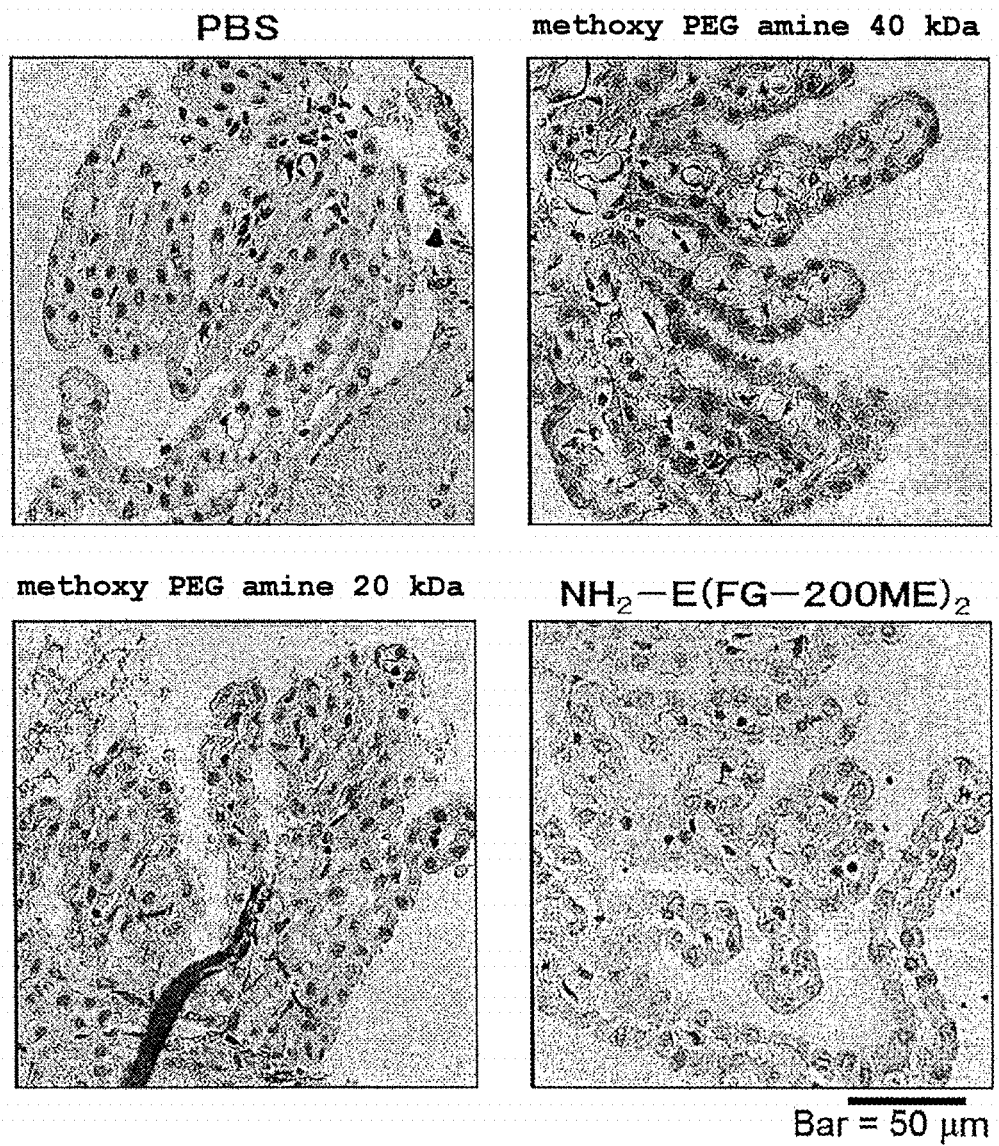
FIG. 15 shows images of sections of cerebral choroid plexus of mice that received long-term administration of PBS, methoxy PEG amine 40 kDa, methoxy PEG amine 20 kDa, and the compound (p3) (NH$_2$-E(FG-200ME)$_2$) in Example 14 (stained part shows accumulation of PEG).

According to FIG. 15, it was confirmed that choroid plexus section of mice administered with PBS without containing polyethylene glycol was not stained, whereas brown staining was observed over a wide area of the section with non-degradable methoxy PEG amine 40 kDa. The stained portion shows accumulation of PEG. On the other hand, in the section of NH$_2$-E(FG-200ME)$_2$ which is degradable polyethylene glycol a brown-stained portion is small, and accumulation was equivalent to that of methoxy PEG amine 20 kDa with a half molecular weight. Due to the degradability, degradable polyethylene glycol significantly suppressed the accumulation of polyethylene glycol in tissues as compared with non-degradable methoxy PEG amine 40 kDa having the same molecular weight.

The amount of polyethylene glycol administered in this Example is an amount optimized to evaluate accumulation, and extremely large compared with the dose of polyethylene glycol that is generally used in the art.

INDUSTRIAL APPLICABILITY

The degradable polyethylene glycol derivative of the present invention is a high-molecular-weight polyethylene glycol derivative that does not cause vacuolation of cells, can be effectively used for modifying bio-related substances, is stable in the blood of living organisms, and is degraded in cells.

This application is based on patent application No. 2019-069450 filed in Japan (filing date: Mar. 29, 2019), the contents of which are encompassed in full herein.

The invention claimed is:

1. A degradable polyethylene glycol derivative-bonded bio-related substance of formula (2), formula (3), or formula (4):

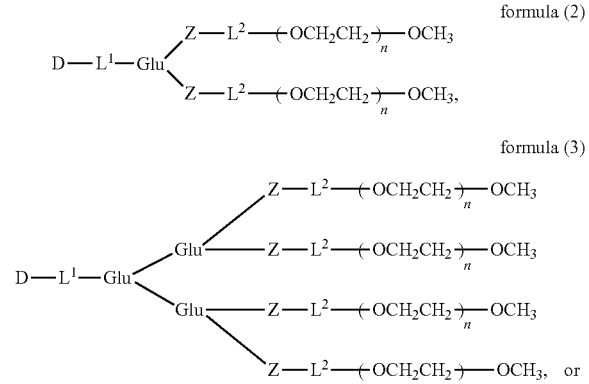

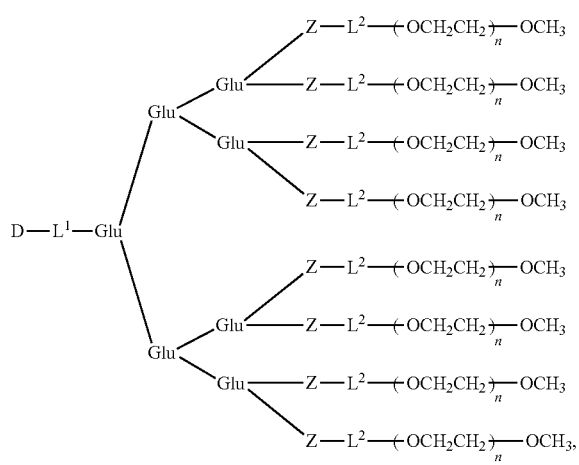

wherein
D is a bio-related substance;
Glu is a glutamic acid residue;

Z is a degradable oligopeptide selected from the group consisting of glycine-phenylalanine-leucine-glycine (SEQ ID NO: 4), glycine-glycine-phenylalanine-glycine (SEQ ID NO: 5), glycine-phenylalanine-glycine, glycine-leucine-glycine, valine-citrulline-glycine, valine-alanine-glycine, and phenylalanine-glycine;

$L^1$ and $L^2$ are each independently a divalent spacer; and n is 220-460.

2. The bio-related substance according to claim 1, wherein the molecular weight of the degradable polyethylene glycol derivative is 20,000-80,000 Daltons.

3. The bio-related substance according to claim 1, wherein $L^1$ is a urethane bond, an amide bond, an ether bond, a thioether bond, a secondary amino group, a carbonyl group, a urea bond, a triazolyl group, an oxime bond, or a bond of maleimide or mercapto; or an alkylene group optionally comprising a urethane bond, an amide bond, an ether bond, a thioether bond, a secondary amino group, a carbonyl group, a urea bond, a triazolyl group, an oxime bond, or a bond of maleimide or mercapto.

4. The bio-related substance according to claim 1, wherein $L^2$ is an alkylene group; or an alkylene group comprising at least one bond and/or group selected from a urethane bond, an amide bond, an ether bond, a thioether bond, a secondary amino group, a carbonyl group, and a urea bond.

5. The bio-related substance according to claim 1, wherein the bio-related substance for D is a hormone, a cytokine, an antibody, an aptamer or an enzyme.

6. The bio-related substance according to claim 1, wherein Z is glycine-phenylalanine-leucine-glycine (SEQ ID NO: 4).

7. The bio-related substance according to claim 1, wherein Z is glycine-glycine-phenylalanine-glycine (SEQ ID NO: 5).

8. The bio-related substance according to claim 1, wherein Z is glycine-phenylalanine-glycine.

9. The bio-related substance according to claim 1, wherein Z is glycine-leucine-glycine.

10. The bio-related substance according to claim 1, wherein Z is valine-citrulline-glycine.

11. The bio-related substance according to claim 1, wherein Z is valine-alanine-glycine.

12. The bio-related substance according to claim 1, wherein Z is phenylalanine-glycine.

* * * * *

SEQUENCE LISTING

<160> NUMBER OF SEQ ID NOS: 5

<210> SEQ ID NO 1
<211> LENGTH: 32
<212> TYPE: PRT
<213> ORGANISM: Oncorhynchus keta

<400> SEQUENCE: 1

Cys Ser Asn Leu Ser Thr Cys Val Leu Gly Lys Leu Ser Gln Glu Leu
1               5                   10                  15

His Lys Leu Gln Thr Tyr Pro Arg Thr Asn Thr Gly Ser Gly Thr Pro
            20                  25                  30

<210> SEQ ID NO 2
<211> LENGTH: 192
<212> TYPE: PRT
<213> ORGANISM: Homo sapiens

<400> SEQUENCE: 2

Met Phe Pro Thr Ile Pro Leu Ser Arg Leu Phe Asp Asn Ala Met Leu
1               5                   10                  15

Arg Ala His Arg Leu His Gln Leu Ala Phe Asp Thr Tyr Gln Glu Phe
            20                  25                  30

Glu Glu Ala Tyr Ile Pro Lys Glu Gln Lys Tyr Ser Phe Leu Gln Asn
        35                  40                  45

Pro Gln Thr Ser Leu Cys Phe Ser Glu Ser Ile Pro Thr Pro Ser Asn
    50                  55                  60

Arg Glu Glu Thr Gln Gln Lys Ser Asn Leu Glu Leu Leu Arg Ile Ser
65                  70                  75                  80

Leu Leu Leu Ile Gln Ser Trp Leu Glu Pro Val Gln Phe Leu Arg Ser
                85                  90                  95

Val Phe Ala Asn Ser Leu Val Tyr Gly Ala Ser Asp Ser Asn Val Tyr
            100                 105                 110

Asp Leu Leu Lys Asp Leu Glu Glu Gly Ile Gln Thr Leu Met Gly Arg
        115                 120                 125

Leu Glu Asp Gly Ser Pro Arg Thr Gly Gln Ile Phe Lys Gln Thr Tyr
    130                 135                 140

Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
            180                 185                 190

<210> SEQ ID NO 3
<211> LENGTH: 174
<212> TYPE: PRT
<213> ORGANISM: Homo sapiens

<400> SEQUENCE: 3

Thr Pro Leu Gly Pro Ala Ser Ser Leu Pro Gln Ser Phe Leu Leu Lys
1               5                   10                  15

Cys Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45

Leu Leu Gly His Ser Leu Gly Ile Pro Trp Ala Pro Leu Ser Ser Cys
    50                  55                  60

```
Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
            115                 120                 125

Ala Leu Gln Pro Thr Gln Gly Ala Met Pro Ala Phe Ala Ser Ala Phe
    130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170

<210> SEQ ID NO 4
<211> LENGTH: 4
<212> TYPE: PRT
<213> ORGANISM: Artificial Sequence
<220> FEATURE:
<223> OTHER INFORMATION: Designed synthetic degradable oligopeptide.

<400> SEQUENCE: 4

Gly Phe Leu Gly
1

<210> SEQ ID NO 5
<211> LENGTH: 4
<212> TYPE: PRT
<213> ORGANISM: Artificial Sequence
<220> FEATURE:
<223> OTHER INFORMATION: Designed synthetic degradable oligopeptide.

<400> SEQUENCE: 5

Gly Gly Phe Gly
1
```